(12) United States Patent
Guindon et al.

(10) Patent No.: US 11,434,255 B2
(45) Date of Patent: Sep. 6, 2022

(54) NUCLEOSIDE AND NUCLEOTIDE ANALOGUES BEARING A QUATERNARY ALL-CARBON STEREOGENIC CENTER AT THE 2' POSITION AND METHODS OF USE AS A CARDIOPROTECTIVE AGENT

(71) Applicant: LCB PHARMA INC., Montréal (CA)

(72) Inventors: Yvan Guindon, Montréal (CA); Philippe Mochirian, Montréal (CA); Mona Nemer, Ottawa (CA)

(73) Assignee: LCB Pharma Inc., Montreal (CA)

( * ) Notice: Subject to any disclaimer, the term of this patent is extended or adjusted under 35 U.S.C. 154(b) by 583 days.

(21) Appl. No.: 16/333,673

(22) PCT Filed: Sep. 18, 2017

(86) PCT No.: PCT/CA2017/051095
§ 371 (c)(1),
(2) Date: Mar. 15, 2019

(87) PCT Pub. No.: WO2018/049534
PCT Pub. Date: Mar. 22, 2018

(65) Prior Publication Data
US 2019/0389897 A1    Dec. 26, 2019

Related U.S. Application Data

(60) Provisional application No. 62/395,401, filed on Sep. 16, 2016, provisional application No. 62/395,411, filed on Sep. 16, 2016, provisional application No. 62/395,430, filed on Sep. 16, 2016.

(51) Int. Cl.

| | |
|---|---|
| *A01N 43/04* | (2006.01) |
| *A61K 31/70* | (2006.01) |
| *C07H 19/10* | (2006.01) |
| *A61P 31/12* | (2006.01) |
| *A61P 35/00* | (2006.01) |
| *C07H 19/20* | (2006.01) |
| *C07H 19/23* | (2006.01) |
| *A61P 9/00* | (2006.01) |

(52) U.S. Cl.
CPC ............... *C07H 19/10* (2013.01); *A61P 9/00* (2018.01); *A61P 31/12* (2018.01); *A61P 35/00* (2018.01); *C07H 19/20* (2013.01); *C07H 19/23* (2013.01)

(58) Field of Classification Search
CPC ........ C07H 19/10; C07H 19/20; C07H 19/23; A61P 9/00; A61P 31/12; A61P 35/00
See application file for complete search history.

(56) References Cited

U.S. PATENT DOCUMENTS 8,846,636 B2 * 9/2014 Guindon ............... A61P 31/16
    514/45
2019/0322693 A1 * 10/2019 Guindon ............... A61P 31/12

FOREIGN PATENT DOCUMENTS

| CN | 106266146 A | * | 1/2017 |
|---|---|---|---|
| WO | 2008087558 A2 | | 7/2008 |
| WO | 2009115927 A2 | | 9/2009 |
| WO | 2012142085 A1 | | 10/2012 |

OTHER PUBLICATIONS

Zhou, S. Y., Mamdani, M., Qanud, K., Shen, J. B., Pappano, A. J., Kumar, T. S., Jacobson, K. A., Hintze, T., Recchia, F. A., and Liang, B. T. (2010) Treatment of heart failure by a methanocarba derivative of adenosine monophosphate: Implication for a role of cardiac purinergic P2X receptors. J. Pharmacol. Exp. Ther. 333, 920-928.
Kumar, T. S., Yang, T., Mishra, S., Cronin, C., Chakraborty, S., Shen, J. B., Liang, B. T., and Jacobson, K. A. (2013) 5'-Phosphate and 5'-phosphonate ester derivatives of (N)-methanocarba adenosine with in vivo cardioprotective activity. J. Med. Chem. 56, 902-914.
Rochette, L., Guenancia, C., Gudjoncik, A., Hachet, O., Zeller, M., Cottin, Y., and Vergely, C. (2015) Anthracyclines/trastuzumab: new aspects of cardiotoxicity and molecular mechanisms. Trends Pharmacol. Sci. 36, 326-348.
Lipshultz, S. E., et al, American Heart Association Congenital Heart Defects Committee of the Council on Cardiovascular Disease in the Young, C. o. B. C. S. C. o. C., and Stroke Nursing, C. o. C. R. (2013) Long-term cardiovascular toxicity in children, adolescents, and young adults who receive cancer therapy: pathophysiology, course, monitoring, management, prevention, and research directions: a scientific statement from the American Heart Association. Circulation 128, 1927-1995.
Zidan, A., Sherief, L. M., El-sheikh, A., Saleh, S. H., Shahbah, D. A., Kamal, N. M., Sherbiny, H. S., and Ahmad, H. (2015) NT-proBNP as early marker of subclinical late cardiotoxicity after doxorubicin therapy and mediastinal irradiation in childhood cancer survivors. Dis. Markers 2015, 513219.

(Continued)

*Primary Examiner* — Patrick T Lewis
(74) *Attorney, Agent, or Firm* — Rothwell, Figg, Ernst & Manbeck, P.C.

(57) ABSTRACT

The compounds are nucleoside and nucleotide analogues that can be used as cardioprotective agents. The compounds include tetrahydrofuranyl or tetrahydrothienyl moieties with quaternary stereogenic all-carbon centers at the 2' position and a phosphonate ester at C5' position.

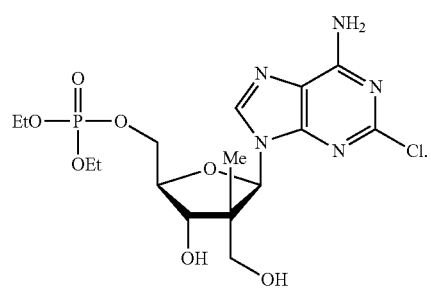

LCB2122

19 Claims, 8 Drawing Sheets

(56) References Cited

OTHER PUBLICATIONS

Aries, A., Paradis, P., Lefebvre, C., Schwartz, R. J., and Nemer, M. (2004) Essential role of GATA-4 in cell survival and drug-induced cardiotoxicity. Proc Natl Acad Sci U S A 101, 6975-6980.
Paradis, P., Dali-Youcef, N., Paradis, F. W., Thibault, G., and Nemer, M. (2000) Overexpression of angiotensin II type I receptor in cardiomyocytes induces cardiac hypertrophy and remodeling. Proc Natl Acad Sci U S A 97, 931-936.
Maharsy, W., Aries, A., Mansour, O., Komati, H., and Nemer, M. (2014) Ageing is a risk factor in imatinib mesylate cardiotoxicity. Eur J. Heart Fail. 16, 367-376.
Van Berlo, J. H., Maillet, M., and Molkentin, J. D. (2013) Signaling effectors underlying pathologic growth and remodeling of the heart. J. Clin. Invest. 123, 37-45.
Charron, F., Tsimiklis, G., Arcand, M., Robitaille, L., Liang, Q., Molkentin, J. D., Meloche, S., and Nemer, M. (2001) Tissue-specific GATA factors are transcriptional effectors of the small GTPase RhoA. Genes Dev 15, 2702-2719.
Aries, A., Whitcomb, J., Shao, W., Komati, H., Saleh, M., and Nemer, M. (2014) Caspase-1 cleavage of transcription factor GATA4 and regulation of cardiac cell fate. Cell Death Dis 5, e1566.
Berge, S. M., Bighley, L. D., and Monkhouse, D. C. (1977) Pharmaceutical salts. J. Pharm. Sci. 66, 1-19.
Broder, H., Gottlieb, R. A., and Lepor, N. E. (2008) Chemotherapy and cardiotoxicity. Rev. Cardiovasc. Med. 9, 75-83.
Pantazi, E., Bejaoui, M., Folch-Puy, E., Adam, R., and Rosello-Catafau, J. (2016) Advances in treatment strategies for ischemia reperfusion injury Expert Opin. Pharmacother. 17, 169-179.
Komati, H., Maharsy, W., Beauregard, J., Hayek, S., and Nemer, M. (2011) ZFP260 is an inducer of cardiac hypertrophy and a nuclear mediator of endothelin-1 signaling. J. Biol. Chem. 286, 1508-1516.
Yang, X. P., Liu, Y. H., Rhaleb, N. E., Kurihara, N., Kim, H. E., and Carretero, O. A. (1999) Echocardiographic assessment of cardiac function in conscious and anesthetized mice. Am. J Physiol. 277, H1967-1974.
Wilkinson, M. C. (2011) "Greener" Friedel-Crafts acylations: a metal- and halogen-free methodology. Org. Lett. 13, 2232-2235.
Bandyopadhyay, S. B., Synthesis of Trifunctional Phosphatidylserine Probes for Identification of Lipid-Binding Proteins. Eur. J Org. Chem. 2011, 751-758.
Cisar, J. S., and Cravatt, B. F. (2012) Fully functionalized small-molecule probes for integrated phenotypic screening and target identification. J. Am. Chem. Soc. 134, 10385-10388.
Tambutet, G., et al. "Dual-Face Nucleoside Scaffold Featuring a Stereogenic All-Carbon Quaternary Center. Intramolecular Silicon Tethered Group-Transfer Reaction", Org. Lett 2014, 16, 5698-5701.
Duplessis, M., et al., "Stereoselective Quaternary Center Construction via Atom-Transfer Radical Cyclization Using Silicon Tethers on Acyclic Precursors", Org. Lett., 2009, 1 (14), pp. 3148-3151.
Kumar, T. S., el al., "5'-Phosphate and 5'-Phosphonate Ester Derivatives of (N)-Methanocarba Adenosine with in Vivo Cardioprotective Activity", J. Med. Chem., 2013, 56, 902-914.
International Search Report cited in PCT/CA2017/051095, dated Nov. 10, 2017, 1 page.

\* cited by examiner

\* Statistically significant relative to the vehicle treated CMCs

¶ Statistically significant relative to the Dox treated CMCs

¶ Statistically significant relative to their respective vehicle treated CMCs

\* Statistically significant relative to the Dox treated CMCs

\* Statistically significant relative to the vehicle treated CMCs
¶ Statistically significant relative to the Imatinib treated CMCs a)

b)

* Statistically significant relative to Pre-Dox

* Statistically significant relative to PreDox

* Statistically significant relative to the Dox treated counterparts a)

b)

NUCLEOSIDE AND NUCLEOTIDE ANALOGUES BEARING A QUATERNARY ALL-CARBON STEREOGENIC CENTER AT THE 2' POSITION AND METHODS OF USE AS A CARDIOPROTECTIVE AGENT

CROSS REFERENCE TO RELATED APPLICATIONS

This application is a 35 U.S.C. 371 National Phase Entry Applications from PCT/CA2017/051095, filed Sep. 18, 2017, which claims benefit, under 35 U.S.C. § 119(e), of U.S. provisional application Ser. No. 62/395,401 filed on Sep. 16, 2016, U.S. provisional application Ser. No. 62/395,411 filed on Sep. 16, 2016, and U.S. provisional application Ser. No. 62/395,430 filed on Sep. 16, 2016. All documents above are incorporated herein in their entirety by reference.

FIELD OF THE INVENTION

The present invention relates to nucleoside and nucleotide analogues.

BACKGROUND OF THE INVENTION

Nucleosides and nucleotides are one of the most important classes of molecules in biology. Nucleotides are the monomeric units of RNA and DNA. They are also required for other numerous functions in the cell. For example, they are involved in phosphate transfer reactions (ATP) as coenzymes (for example $NAD^T$, FAD and coenzyme A) and activated intermediates (S-adenosylmethionine). The nucleosides are transported by known equilibrative nucleoside transporters (hENTs) and human concentrative nucleoside transporters (hCNTs) in the cells.

Various nucleotide analogues are used as pharmaceutical agents. For example, some nucleoside analogues are utilized as antitumor agents, interfering with the synthesis of DNA or RNA in dividing cancerous cells. Various nucleotide analogues in their phosphorylated forms are also included in antisense RNA, siRNA or micro RNA to control the transcription and translation of genes. Various nucleoside or nucleotide analogues also interfere with various purinergic receptors (P1, P2Y and P2X) as either an agonist or an antagonist. 1,2 Nucleoside analogues such as nitrobenzyl-mercaptopurine (NBMPR) can inhibit nucleoside transporters (e.g. ENT-1 and ENT-2).

On another subject, heart failure (HF) occurs when the heart is unable to pump sufficiently to maintain blood flow to meet the body's needs. In heart failure, the heart ventricles may become stiff and do not fill properly between beats. In some cases of heart failure, the heart muscle may become damaged and weakened, and the ventricles dilate to the point that the heart can't pump blood efficiently throughout the body. Over time, the heart can no longer keep up with the normal demands placed on it to pump blood to the body. The term "congestive heart failure" comes from blood backing up into—or congesting—the liver, abdomen, lower extremities and lungs. However, not all heart failure is congestive.

Heart failure has many causes and underlying risk factors. The most common is damage to the heart caused by a myocardial infarction. A significant other common cause is untreated high blood pressure for a long period. In fact, HF often develops after the heart has been damaged or weakened by other conditions such as:

Coronary artery disease and heart attack. Coronary artery disease is the most common form of heart disease and the most common cause of heart failure. Over time, arteries that supply blood to the heart muscle narrow from atherosclerosis, which can cause reduced blood flow to the heart. A heart attack occurs if the plaques formed by the fatty deposits in the arteries rupture and form a blood clot, which may block blood flow to an area of the heart muscle, weakening the heart's pumping ability and often leaving permanent damage. If the damage is significant, it can lead to a weakened heart muscle.

High blood pressure (hypertension). When blood pressure is high, the heart has to work harder than it should to circulate blood throughout the body. Over time, the heart muscle may become thicker to compensate. Eventually, the heart muscle may become either too stiff or too weak to effectively pump blood.

Faulty heart valves. A damaged valve—due to a heart defect, coronary artery disease or heart infection—forces the heart to work harder to keep blood flowing as it should. Over time, this extra work can weaken the heart.

Cardiomyopathy. Heart muscle damage (cardiomyopathy) can have many causes, including several diseases, infections, alcohol abuse and the toxic effect of drugs, such as cocaine or some drugs used for chemotherapy. Genetic factors play an important role in several types of cardiomyopathy, such as dilated cardiomyopathy, hypertrophic cardiomyopathy, arrhythmogenic right ventricular cardiomyopathy, left ventricular noncompaction and restrictive cardiomyopathy.

Myocarditis. Myocarditis is an inflammation of the heart muscle. It is most commonly caused by a virus and can lead to left-sided heart failure.

Congenital heart defects. If the heart and its chambers or valves haven't formed correctly, the healthy parts of the heart have to work harder to pump blood through the heart, which, in turn, may lead to heart failure.

Heart arrhythmias. Abnormal heart rhythms may cause the heart to beat too fast, which creates extra work for the heart. Over time, the heart may weaken, leading to heart failure. A slow heartbeat may prevent the heart from getting enough blood out to the body and may also lead to heart failure.

Other diseases. Chronic diseases—such as diabetes, HIV, hyperthyroidism, hypothyroidism, or a buildup of iron (hemochromatosis) or protein (amyloidosis)—also may contribute to heart failure. Causes of acute heart failure include viruses that attack the heart muscle, severe infections, allergic reactions, blood clots in the lungs, the use of certain medications or any illness that affects the whole body.

The "ejection fraction" is an important measurement of how well a heart is pumping and is used to help classify heart failure and guide treatment. In a healthy heart, the ejection fraction is 50 percent or higher—meaning that more than half of the blood that fills the ventricle is pumped out with each beat. But heart failure can occur even with a normal ejection fraction. This happens if the heart muscle becomes stiff from conditions such as high blood pressure.

At present, there are no effective therapies for the prevention or treatment of HF and about 50% of patients with HF die within 5 years.

On yet another subject, progress in cancer therapeutics over the past decades has been remarkable in improving survival rates and prolonging patients' life. However, it has also revealed undesirable consequences such as the significant increase in cardiovascular disease. In survivors of childhood and adolescent cancers, cancer treatment-induced cardiotoxicity is the third leading cause of mortality, behind recurrence and other malignancies. In adults, heart problems are the most reported post-cancer treatment issues in female survivors after arthritis-osteoporosis while in males it is the number one problem in 5-10 year survivors.[3,4] Chemotherapy associated cardiac toxicity ranges from asymptomatic subclinical changes to life-threatening events like congestive heart failure.

Anthracyclines are known to induce irreversible cardiac damage and their cardiotoxicity is further enhanced by other agents. Moreover, newer, more targeted therapies, including receptor specific monoclonal antibodies and tyrosine kinase inhibitors (TKIs) are starting to be associated with cardiac dysfunction in cancer survivors. In the case of breast cancer, the incidence and severity of the anthracycline Doxorubicin (DOX) cardiotoxicity are known to be dose-dependent, increasing with cumulative doses and the presence of other drugs. The incidence of congestive heart failure goes up to 7% at 550 mg/$m^2$ and 20% of cumulative doses over 700 mg/$m^2$. DOX cardiotoxicity is even more widespread in patients receiving high doses of cyclophosphamide, paclitaxel or Trastuzumab (TRZ), a monoclonal antibody against the extracellular domain of the human epidermal growth factor receptor 2 protein (HER2). The latter is used in HER2 positive breast cancer combined with DOX. Unfortunately, it is now recognized that TRZ potentiates the cardiotoxic side effects of DOX. Recent studies indicated that nearly 1 in 4 women will develop a drug-induced cardiotoxicity. Biomarkers such as troponin-I and N-terminal pro-brain natriuretic peptide (NT-proBNP) combined to tissue Doppler imaging (TDI) are becoming recognized as early markers for subclinical late cardiotoxicity.[5] Irreversible DOX cardiotoxicity is due to its induction of cardiomyocyte death. Cardiomyocytes, the contractile cells of the heart have limited regenerative potential and their loss leads to heart failure.

Drug-induced cardiotoxicity can lead to heart failure which is characterized by cardiac remodeling and decreased ejection fraction (EF). These abnormalities contribute to inadequate cardiac output, poor organ perfusion, activation of the renin angiotensin-aldosterone system (RAAS) and the sympathetic nervous system (SNS).

Unlike other cell types, postnatal cardiomyocytes—which represent less than 30% of the cell number, but nearly 85% of the heart mass—become terminally differentiated and essentially lose their ability to undergo proliferative growth. Loss of cardiomyocytes in the contractile unit of the heart leads to irreversible cardiac remodeling and dysfunction (see FIG. 1). Cardiomyocyte loss is a major feature of human HF and was shown to be sufficient to trigger HF in a variety of experimental animal models.[6-8] The limited regenerative ability of postnatal cardiomyocytes means that their response to stressors generally involves hypertrophy or death.[9]

Despite its vital importance, the mechanisms that control cardiomyocyte survival remain poorly understood. Maintaining energy metabolism and mitochondrial function is critical. Upregulation of oxidative stress genes negatively affects the mitochondria, and leads to cardiac dysfunction. Conversely, anti-apoptotic BCL2 or the mitochondrial biogenesis PGC-1 co-activator proteins promote mitochondrial function and are essential for cardiomyocyte survival in response to stressors. Thus, several genetic programs controlling energy metabolism, contractility, and stress response, need to be coordinately regulated to maintain cardiomyocyte survival and cardiac homeostasis. GATA4 is a master regulator of the genetic program required for cardiomyocyte survival and adaptive stress response.[6,10] Mice with 50% reduction in GATA4 are hypersensitive to DOX cardiotoxicity. In cultured cardiomyocytes, DOX treatment leads to rapid depletion of GATA4 and genetic upregulation of GATA4 prevents DOX cardiotoxicity. Interestingly, Imatinib (a TKI) was also found to induce cardiomyocyte apoptosis and mitochondrial dysfunction through a GATA4-dependent pathway. The mechanism by which GATA4 prevents DOX-induced apoptosis is not fully understood. On the other hand, caspase 1—which is induced at early stages of mitochondrial stress—directly targets GATA4 for degradation.[11] Thus, a reinforcing feedback loop may exist between GATA4 and energy metabolism to maintain cardiomyocyte cell survival. GATA4 activates numerous pro-survival genes including BCL2 family members.[7,11]

SUMMARY OF THE INVENTION

In accordance with the present invention, there is provided:

1. A compound of formula:

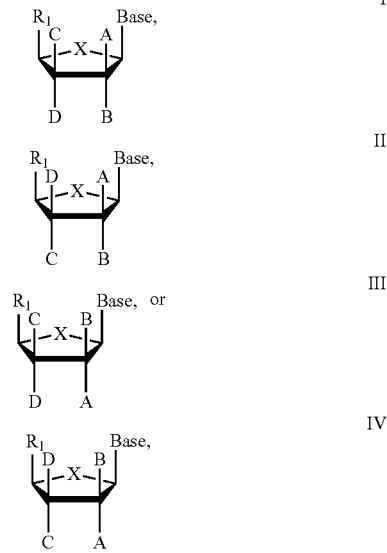

or a pharmaceutically acceptable salt thereof,
wherein:
A and B are $C_1$-$C_6$ alkyl, mono- to per-halo $C_1$-$C_6$ alkyl, —$(CH_2)_n$M, —C≡N, or

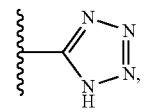

with the proviso that:
A is different from B,
when one of A and B is methyl, the other is not —$CF_3$, and
when one of A and B is $C_2$-$C_6$ alkyl, the other is not $C_2$-$C_6$ fluoroalkyl;
n is 1 to 3;

$R_1$ is

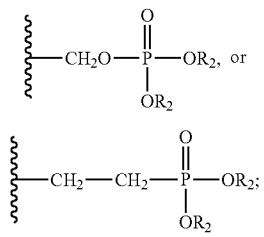

$R_2$ is the same or different, preferably the same, and is $C_1$-$C_6$ alkyl;

M is —$OR_3$, —$SR_3$, aryl, —C(O)$OR_3$, or —OC(O)$R_4$;

$R_3$ is —H, $C_1$-$C_6$ alkyl, aryl, aryl-$C_1$-$C_6$ alkyl, $C_1$-$C_6$ alkylaryl, wherein each of the alkyl and aryl groups is optionally substituted with one or more groups selected from halo, mono- to per-halo $C_1$-$C_6$ alkyl, —CN, —C(O)OH, —C(O)$OR_4$, —$N_3$, —$C_1$-$C_6$ alkyl-C(O)$OR_4$, —$CF_3$, —$C_1$-$C_6$ alkyl-$N_3$, and —$SiF_5$;

$R_4$ is $C_1$-$C_6$ alkyl, aryl, heteroaryl, $C_1$-$C_6$ alkylaryl, aryl-$C_1$-$C_6$ alkyl, wherein each of the alkyl, aryl and heteroaryl groups is optionally substituted with one or more groups selected from halo, —CN, alkynyl, alkynyloxy, —C(O)OH, —$N_3$, —$CF_3$, —$C_1$-$C_6$ alkyl-$N_3$, —$SiF_5$, —$NH_2$, and —$NHR_3$;

C and D are independently —H, halo, azido, —$OR_3$, —CN, or —$CF_3$;

X is O or S; and

Base is:

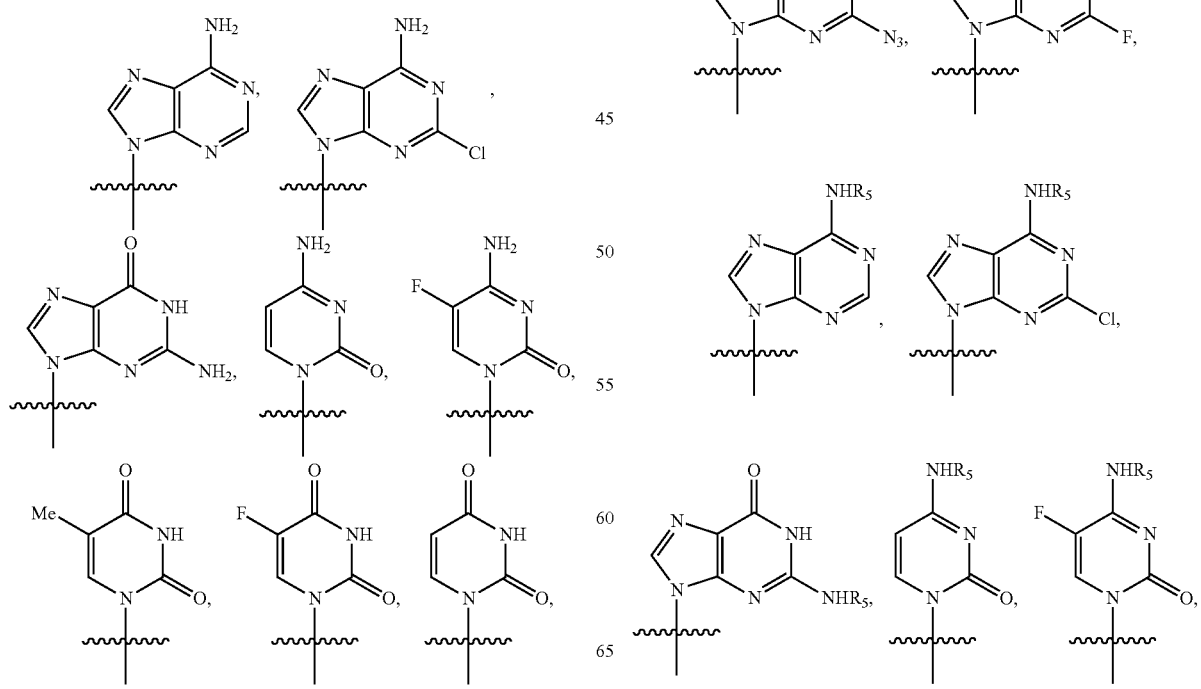

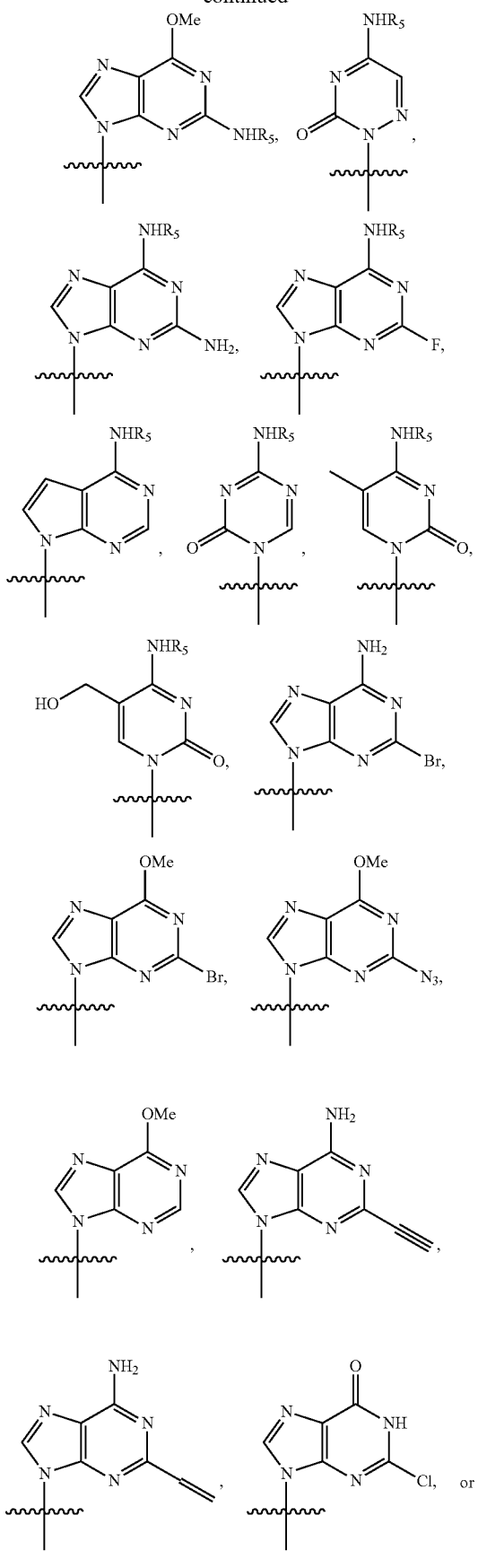

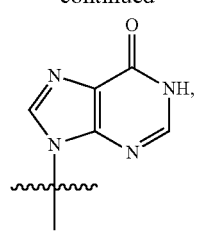

$R_5$ is —H, —C(O)—$C_1$-$C_4$ alkyl, aryl, alkylaryl, or arylalkyl, wherein each of the alkyl group is optionally substituted with one or more groups selected from halo, —$R_4$, —$CF_3$, and —$N_3$.

2. The compound of item 1 being of the formulae

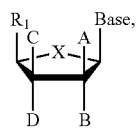

I

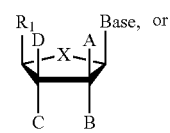

II

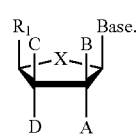

III

3. The compound of item 2 being of the formulae

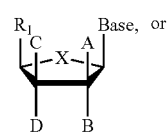

I

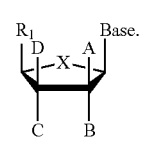

II

4. The compound of item 3 being of the formulae:

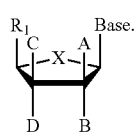

I

5. The compound of any one of items 1 to 4, wherein A and B are $C_1$-$C_6$ alkyl, —$(CH_2)_n$M, —C≡N, or

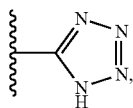

preferably C$_1$-C$_6$ alkyl or —(CH$_2$)$_n$M.
6. The compound of any one of items 1 to 5, wherein one of A or B is C$_1$-C$_6$ alkyl while the other is —(CH$_2$)$_n$M, —C≡N, or

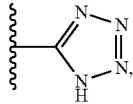

preferably —(CH$_2$)$_n$M.
7. The compound of any one of items 1 to 6, wherein A is C$_1$-C$_6$ alkyl and B is —(CH$_2$)$_n$M, —C≡N, or

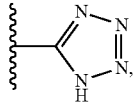

preferably —(CH$_2$)$_n$M.
8. The compound of any one of items 1 to 7, wherein, in A and B, the C$_1$-C$_6$ alkyl is methyl.
9. The compound of any one of items 1 to 8, wherein n is 1.
10. The compound of any one of items 1 to 9, wherein M is —OR$_3$ or —OC(O)R$_4$.
11. The compound of any one of items 1 to 10, wherein M is —OC(O)R$_4$.
12. The compound of any one of items 1 to 10, wherein M is —OR$_3$.
13. The compound of any one of items 1 to 12, wherein R$_3$ is —H, C$_1$-C$_6$ alkyl, or aryl-C$_1$-C$_6$ alkyl, wherein preferably the aryl of the aryl-C$_1$-C$_6$ alkyl is optionally substituted with one or more:
halo,
mono- to per-halo C$_1$-C$_6$ alkyl,
—N$_3$, and/or
—C$_1$-C$_6$ alkyl-N$_3$.
14. The compound of any one of items 1 to 13, wherein the halo optionally substituting the aryl of the aryl-C$_1$-C$_6$ alkyl in R$_3$ is —F.
15. The compound of any one of items 1 to 14, wherein the mono- to per-halo C$_1$-C$_6$ alkyl optionally substituting the aryl of the aryl-C$_1$-C$_6$ alkyl in R$_3$ is per-halo C$_1$-C$_6$ alkyl.
16. The compound of any one of items 1 to 15, wherein the mono- to per-halo C$_1$-C$_6$ alkyl optionally substituting the aryl of the aryl-C$_1$-C$_6$ alkyl in R$_3$ is mono- to per-halo methyl, preferably —CF$_3$.
17. The compound of any one of items 1 to 16, wherein the —C$_1$-C$_6$ alkyl-N$_3$ optionally substituting the aryl of the aryl-C$_1$-C$_6$ alkyl in R$_3$ is —CH$_2$—N$_3$.
18. The compound of any one of items 1 to 17, wherein the aryl-C$_1$-C$_6$ alkyl in R$_3$ is benzyl optionally substituted with one or more:
halo,
mono- to per-halo C$_1$-C$_6$ alkyl,
—N$_3$, and/or
—C$_1$-C$_6$ alkyl-N$_3$.
19. The compound of any one of items 1 to 18, wherein R$_3$ is —H, methyl, isopropyl, benzyl,

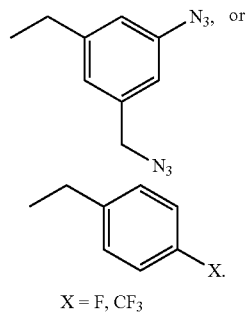

X = F, CF$_3$

20. The compound of any one of items 1 to 19, wherein R$_3$ is —H or benzyl.
21. The compound of any one of items 1 to 20, wherein R$_3$ is —H.
22. The compound of any one of items 1 to 21, wherein, in —OC(O)R$_4$ in M, R$_4$ is aryl or heteroaryl, the aryl and heteroaryl being optionally substituted with one or more groups selected from halo, —CN, alkynyl, alkynyloxy, —C(O)OH, —N$_3$, —CF$_3$, —C$_1$-C$_6$ alkyl-N$_3$, —SiF$_5$, —NH$_2$, and —NHR$_3$.
23. The compound of any one of items 1 to 22, wherein, in —OC(O)R$_4$ in M, the aryl in R$_4$ is benzoylphenyl.
24. The compound of any one of items 1 to 23, wherein, in —OC(O)R$_4$ in M, the heteroaryl in R$_4$ is indole-5-carbonylphenyl.
25. The compound of any one of items 1 to 24, wherein, in —OC(O)R$_4$ in M, the aryl or heteroaryl in R$_4$ is substituted with alkynyl or alkynyloxy.
26. The compound of any one of items 1 to 25, wherein, in —OC(O)R$_4$ in M, the aryl in R$_4$ is substituted with alkynyloxy.
27. The compound of any one of items 1 to 26, wherein, in —OC(O)R$_4$ in M, the heteroaryl in R$_4$ is substituted with alkynyl.
28. The compound of any one of items 1 to 27, wherein, in —OC(O)R$_4$ in M, the alkynyloxy optionally substituting the aryl or heteroaryl in R$_4$ is prop-2-yn-1-yloxy (—O—CH$_2$—C≡CH).
29. The compound of any one of items 1 to 28, wherein, in —OC(O)R$_4$ in M, the alkynyl optionally substituting the aryl or heteroaryl in R$_4$ is prop-2-yn-1-yl (—CH$_2$—C≡CH).
30. The compound of any one of items 1 to 29, wherein, in —OC(O)R$_4$ in M, R$_4$ is

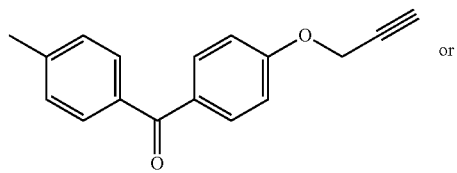

or

-continued

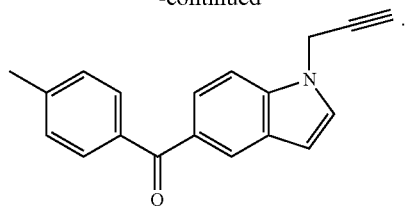

31. The compound of any one of items 1 to 30, wherein C and D are independently —H, halo, or —OR₃.
32. The compound of any one of items 1 to 31, wherein C and D are independently —H, halo, or —OH.
33. The compound of any one of items 1 to 32, wherein one of C or D is —H and the other is halo or —OR₃, wherein —OR₃ preferably represents —OH.
34. The compound of any one of items 1 to 33, wherein C is —H and D is halo or —OR₃, wherein —OR₃ preferably represents —OH.
35. The compound of any one of items 1 to 34, wherein one of C or D is —H and the other is —OR₃, wherein —OR₃ preferably represents —OH.
36. The compound of any one of items 1 to 35, wherein C is —H and D is —OR₃, wherein —OR₃ preferably represents —OH.
37. The compound of any one of items 1 to 36, wherein the halo in C and D is —F.
38. The compound of any one of items 1 to 37, wherein X is O.
39. The compound of any one of items 1 to 38, wherein R₅ represents —H, —C(O)—C₁-C₄ alkyl, arylalkyl, or aryl, wherein the aryl group is optionally substituted with one or more groups selected from halo, —R₄, —CF₃, and —N₃.
40. The compound of any one of items 1 to 39, wherein R₅ represents —H, —C(O)—C₁-C₄ alkyl, arylalkyl, or aryl, wherein each of the aryl groups is optionally substituted with one or more groups selected from halo and —R₄.
41. The compound of any one of items 1 to 40, wherein the alkyl group in —C(O)—C₁-C₄ alkyl in R₅ is propyl.
42. The compound of any one of items 1 to 41, wherein the aryl group of the arylalkyl in R₅ is optionally substituted with one or more —R₄.
43. The compound of any one of items 1 to 42, wherein the aryl group of the arylalkyl in R₅ is unsubstituted.
44. The compound of any one of items 1 to 43, wherein the arylalkyl in R₅ is benzyl.
45. The compound of any one of items 1 to 44, wherein the aryl in R₅ is optionally substituted with one or more, preferably one, F or —CF₃, preferably —CF₃.
46. The compound of any one of items 1 to 45, wherein the aryl in R₅ is phenyl.
47. The compound of any one of items 1 to 46, wherein R₅ represents —H, —C(O)-propyl, benzyl, or p-trifluoromethylphenyl.
48. The compound of any one of items 1 to 47, wherein base is:

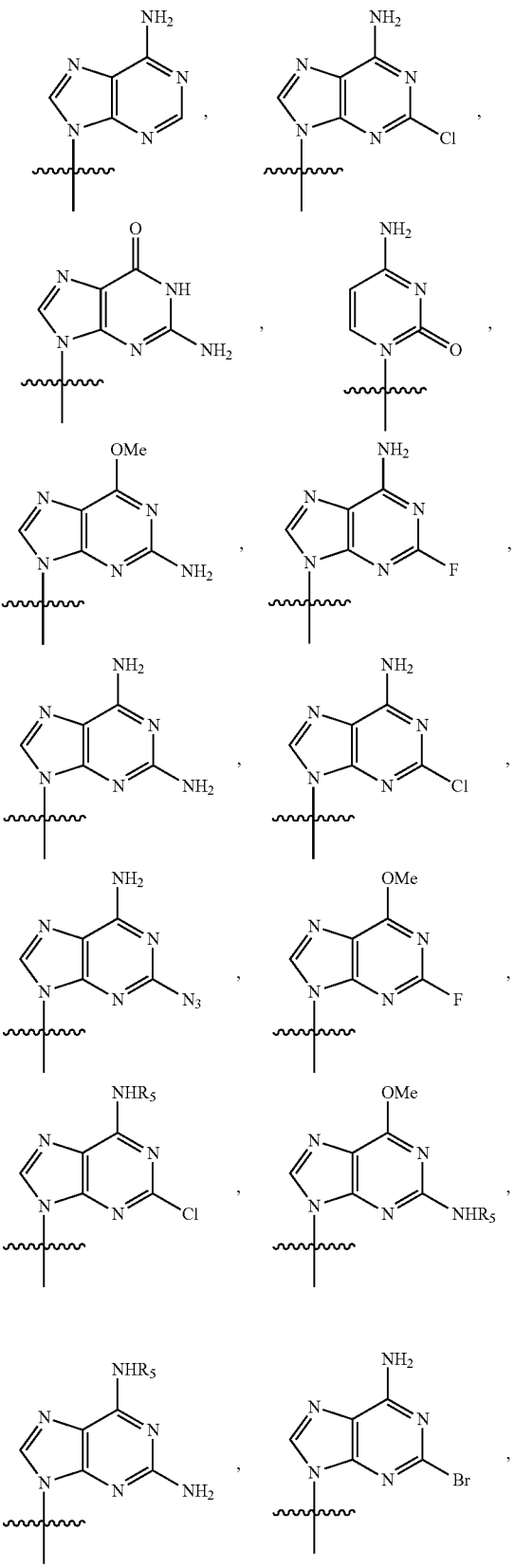

-continued
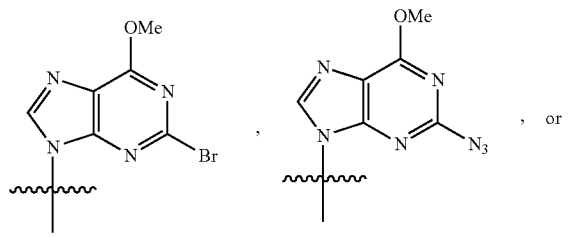 , 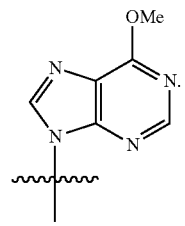 or
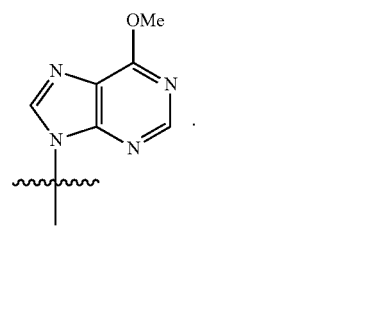
49. The compound of any one of items 1 to 48, wherein base is:
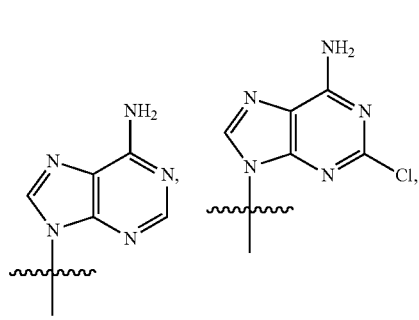
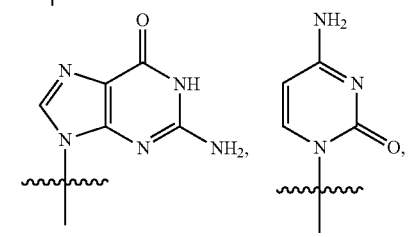
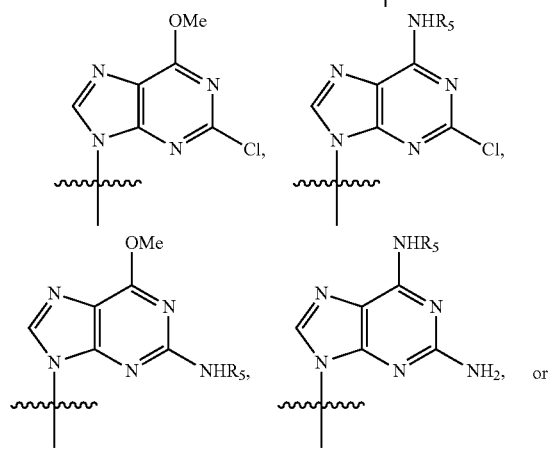
-continued
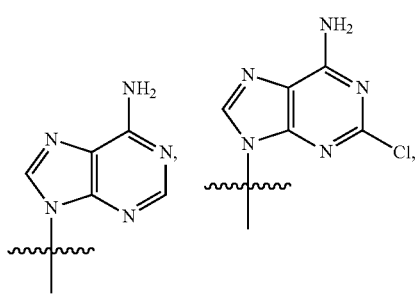
50. The compound of any one of items 1 to 50, wherein base is:
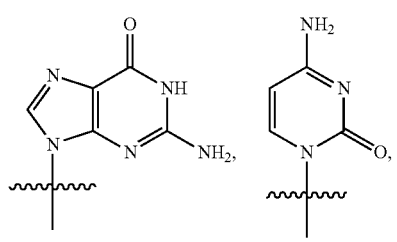
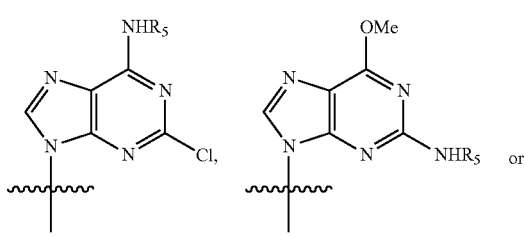
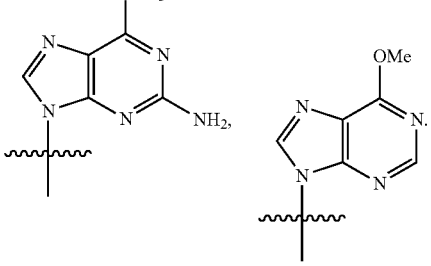
51. The compound of any one of items 1 to 48, wherein base is:

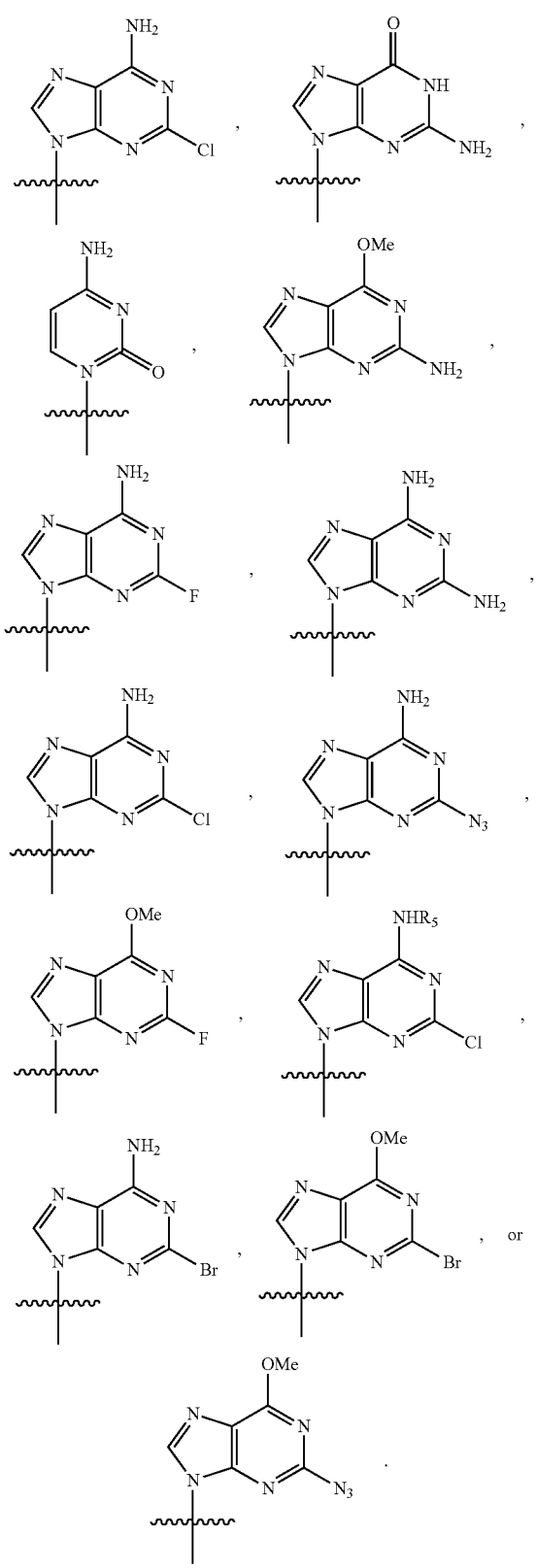
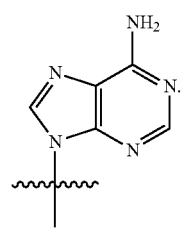 [SMILES: *n1cnc2c(N)ncnc21]
53. The compound of any one of items 1 to 48, wherein base is
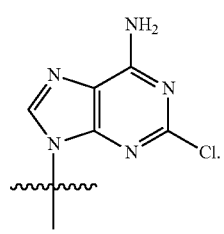 [SMILES: *n1cnc2c(N)nc(Cl)nc21]
54. The compound of any one of items 1 to 48, wherein base is
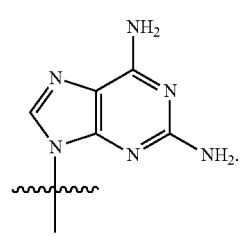 [SMILES: *n1cnc2c(N)nc(N)nc21]
55. The compound of any one of items 1 to 48, wherein base is
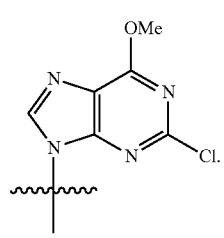
56. The compound of any one of items 1 to 48, wherein base is
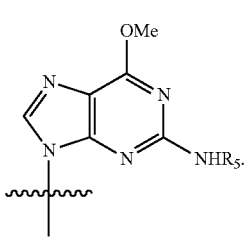
52. The compound of any one of items 1 to 48, wherein base is
57. The compound of any one of items 1 to 48, wherein base is 58. The compound of any one of items 1 to 48, wherein base is

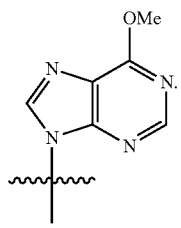 [SMILES: *n1cnc2c(OC)ncnc21]

59. The compound of any one of items 1 to 48, wherein base is

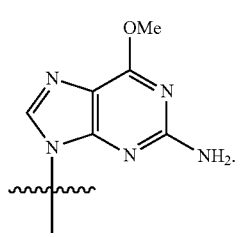 [SMILES: *n1cnc2c(OC)nc(N)nc21]

60. The compound of item 59, wherein $R_5$ is arylalkyl, wherein the aryl group is optionally substituted with one or more groups selected from halo, —$R_4$, —$CF_3$, and —$N_3$.
61. The compound of item 60, wherein $R_5$ is arylalkyl, wherein the aryl group is optionally substituted with —$R_4$.
62. The compound of item 61, wherein $R_5$ is benzyl optionally substituted with —$R_4$.
63. The compound of item 62, wherein $R_5$ is unsubstituted benzyl.
64. The compound of any one of items 1 to 48, wherein base is

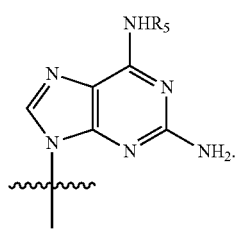

65. The compound of any one of items 1 to 48, wherein base is 4~

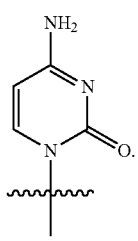 [SMILES: *n1ccc(N)nc1=O]

66. The compound of item 65, wherein $R_5$ represents —C(O)—$C_1$-$C_4$ alkyl or aryl optionally substituted with one or more groups selected from halo, —$R_4$, —$CF_3$, and —$N_3$.
67. The compound of item 66, wherein $R_5$ represents aryl optionally substituted with one or more groups selected from halo, —$R_4$, —$CF_3$, and —$N_3$.
68. The compound of item 67, wherein $R_5$ represents aryl optionally substituted with —$CF_3$.
69. The compound of item 68, wherein $R_5$ represents phenyl optionally substituted with —$CF_3$.
70. The compound of item 69, wherein $R_5$ represents p-trifluoromethylphenyl.
71. The compound of item 66, wherein $R_5$ represents —C(O)—$C_1$-$C_4$ alkyl.
72. The compound of item 71, wherein $R_5$ represents —C(O)-propyl.
73. The compound of item 72, wherein base is

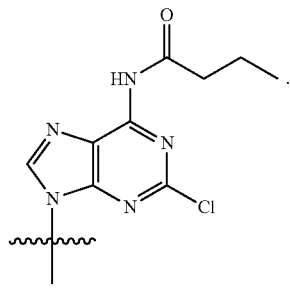 [SMILES: *n1cnc2c(NC(=O)CCC)nc(Cl)nc21]

74. The compound of any one of items 1 to 73, wherein $R_1$ is

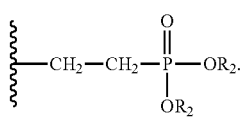

75. The compound of any one of items 1 to 73, wherein $R_1$ is

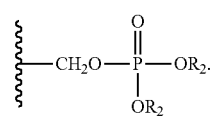

76. The compound of any one of items 1 to 75, wherein $R_2$ is methyl, ethyl, isopropyl or tert-butyl.
77. The compound of any one of items 1 to 76, wherein $R_2$ is ethyl or isopropyl.

78. The compound of any one of items 1 to 77, wherein $R_2$ is ethyl.
79. The compound of item 1 being:
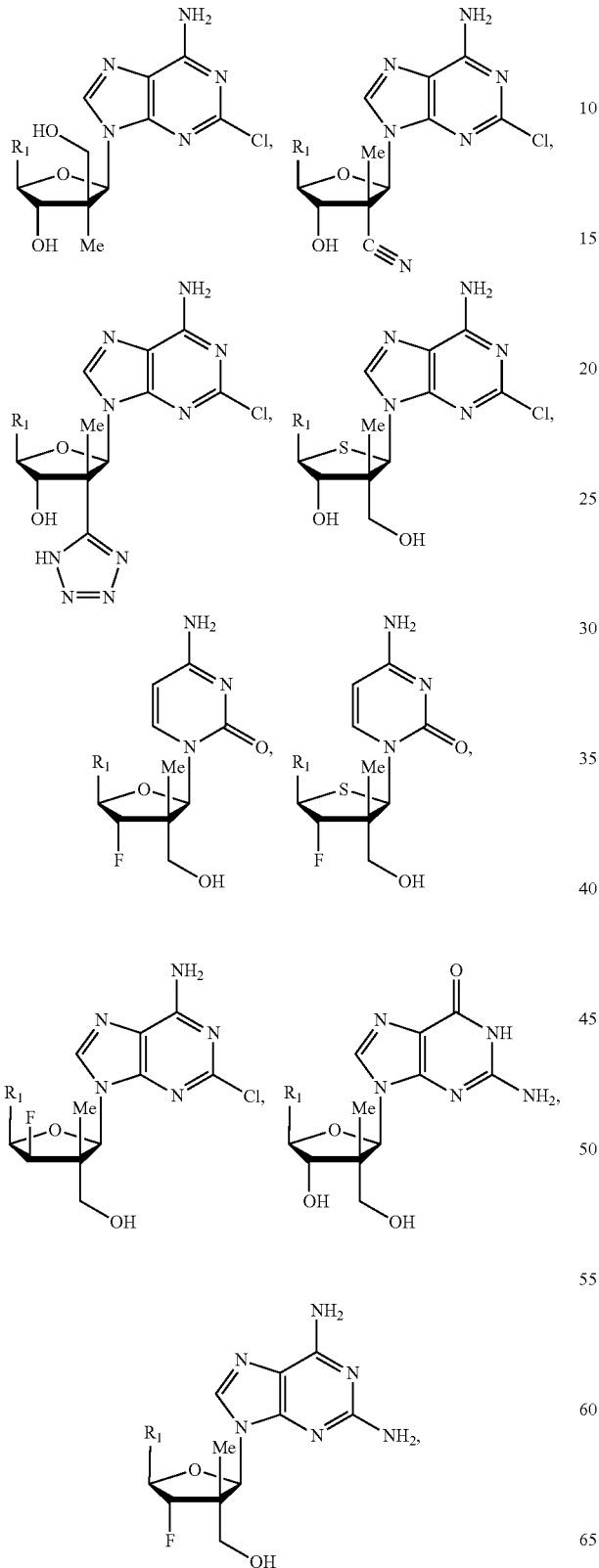
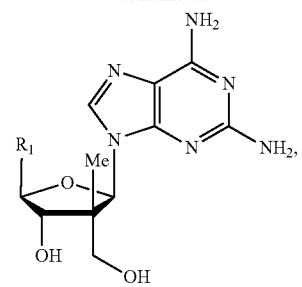
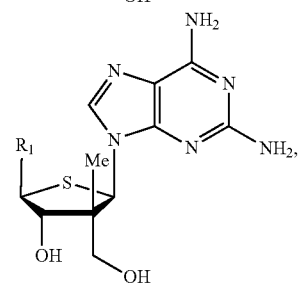
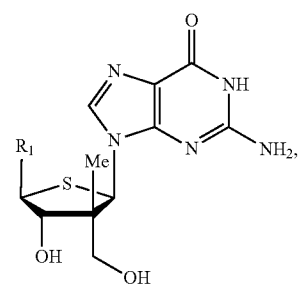
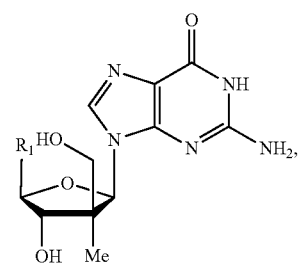
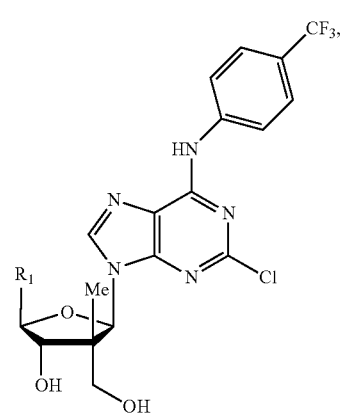

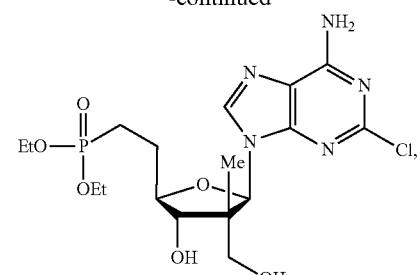
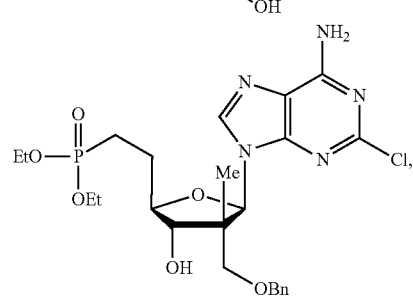
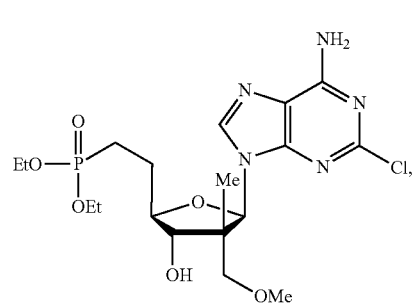
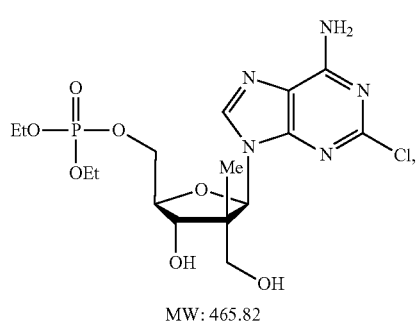
MW: 465.82
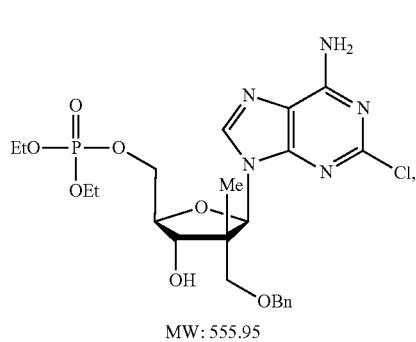
MW: 555.95
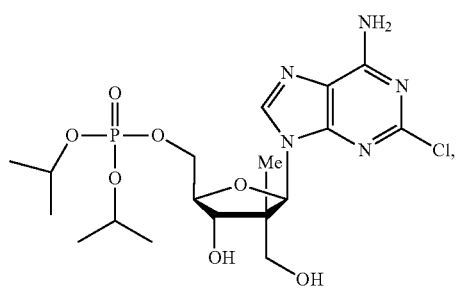
LCB2177
MW: 493.88
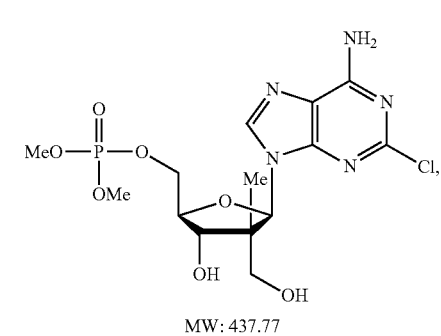
LCB2234
MW: 437.77
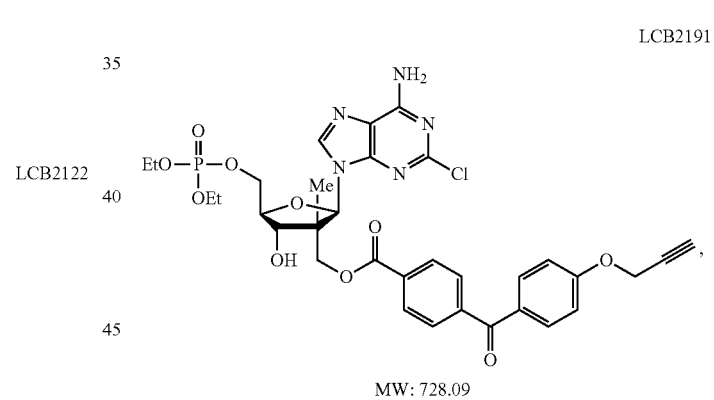
LCB2191
MW: 728.09
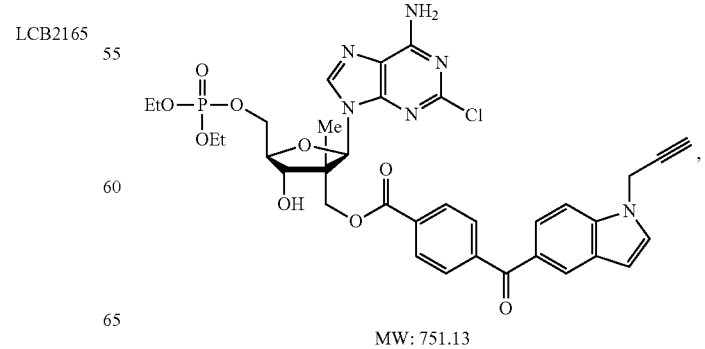
LCB2194
MW: 751.13

23
-continued
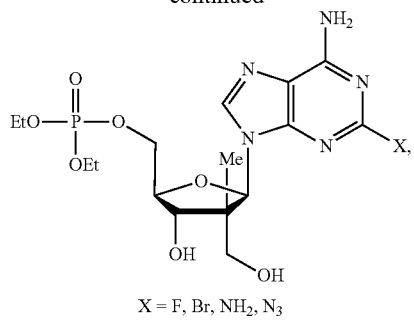
X = F, Br, NH₂, N₃
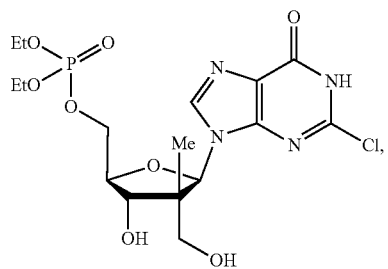
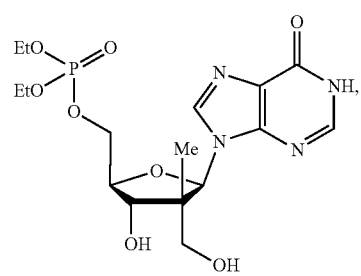
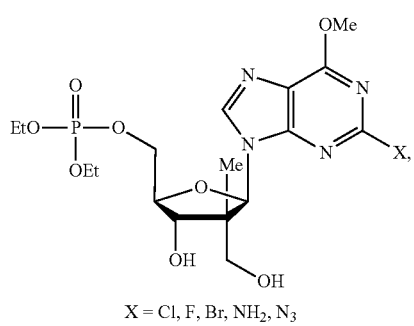
X = Cl, F, Br, NH₂, N₃
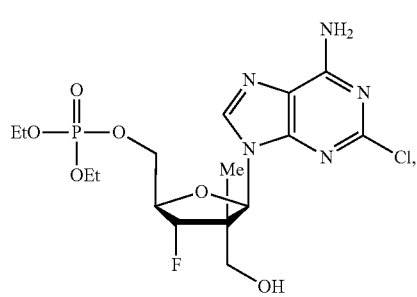
24
-continued
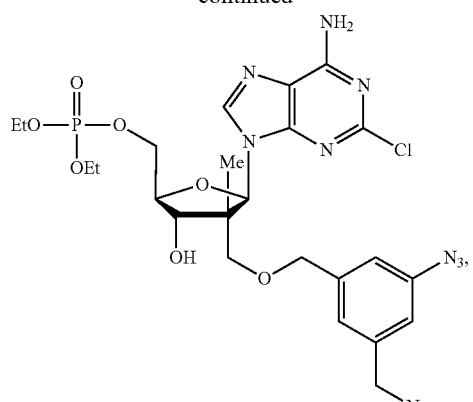
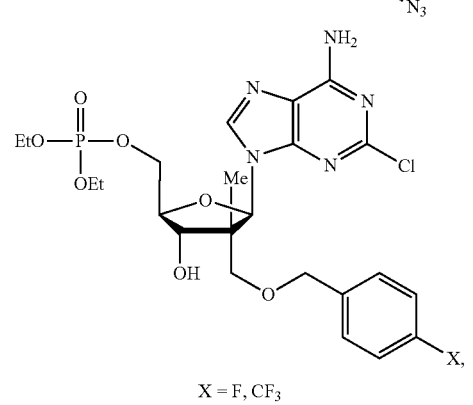
X = F, CF₃
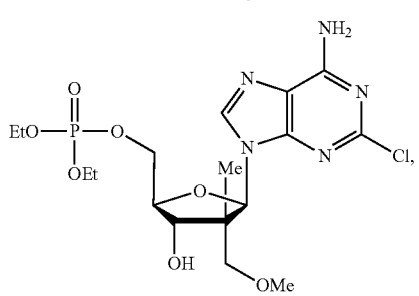
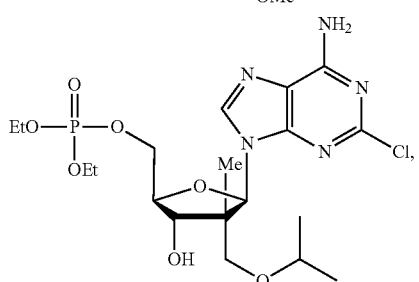
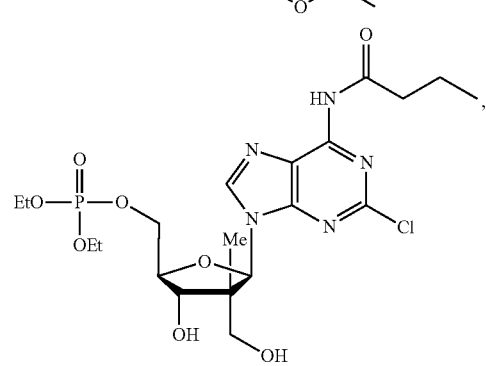

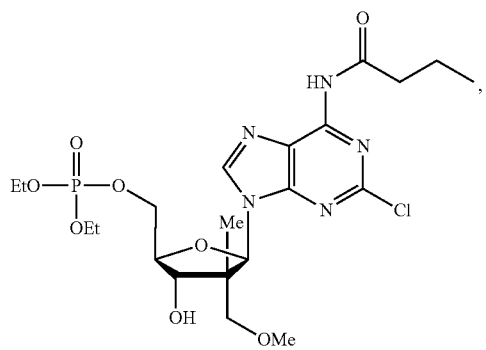
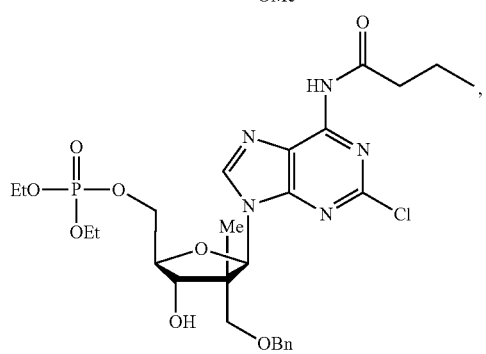
LCB2195
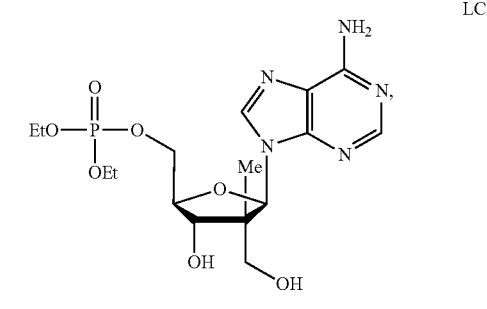
LCB2223
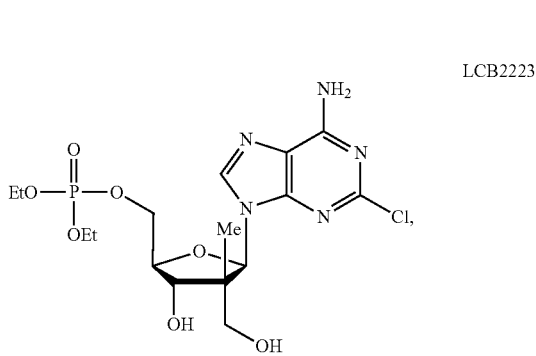
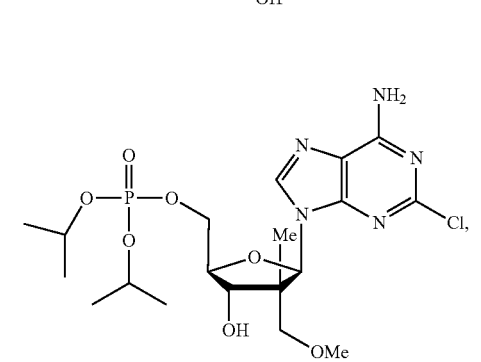
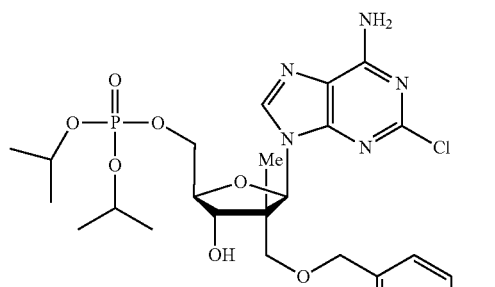
, or
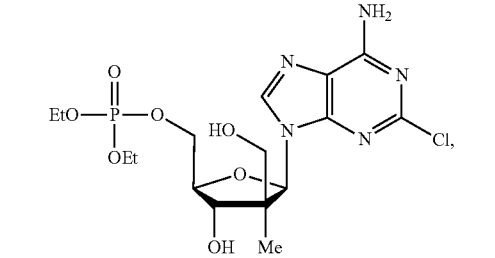
or a pharmaceutically acceptable salt thereof to the subject.
80. The compound of item 79 being:
LCB2122
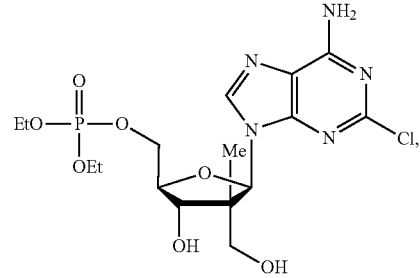
LCB2165
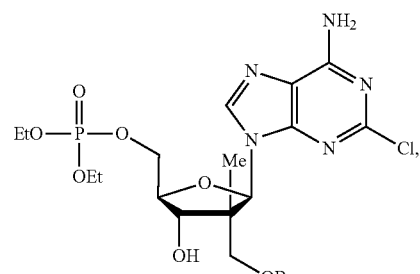
LCB2177
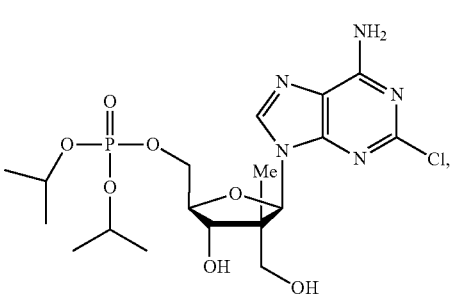

-continued
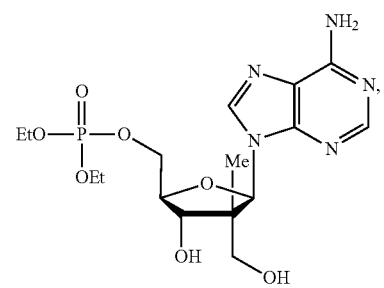
LCB2195
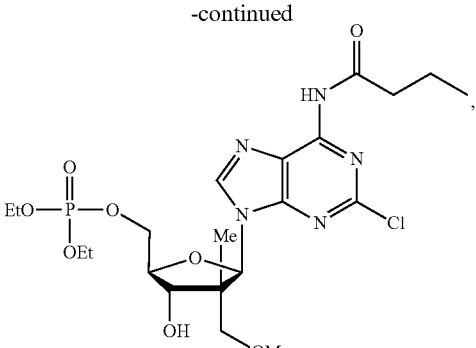
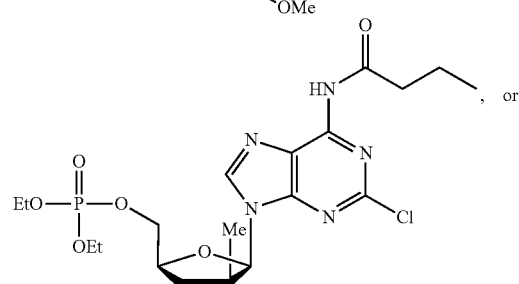
LCB2223
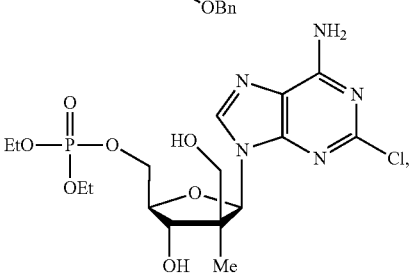
LCB2234
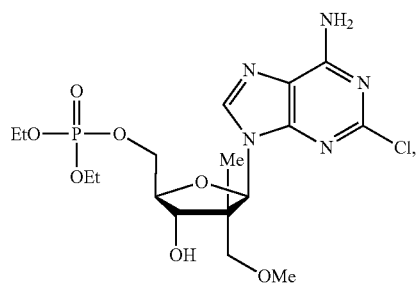
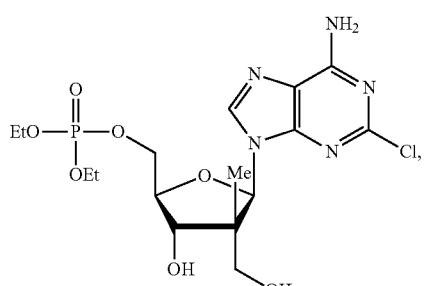
or a pharmaceutically acceptable salt thereof.
81. The compound of item 80 being:
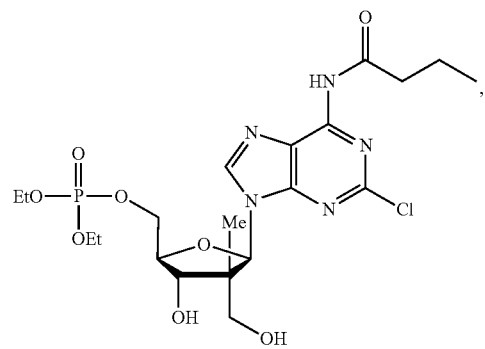
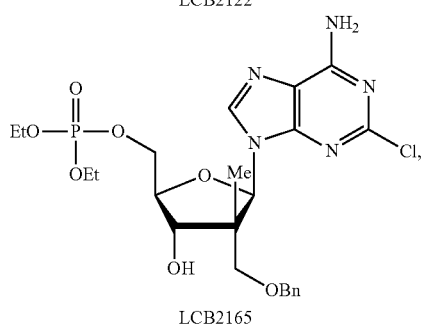
LCB2122
LCB2165

-continued

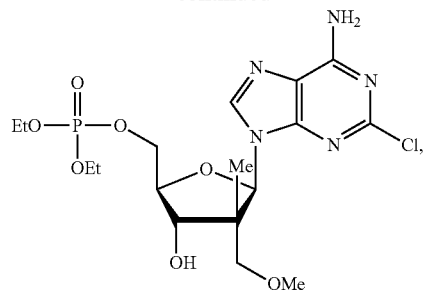

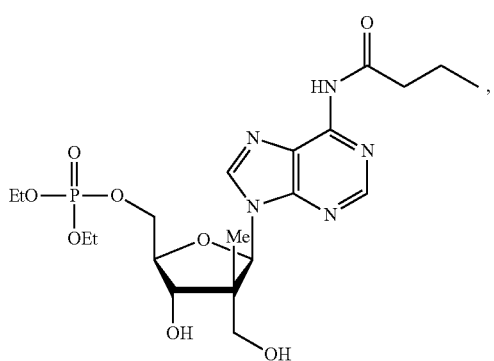

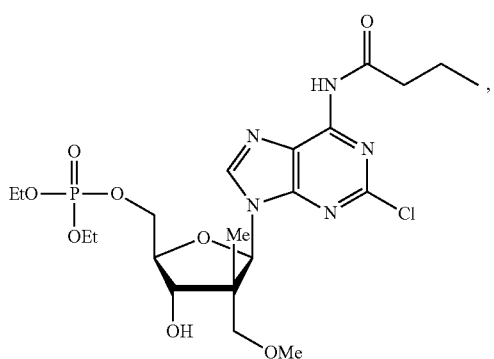

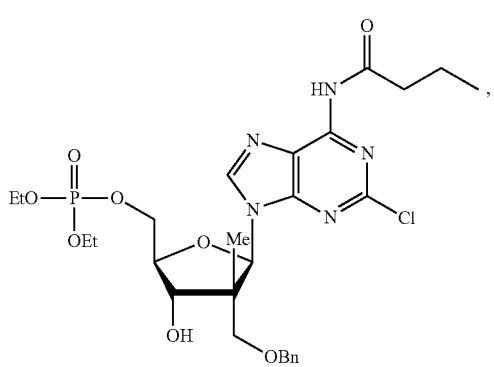

or a pharmaceutically acceptable salt thereof.

82. The compound of item 81 being

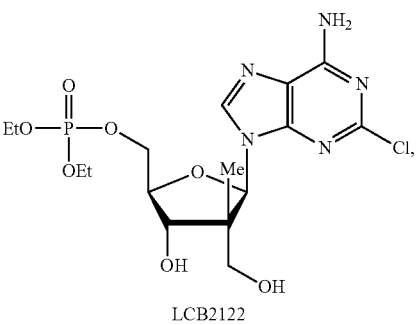

LCB2122 or a pharmaceutically acceptable salt thereof.

83. A pharmaceutical composition comprising a pharmaceutically acceptable carrier, excipient or diluent and the compound of any one of items 1 to 82 or a pharmaceutically acceptable salt thereof.

84. A method of providing cardioprotection in a subject in need thereof, the method comprising administering the compound of any one of items 1 to 82 or a pharmaceutically acceptable salt thereof to the subject.

85. A method of preserving, reducing deterioration of, and/or improving a cardiac function of a heart that has been subjected, is subjected, or will be subjected to a cardiac insult, the method comprising administering the compound of any one of items 1 to 82 or a pharmaceutically acceptable salt thereof to a subject in need thereof.

86. The method of item 84, wherein said cardiac function is ejection fraction or cardiac contractility.

87. A method of preventing, reducing, and/or reversing heart damage due to a cardiac insult, the method comprising administering the compound of any one of items 1 to 82 or a pharmaceutically acceptable salt thereof to a subject in need thereof.

88. The method of item 87, wherein the heart damage includes abnormal cardiomyocyte apoptosis, cardiac remodeling including changes in heart wall thickness, decrease in ejection fraction, poor organ perfusion, and/or loss of cardiac contractility.

89. A method preventing and/or treating of a cardiac dysfunction due, at least in part, to a cardiac insult, the method comprising administering the compound of any one of items 1 to 82 or a pharmaceutically acceptable salt thereof to a subject in need thereof.

90. The method of item 89, wherein the cardiac dysfunction is a chronic condition such as heart failure, for example congestive heart failure, particularly when drug-induced as well as acute conditions such as a myocardial infarction.

91. The method of item 89 or 90, wherein the cardiac dysfunction is coronary artery disease, heart attack, hypertension, faulty heart valves, cardiomyopathy, myocarditis, congenital heart defects, diabetes, or use of a cardiotoxic drug.

92. A method preventing and/or reducing cardiotoxicity associated with use of a cardiotoxic drug, and/or reversing the cardiotoxic effects thereof, the method comprising administering the compound of any one of items 1 to 82 or a pharmaceutically acceptable salt thereof to a subject in need thereof.

93. The method of item 92, wherein the cardiotoxic drug is doxorubicin or imatinib.
94. The method of item 93, wherein the cardiotoxic drug is doxorubicin.

DETAILED DESCRIPTION OF THE INVENTION

Figure 1:
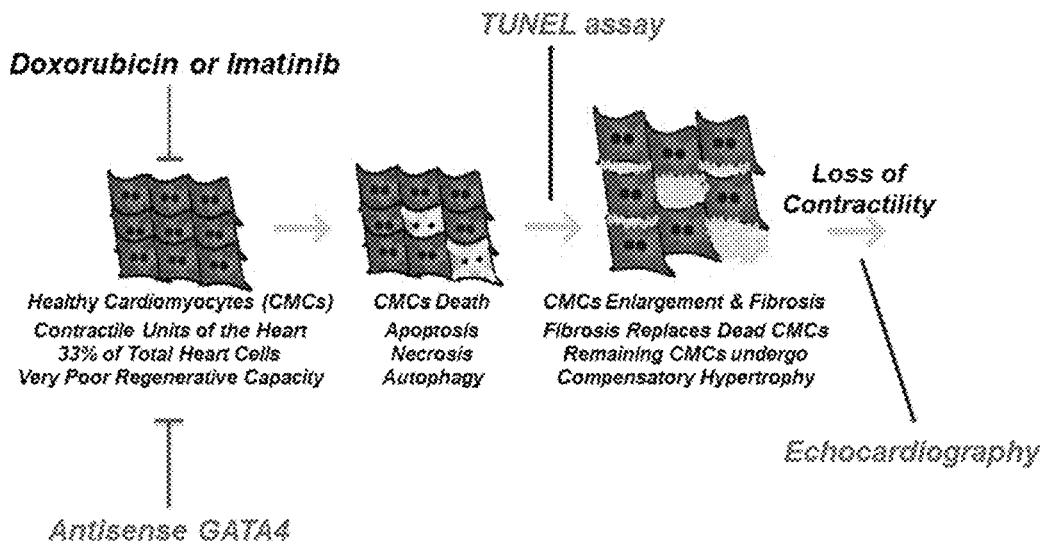
FIG. 1 is a scheme showing the typical progression of chemotherapy-induced heart failure.

An object of this invention is the identification of novel nucleoside and nucleotide analogues that can be used as cardioprotective agents. The invention thus relates to compounds useful as cardioprotective agents and to pharmaceutical compositions comprising these compounds.

The nucleoside and nucleotide analogues of the invention comprise tetrahydrofuranyl or tetrahydrothienyl moieties with a quaternary stereogenic all-carbon center at the 2' position and a phosphonate ester at C5'. Pharmaceutically acceptable salts of these compounds are also part of the invention.

The invention provides compounds of formula:

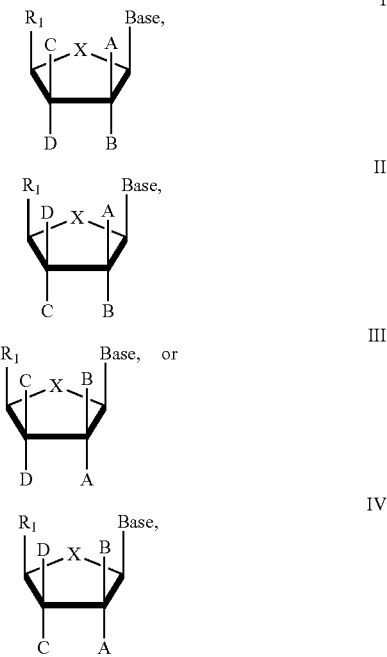

or a pharmaceutically acceptable salt thereof,
wherein:
A and B are $C_1$-$C_6$ alkyl, mono- to per-halo $C_1$-$C_6$ alkyl, —(CH$_2$)$_n$M, —C≡N, or

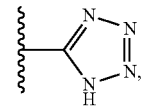

with the proviso that:
A is different from B,
when one of A and B is methyl, the other is not —CF$_3$, and
when one of A and B is $C_2$-$C_6$ alkyl, the other is not $C_2$-$C_6$ fluoroalkyl;
n is 1 to 3;
$R_1$ is

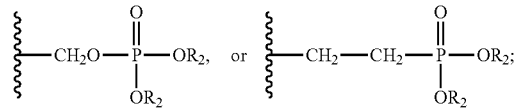

$R_2$ is the same or different, preferably the same, and is $C_1$-$C_6$ alkyl;
M is —OR$_3$, —SR$_3$, aryl, —C(O)OR$_3$, or —OC(O)R$_4$;
$R_3$ is —H, $C_1$-$C_6$ alkyl, aryl, aryl-$C_1$-$C_6$ alkyl, $C_1$-$C_6$ alkylaryl, wherein each of the alkyl and aryl groups is optionally substituted with one or more groups selected from halo, mono- to per-halo $C_1$-$C_6$ alkyl, —CN, —C(O)OH, —C(O)OR$_4$, —N$_3$, —C$_1$-C$_6$ alkyl-C(O)OR$_4$, —CF$_3$, —C$_1$-C$_6$ alkyl-N$_3$, and —SiF$_5$;

R$_4$ is C$_1$-C$_6$ alkyl, aryl, heteroaryl, C$_1$-C$_6$ alkylaryl, aryl-C$_1$-C$_6$ alkyl, wherein each of the alkyl, aryl and heteroaryl groups is optionally substituted with one or more groups selected from halo, —CN, alkynyl, alkynyloxy, —C(O)OH, —N$_3$, —CF$_3$, —C$_1$-C$_6$ alkyl-N$_3$, —SiF$_5$, —NH$_2$, and —NHR$_3$;

C and D are independently —H, halo, azido, —OR$_3$, —CN, or —CF$_3$;

X is O or S; and

Base is:

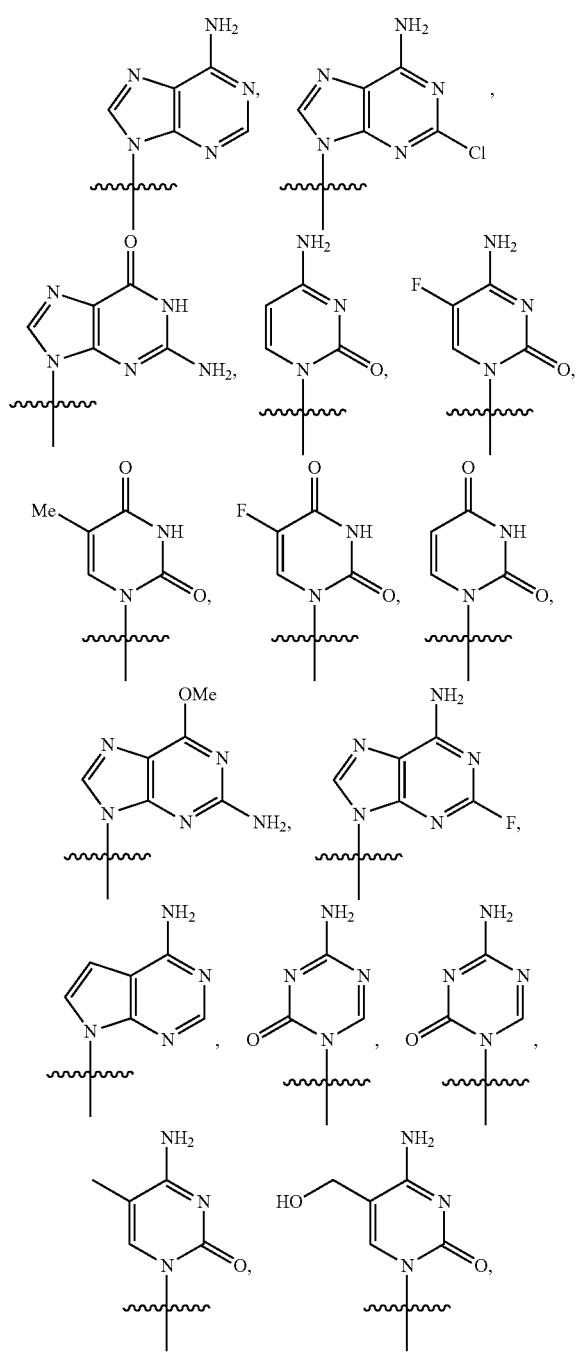

-continued

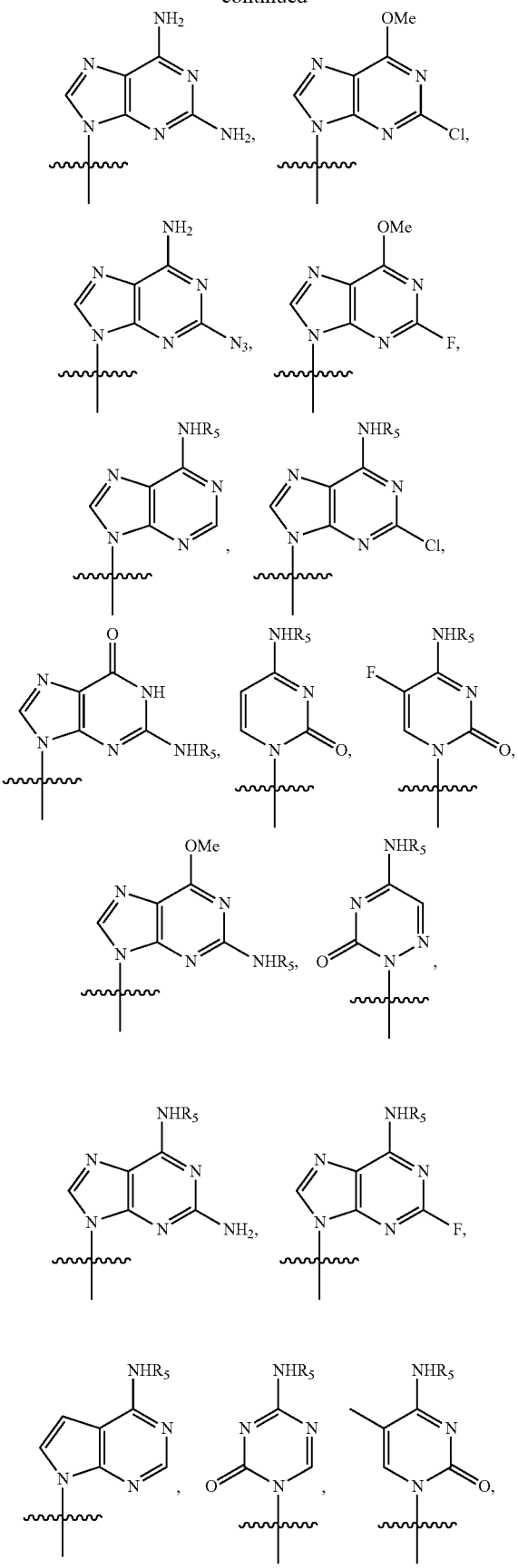

-continued

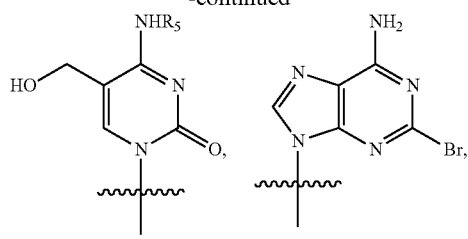

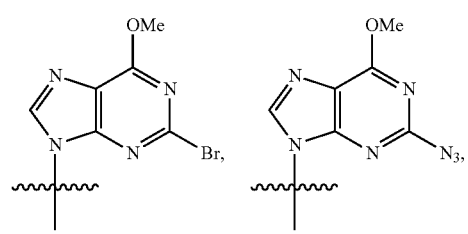

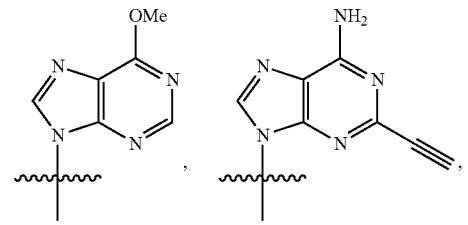

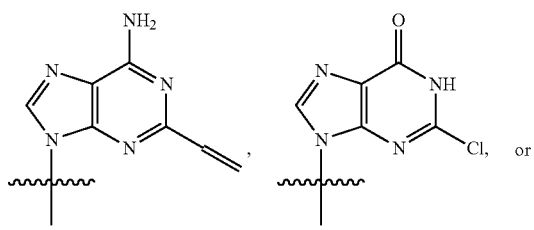

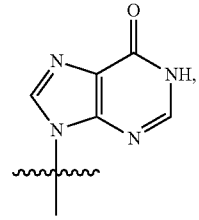

$R_5$ is —H, —C(O)—$C_1$-$C_4$ alkyl, aryl, alkylaryl, or arylalkyl, wherein each of the alkyl group is optionally substituted with one or more groups selected from halo, —$R_4$, —$CF_3$, and —$N_3$.

In embodiments, the compound of the formulae:

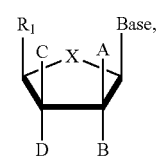  I

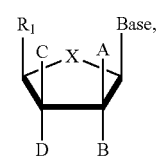  II

-continued

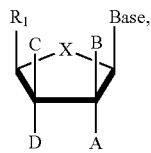  III preferrably of formulae:

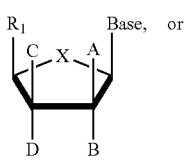  I

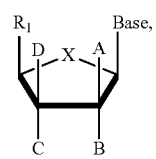  II and more preferably of formulae:

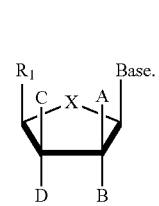  I

In embodiments $R_1$ are

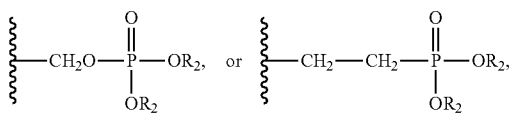

wherein $R_2$ is methyl, ethyl, isopropyl, butyl, tert-butyl as described above. In more preferred embodiments, $R_1$ is —$CH_2OP(O)(OR_2)_2$. In yet more preferred embodiments $R_1$ is —$CH_2OP(O)(OEt)_2$.

In embodiments, A and B are $C_1$-$C_6$ alkyl, —$(CH_2)_n$M, —C≡N, or

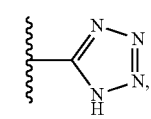

preferably $C_1$-$C_6$ alkyl or —$(CH_2)_n$M, wherein n and M are as defined above. In preferred embodiments, one of A or B is $C_1$-$C_6$ alkyl while the other is —$(CH_2)_n$M, —C≡N, or

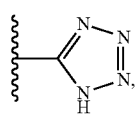

preferably —(CH$_2$)$_n$M. In more preferred embodiments, A is C$_1$-C$_6$ alkyl and B is —(CH$_2$)$_n$M, —C≡N, or

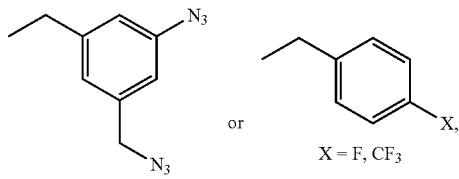

preferably —(CH$_2$)$_n$M. In yet more preferred embodiments:
the C$_1$-C$_6$ alkyl is methyl,
n is 1,
M is —OR$_3$ or —O(CO)R$_4$, preferably —OR$_3$, R$_3$ and R$_4$ being as defined above.

In yet more preferred embodiments, R$_3$ in M of A/B is —H, C$_1$-C$_6$ alkyl, or aryl-C$_1$-C$_6$ alkyl, the aryl of the aryl-C$_1$-C$_6$ alkyl being optionally substituted with one or more:
halo, preferably —F,
mono- to per-halo C$_1$-C$_6$ alkyl, preferably per-halo C$_1$-C$_6$ alkyl, the alkyl preferably being methyl, the halo preferably being —F, more preferably —CF$_3$,
N$_3$, and/or
—C$_1$-C$_6$ alkyl-N$_3$, preferably —CH$_2$—N$_3$.

In embodiments, the aryl-C$_1$-C$_6$ alkyl is benzyl optionally substituted as noted above. In embodiments, the alkyl is methyl or propyl. In more preferred embodiments, R$_3$ is —H, methyl, isopropyl, benzyl, or

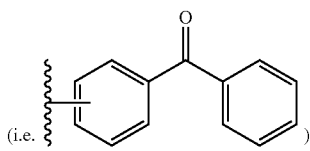

preferably —H or benzyl, and more preferably —H.

In yet more preferred embodiments, R$_4$ in M of A/B is aryl or heteroaryl optionally substituted as noted above, preferably benzoylphenyl

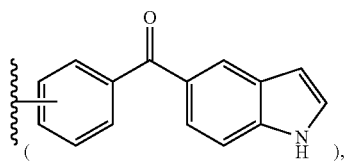

or indole-5-carbonylpheny;

both of which optimally and preferably substituted with alkynyl (preferably prop-2-yn-1-yl (—CH$_2$—C≡CH)) or alkynyloxy (preferably prop-2-yn-1-yloxy (—O—CH$_2$—C≡CH)), wherein the aryl is preferably substituted with alkynyloxy and the heteroaryl is preferably substituted with alkynyl. More preferably, R$_3$ is In embodiments, C and D are independently —H, halo (preferably —F), —OR$_3$ (preferably —OH), —CN and CF$_3$, preferably —H, halo, or —OR$_3$ (preferably —OH). In preferred embodiments, one of C or D is —H and the other is halo or —OR$_3$ (preferably the "other" is —OR$_3$, which is preferably —OH). In more preferred embodiments, C is —H and D is halo or —OR$_3$ (preferably D is —OR$_3$, which is preferably —OH). In yet more preferred embodiments, C is H and D is —OR$_3$ (preferably —OH).

In embodiments, X is O.

In embodiments, R$_5$ represents —H, —C(O)—C$_1$-C$_4$ alkyl, arylalkyl, or aryl, wherein each of the aryl groups is optionally substituted with one or more groups selected from halo, —R$_4$, —CF$_3$, and —N$_3$, preferably halo and —R$_4$. In embodiments, R$_5$ represents —H. In embodiments, R$_5$ represents —C(O)—C$_1$-C$_4$ alkyl. In embodiments, the alkyl group in —C(O)—C$_1$-C$_4$ alkyl in R$_5$ is propyl. In embodiments, R$_5$ represents arylalkyl. In embodiments, the aryl group of the arylalkyl in R$_5$ is optionally substituted with one or more —R$_4$. In other embodiments, the aryl group of the arylalkyl in R$_5$ is unsubstituted. In embodiments, the arylalkyl in R$_5$ is benzyl. In embodiments, R$_5$ represents aryl. In embodiments, the aryl in R$_5$ is optionally substituted with one or more, preferably one, F or —CF$_3$, preferably —CF$_3$. In embodiments, the aryl in R$_5$ is phenyl. In preferred embodiments, R$_5$ represents —H, —C(O)-propyl, benzyl, or p-trifluoromethylphenyl.

In preferred embodiments, base is:
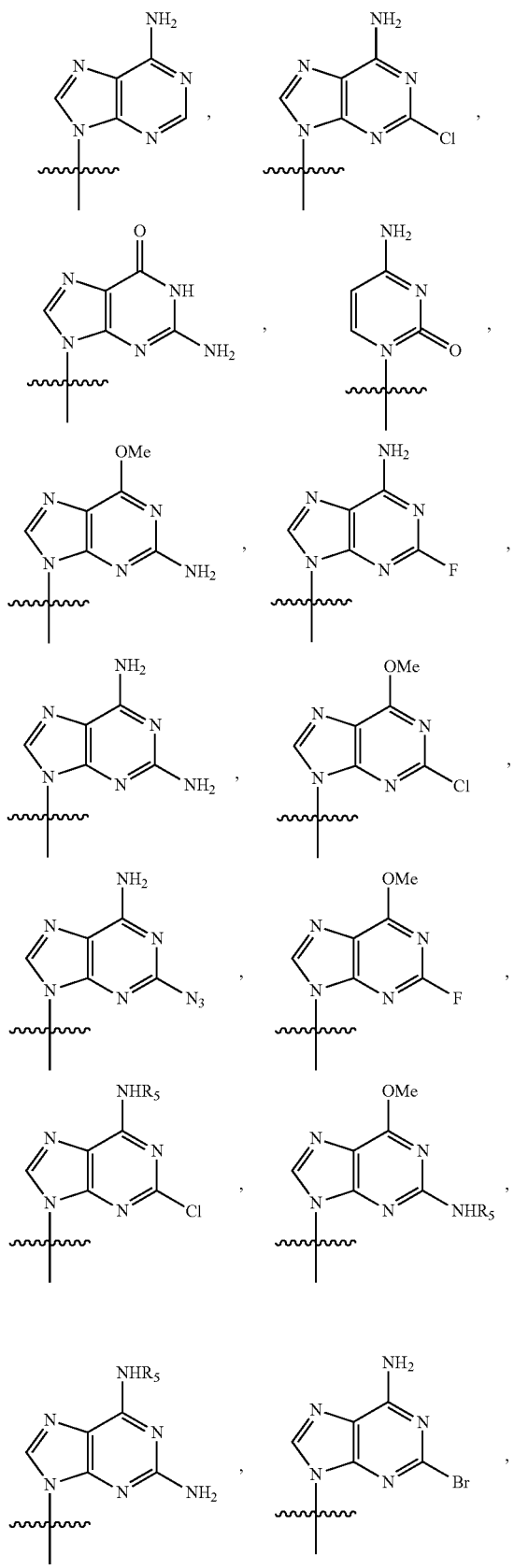
preferably base is:
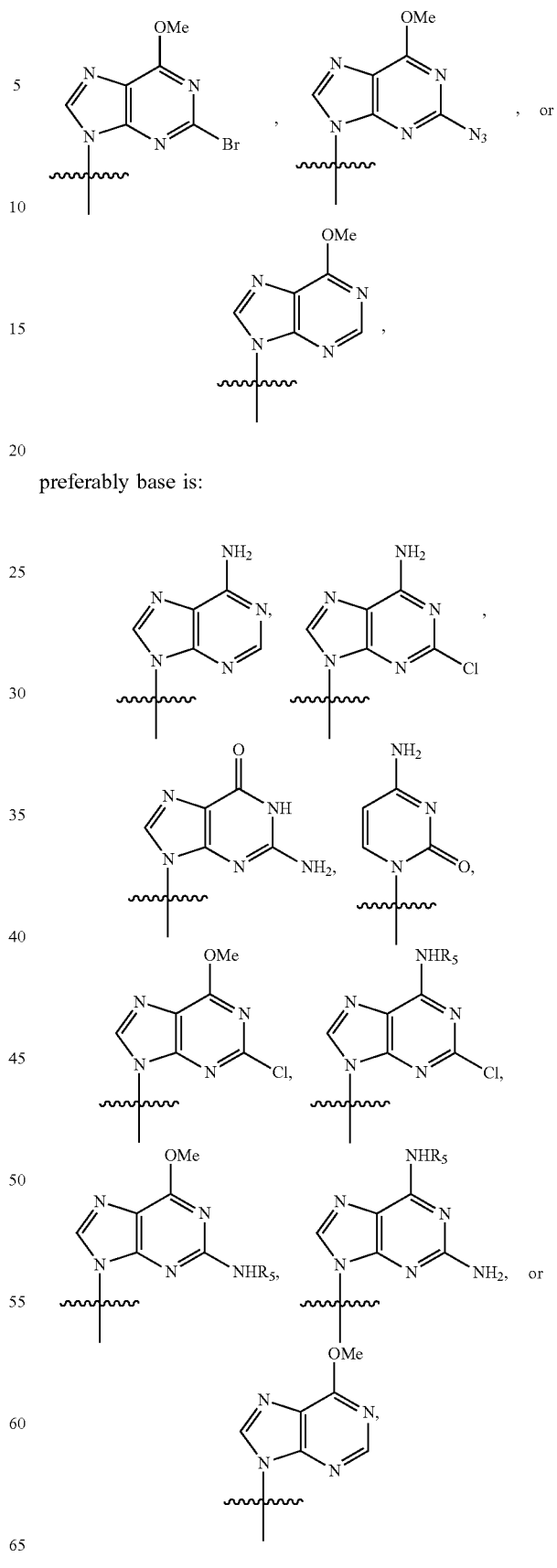

more preferably base is:
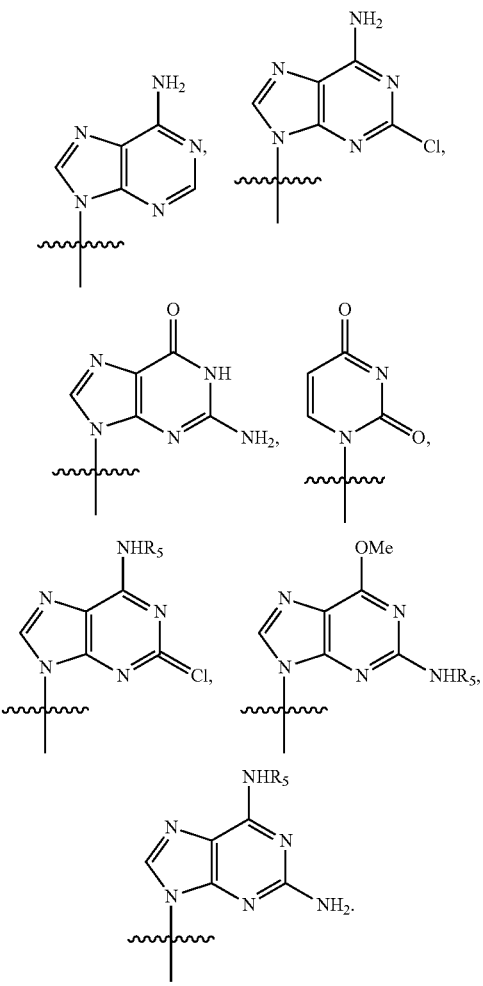
In embodiments, base is:
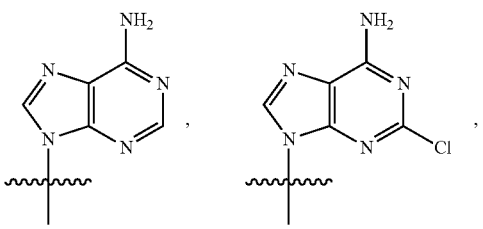
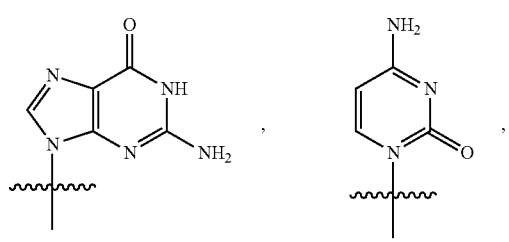
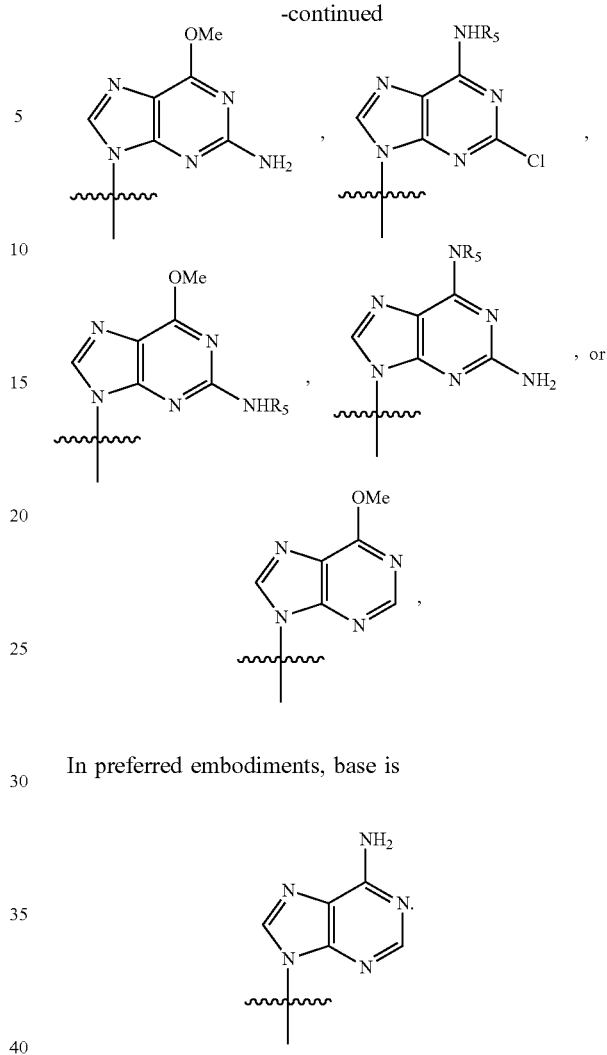
In preferred embodiments, base is
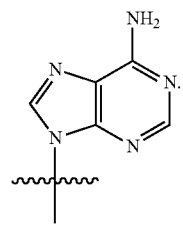 [SMILES: *n1cnc2c(N)ncnc21]
In preferred embodiments, base is
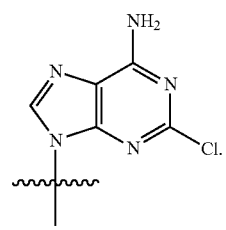 [SMILES: *n1cnc2c(N)nc(Cl)nc21]
In preferred embodiments, base is
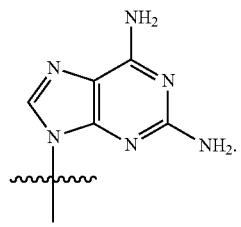

In preferred embodiments, base is

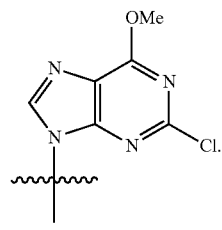 [SMILES: *n1cnc2c(OC)nc(Cl)nc21]

In preferred embodiments, base is

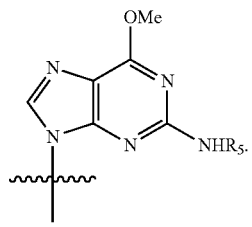

In preferred embodiments, base is

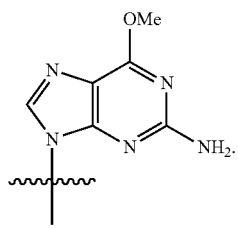 [SMILES: *n1cnc2c(OC)nc(N)nc21]

In preferred embodiments, base is

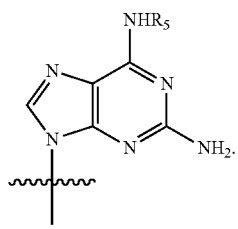

In such embodiments, $R_5$ is preferably arylalkyl, wherein the aryl group is optionally substituted with one or more groups selected from halo, —$R_4$, —$CF_3$, and —$N_3$, preferably —$R_4$. In preferred embodiments, $R_5$ is benzyl optionally substituted with —$R_4$ and more preferably $R_5$ is unsubstituted benzyl.

In preferred embodiments, base is

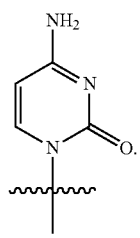 [SMILES: *n1ccc(N)nc1=O]

In preferred embodiments, base is

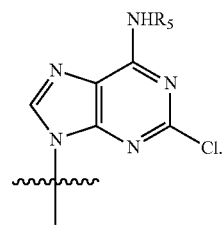

In such embodiments, $R_5$ preferably represents —C(O)—$C_1$-$C_4$ alkyl or aryl optionally substituted with one or more groups selected from halo, —$R_4$, —$CF_3$, and —$N_3$. In embodiments, $R_5$ represents aryl optionally substituted with one or more groups selected from halo, —$R_4$, —$CF_3$, and —$N_3$, preferably —$CF_3$. In preferably embodiments, $R_5$ represents phenyl optionally substituted with —$CF_3$, and most preferably p-trifluoromethylphenyl. In embodiments, $R_5$ represents —C(O)—$C_1$-$C_4$ alkyl and most preferably —C(O)-propyl. In preferred embodiments, base is

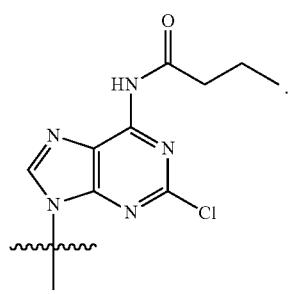 [SMILES: *n1cnc2c(NC(=O)CCC)nc(Cl)nc21]

As noted above, $R_1$ is

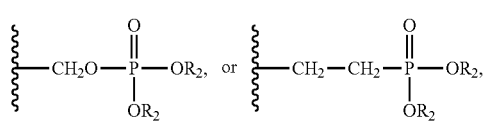

$R_2$ being as defined above. In embodiments, $R_1$ is

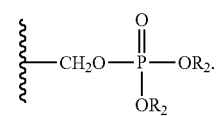

In alternative embodiments, $R_1$ is

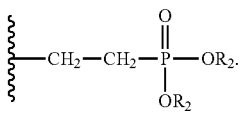

In embodiments, $R_2$ is methyl, ethyl, isopropyl or tert-butyl, preferably ethyl or isopropyl, more preferably ethyl. In a preferred embodiment, $R_1$ represents

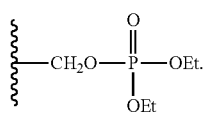
Preferred compounds of the invention include:
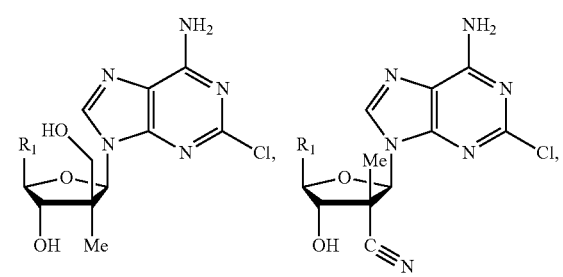
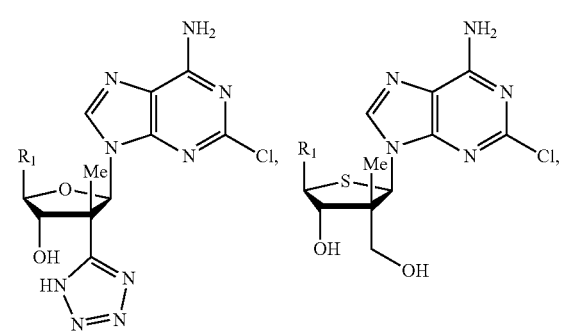
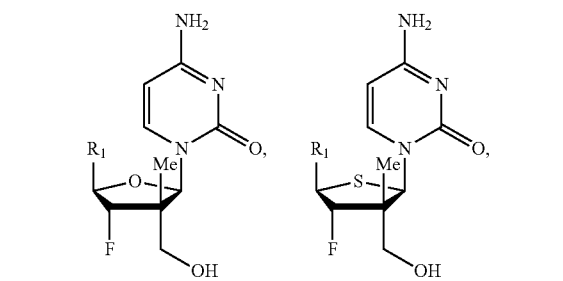
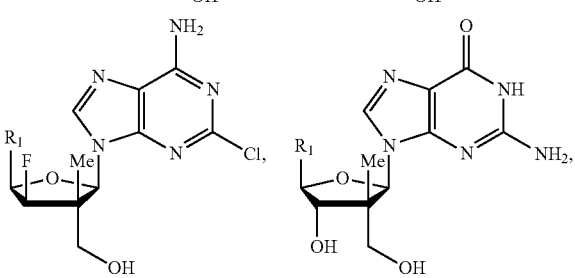
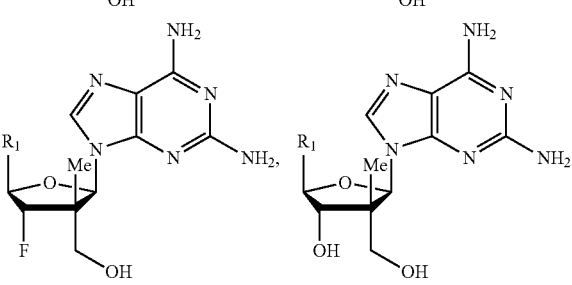
-continued
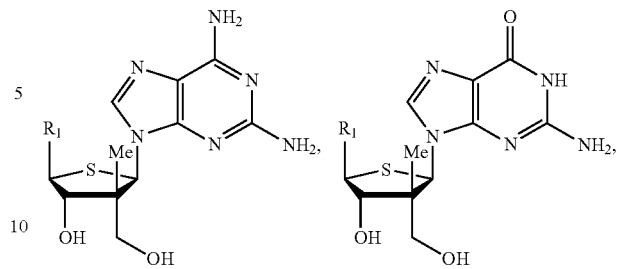
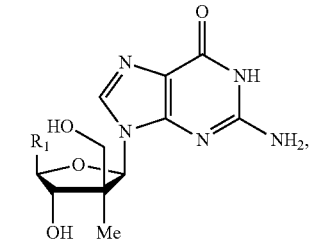
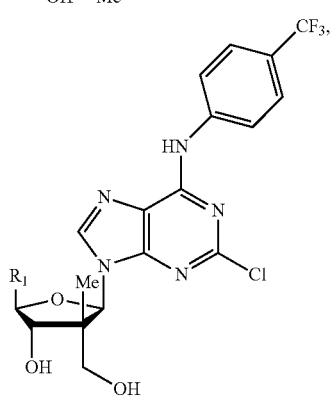
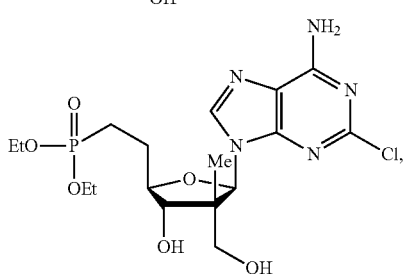
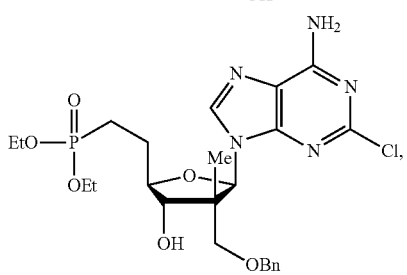
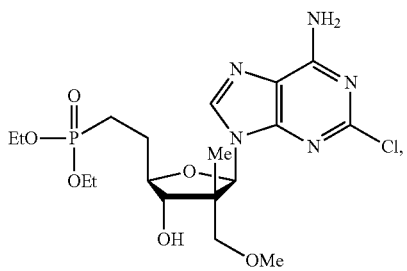

-continued
LCB2122
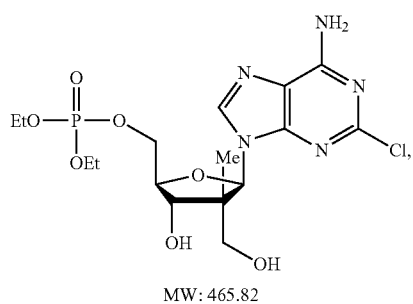
MW: 465.82
LCB2165
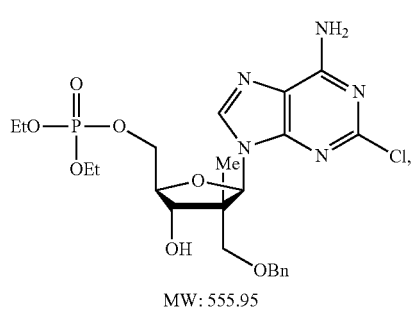
MW: 555.95
LCB2177
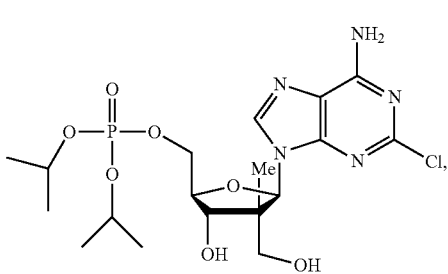
MW: 493.88
LCB2234
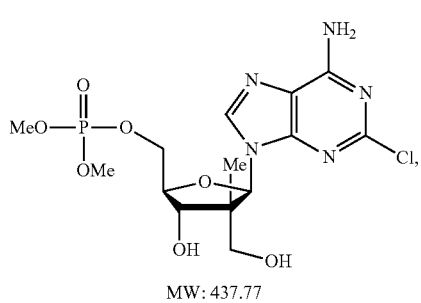
MW: 437.77
LCB2191
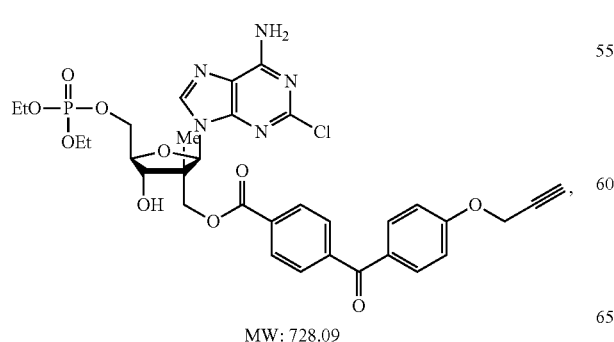
MW: 728.09
-continued
LCB2194
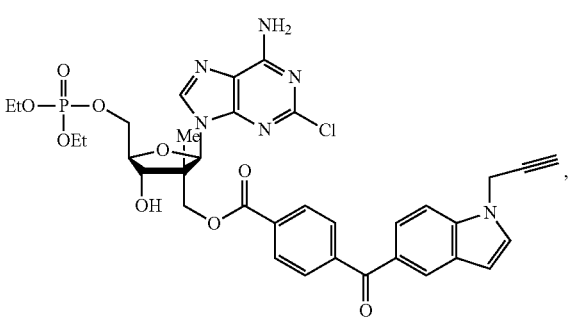
MW: 751.13
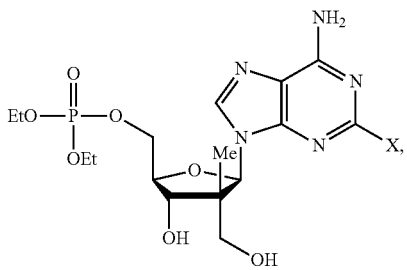
X = F, Br, NH$_2$, N$_3$
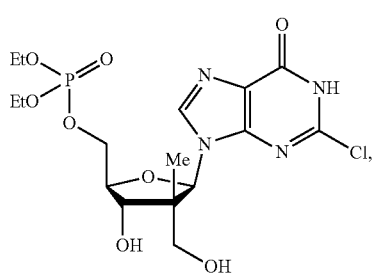
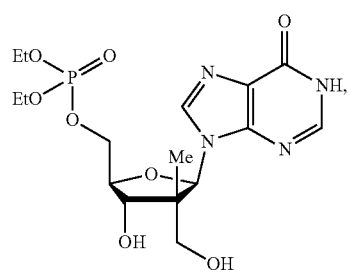
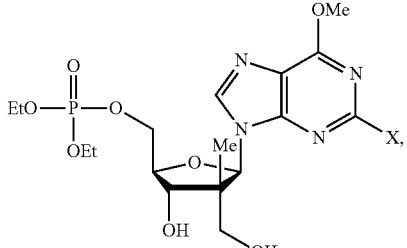
X = Cl, F, Br, NH$_2$, N$_3$

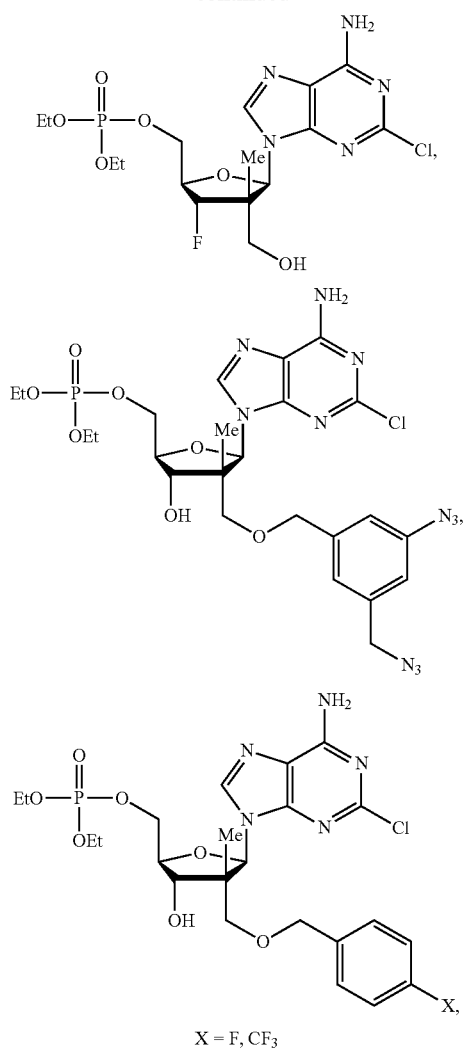
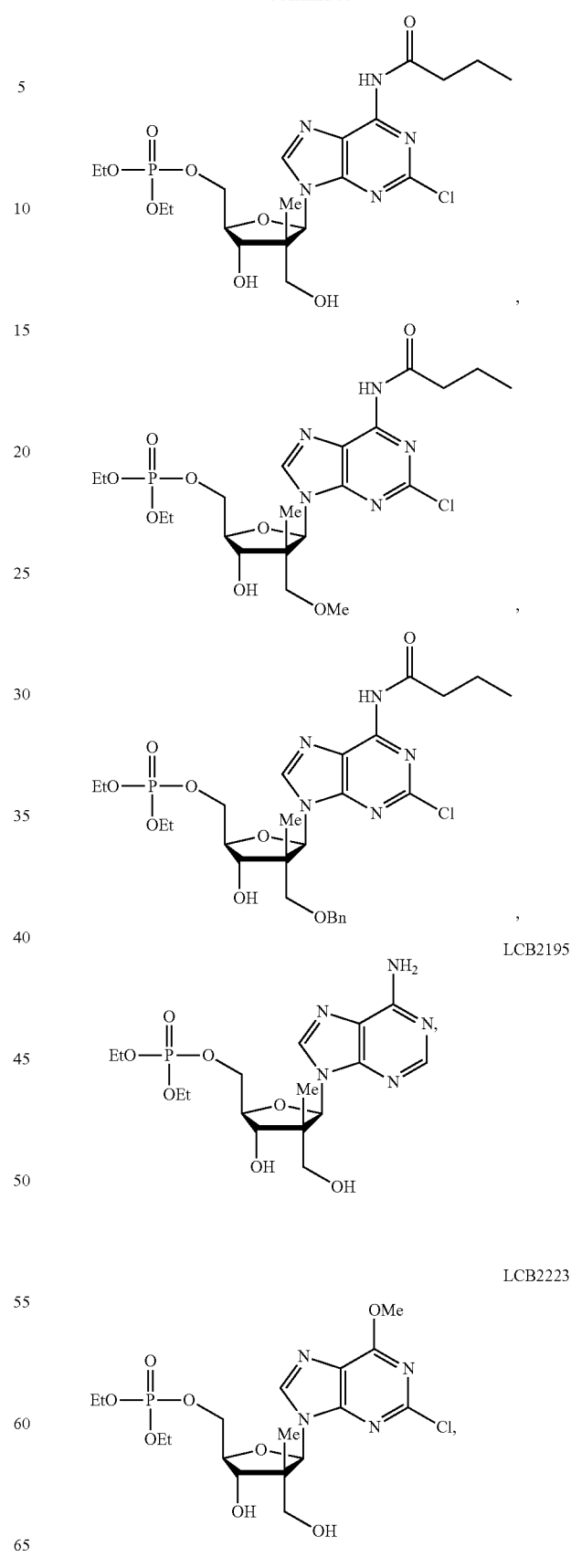

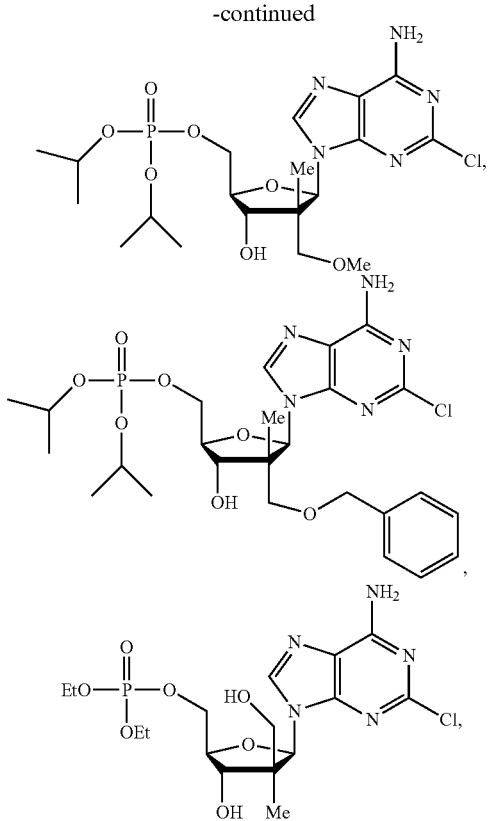
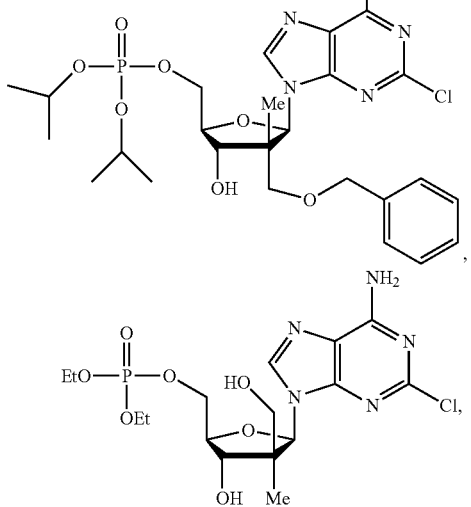
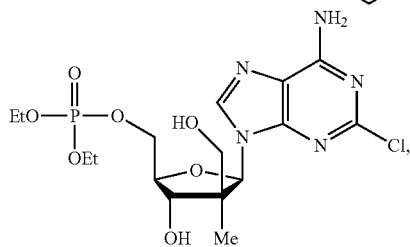
or a pharmaceutically acceptable salt thereof to the subject.
More preferred compounds of the invention include:
LCB2122
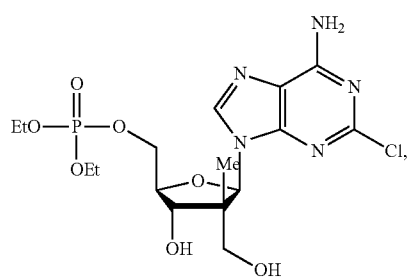
LCB2165
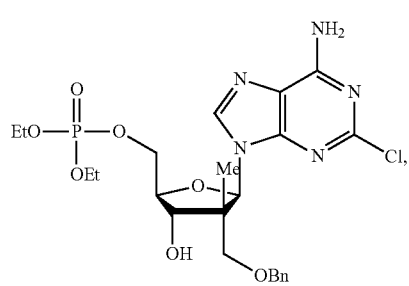
LCB2177
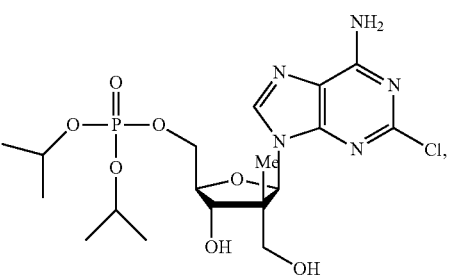
LCB2195
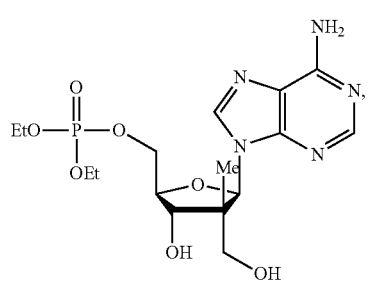
LCB2223
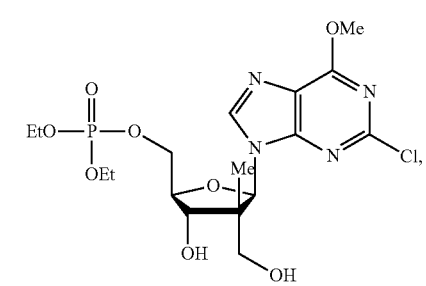
LCB2234
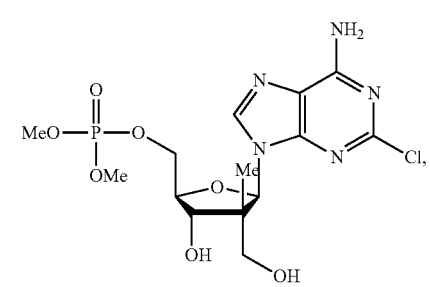
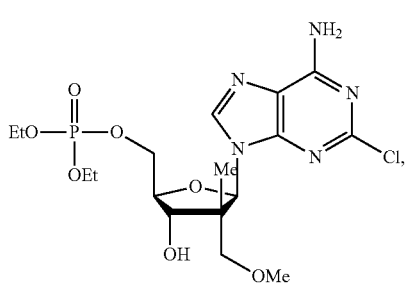

-continued
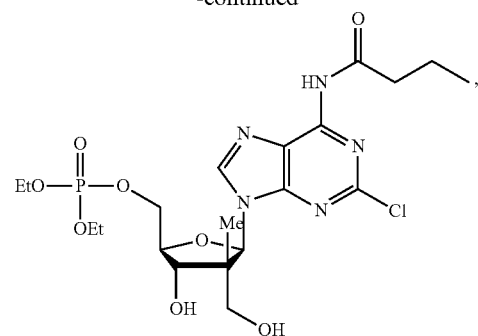
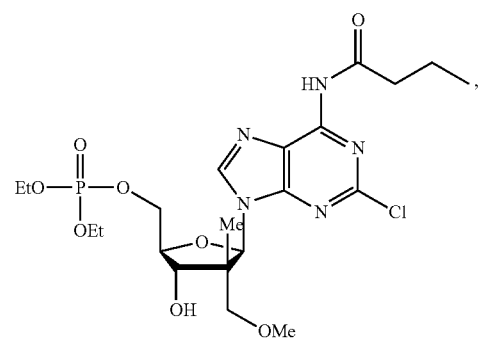
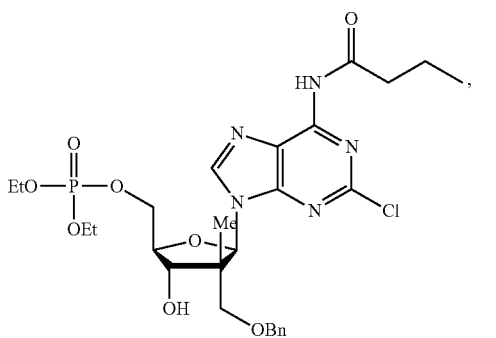, or
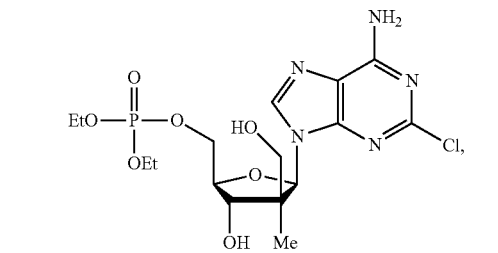
or a pharmaceutically acceptable salt thereof.
Even more preferred compounds of the invention include:
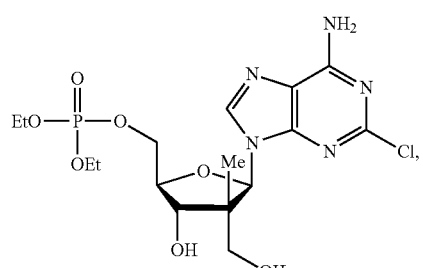
LCB2122
-continued
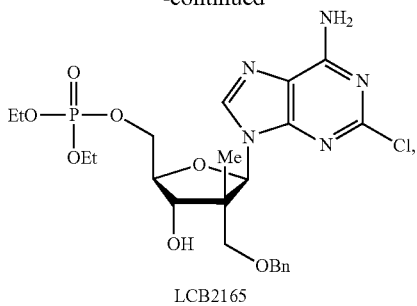
LCB2165
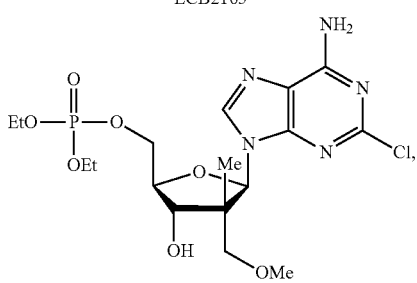
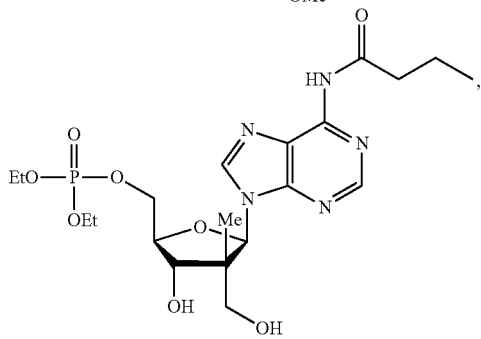
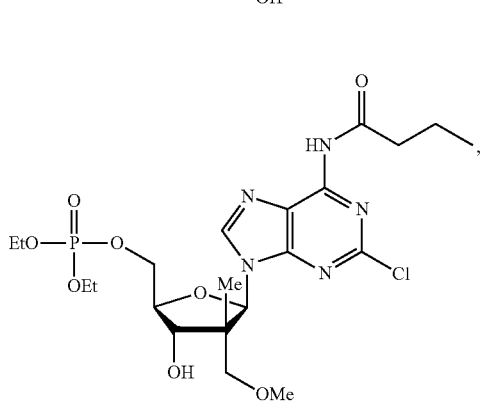
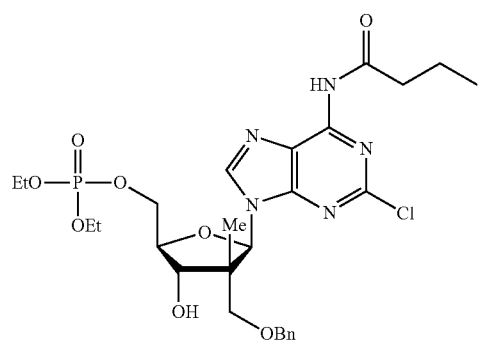

and yet more preferred compounds include:

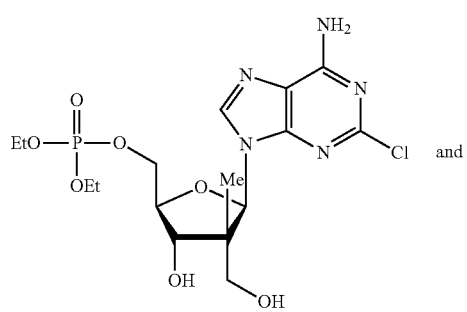

LCB2122

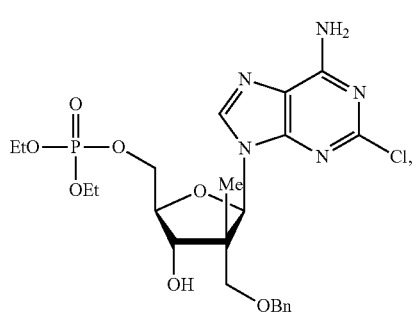

LCB2165

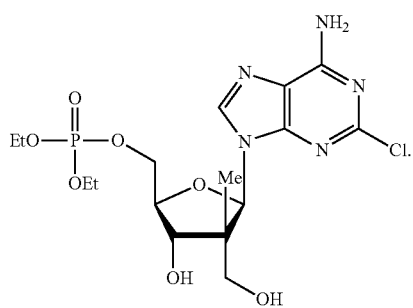

LCB2122

As noted above, "pharmaceutically acceptable salts" of the compounds described herein are included within the scope of the present invention. Such salts may be prepared from pharmaceutically acceptable non-toxic bases including inorganic bases and organic bases. Salts derived from inorganic bases include sodium, potassium, lithium, ammonium, calcium, magnesium, ferrous, zinc, copper, manganous, aluminum, ferric, manganic salts and the like. Particularly preferred are the potassium, sodium, calcium and magnesium salts. Salts derived from pharmaceutically acceptable organic non-toxic bases include salts or primary, secondary, and tertiary amines, substituted amines including naturally occurring substituted amines, cyclic amines and basic ion exchange resin, such as isopropylamine, tri-methylamine, diethanolamine, diethylamine, triethylamine, tripropylamine, ethanolamine, 2-dimethylaminoethanol, 2-diethylamino-ethanol, tometheamine, lysine, arginine, histidine, caffeine, procaine, hydrabamine, choline, imidazole, betaine, ethylenediamine, glucosamine, methylglucamine, theobromine, purines piperazine, N,N-dibenzylethylenediamine, piperidine, N-ethyl-piperidine, morpholine, N-ethyl-morpholine, polyamine resins and the like. "Pharmaceutically acceptable salts" also refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. See, for example, S. M. Berge, et al., "Pharmaceutical Salts," J. Pharm. Sci., 1977; 66:1-19 which is incorporated herein by reference.[12]

Pharmaceutical Compositions

The present invention also relates to pharmaceutical compositions comprising a pharmaceutically acceptable carrier, excipient or diluent and a compound of the invention as defined above or a pharmaceutically acceptable salt thereof.

Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracistemally, or rectally, in the form of solid, semi-solid, lyophilized powder, or liquid dosage forms, such as, for example, tablets, suppositories, pills, soft elastic and hard gelatin capsules, powders, solutions, suspensions, or erosols, or the like, preferably in unit dosage forms suitable for simple administration of precise dosages. In embodiments, administration may preferably be by the oral route.

The compositions of the invention include a conventional pharmaceutical carrier or excipient and a compound of the invention as the/an active agent, and, in addition, may include other medicinal agents, pharmaceutical agents, carriers, adjuvants, etc. In particular, compositions of the invention may be used in combination with anticancer or other agents that are generally administered to a patient being treated for cancer. Adjuvants include preserving, wetting, suspending, sweetening, flavoring, perfuming, emulsifying, and dispensing agents.

Prevention of the action of microorganisms can be ensured by various antibacterial and antifungal agents, for example, parabens, chlorobutanol, phenol, ascorbic acid, and the like. It may also be desirable to include isotonic agents, for example sugars, sodium chloride, and the like. Prolonged absorption of injectable pharmaceutical forms can be brought about using agents delaying absorption, for example, aluminium monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Compositions suitable for parenteral injection may comprise physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms, as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound (s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18$^{th}$ Ed., (Mack Publishing Company, Easton, Pa., 1990)$^{13}$ The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

Use of the Compounds

Cardioprotection

The present invention relates to the use of the above compounds and the above pharmaceutical composition for providing cardioprotection in a subject in need thereof. In other words, the invention relates to a method of providing cardioprotection in a subject in need thereof, the method comprising administering the compound to the subject.

Indeed, as shown in the examples below, the compounds of the invention reduced abnormal cardiomyocyte apoptosis, loss of ejection fraction and/or loss of ventricular wall thickness induced by cardiotoxic anticancer drugs. They also significantly improved the cardiac function in AT1R mice, which are a model for heart failure.

Herein, "cardioprotection" means preserving, reducing deterioration of, and/or improving cardiac function of a heart that has been subjected, is subjected, and/or will be subjected to a cardiac insult. The above subject is thus a subject whose heart has been subjected, is subjected, or will be subjected to one or more of cardiac insults.

The subject is thus at risk of developing or presents a deterioration of cardiac function due, at least in part, to the cardiac insult. In embodiments, the cardiac function may be the ejection fraction of the heart or the cardiac contractility.

Cardioprotection includes preventing, reducing, and/or reversing heart damage due to the cardiac insult. Non-limiting examples of heart damage that can be prevented, reduced or reversed include abnormal cardiomyocyte apoptosis, cardiac remodeling including changes (loss or gain) in heart wall thickness, decrease in ejection fraction especially resulting in inadequate cardiac output, poor organ perfusion, and/or loss of cardiac contractility.

Cardioprotection also includes the prevention and/or treatment of a cardiac dysfunction due, at least in part, to the cardiac insult. Thus, in such embodiments, the above subject is a subject at risk of developing or presenting a cardiac dysfunction due, at least in part, to the cardiac insult. Non-limiting examples of cardiac dysfunctions include chronic conditions such as heart failure, for example congestive heart failure, particularly when drug-induced, as well as acute conditions such as a myocardial infarction.

Non-limiting examples of cardiac insults include:
coronary artery disease and heart attack;
hypertension;
faulty heart valves;
cardiomyopathy;
myocarditis;
congenital heart defects;
diabetes; and
the use of cardiotoxic drugs, particularly anticancer drugs.

Thus, in specific embodiments, cardioprotection include the prevention or reduction of cardiotoxicity associated with the use of a cardiotoxic drug, and/or reversing the cardiotoxic effects thereof. It is contemplated that the compound of the invention, may be used before, during or after a course of treatment with a cardiotoxic drug. Use of the compound of the invention "during" the course of treatment with a cardiotoxic drug include concurrent, subsequent, or alternating administration of both drugs during the course of treatment with the cardiotoxic drug. In such embodiments, it is contemplated that the amount and/or frequency of therapy with such drugs could be increased without a concomitant increase in cardiotoxicity.

Herein, a "cardiotoxic drug" is a drug that causes damage to the heart, and particularly in embodiments to the cardiomyocytes. Non-limiting examples of cardiotoxic drugs include anticancer drugs such as anthracyclines, (including doxorubicin, epirubicin, daunorubicin, idarubicin, and mitoxantrone), monoclonal antibodies (including trastuzumab (TRZ), bevacizumab, cetuximab, brentuximab, ipilimumab, panitumumab, pertuzumab, and rituximab) tyrosine kinase inhibitors (including imatinib, dasatinib, nilotinib, vemurafenib, sorafenib, sunitinib, erlotinib, gefitinib, lapatinib, and pazopanib), proteasome inhibitors (including bortezomib, carfilzomib, tamoxifen, abiraterone, anastrozole, exemestane, letrozole, 5-fluorouracil, capecitabine, cisplatin, cyclophosphamide, and ifosfamide) and antimicrotubule agents (including paclitaxel, nab-paclitaxel, and docetaxel).[3,14] In preferred embodiments, the cardiotoxic drug is doxorubicin or imatinib, preferably doxorubicin.

The present invention also relates to the use of the above compounds and the above pharmaceutical composition for providing in vitro cardioprotection. In other words, the invention relates to a method of providing in vitro cardioprotection, the method comprising administering the compound to the heart. Cardioprotective effects for these molecules could indeed be used in vitro for example to prevent damage caused by ischemia during heart transplantation (cold ischemia reperfusion injury, IRI).[15]

General Synthetic Procedure

Figure 2:
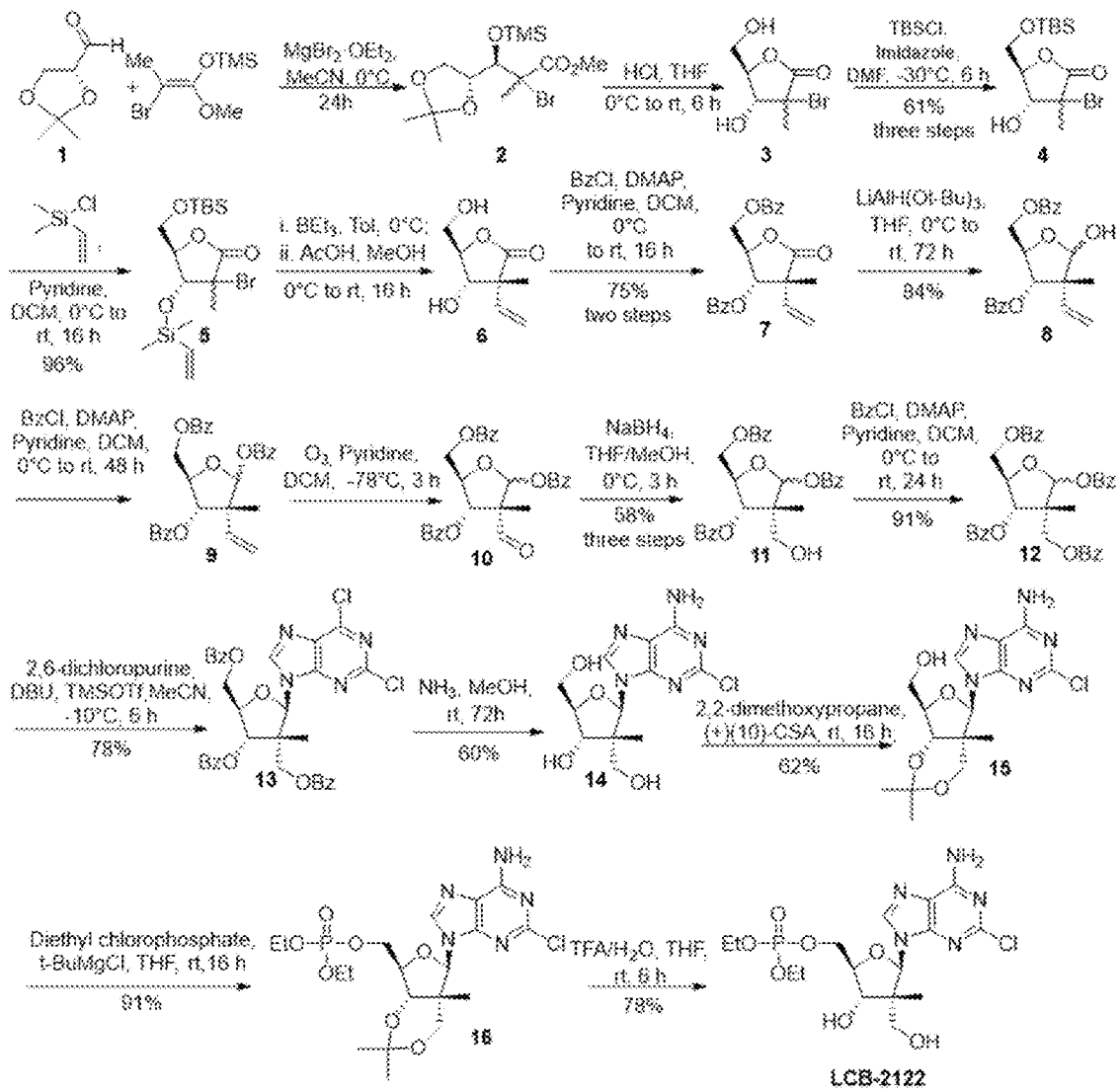
FIG. 2 shows the general synthetic procedure for producing the compounds of the invention.

The compounds of the invention can be prepared using reagents readily available. See the reaction scheme in FIG. 2 as well as the working examples provided below.

Definitions

The use of the terms "a" and "an" and "the" and similar referents in the context of describing the invention (especially in the context of the following claims) are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

Similarly, herein a general chemical structure with various substituents and various radicals enumerated for these substituents is intended to serve as a shorthand method of referring individually to each and every molecule obtained by the combination of any of the radicals for any of the substituents. Each individual molecule is incorporated into the specification as if it were individually recited herein. Further, all subsets of molecules within the general chemical structures are also incorporated into the specification as if they were individually recited herein.

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise claimed.

No language in the specification should be construed as indicating any non-claimed element as essential to the practice of the invention.

Herein, the term "about" has its ordinary meaning. In embodiments, it may mean plus or minus 10% or plus or minus 5% of the numerical value qualified.

Unless otherwise defined, all technical and scientific terms used herein have the same meaning as commonly understood by one of ordinary skill in the art to which this invention belongs.

Herein, the terms "alkyl", "alkylene", "alkenyl", "alkenylene", "alkynyl", "alkynylene" and their derivatives (such as alkoxy, alkyleneoxy, etc.) have their ordinary meaning in the art. For more certainty:

| Term | Definition |
| --- | --- |
| alkyl | monovalent saturated aliphatic hydrocarbon radical of general formula —$C_nH_{2n+1}$ |
| alkenyl | monovalent aliphatic hydrocarbon radical similar to an alkyl, but comprising at least one double bond |
| alkynyl | monovalent aliphatic hydrocarbon radical similar to an alkyl, but comprising at least one triple bond |
| alkyloxy or alkoxy | monovalent radical of formula —O-alkyl |
| alkynyloxy | monovalent radical of formula —O-alkynyl |

It is to be noted that, unless otherwise specified, the hydrocarbon chains of the above groups can be linear or branched. Further, unless otherwise specified, these groups can contain between 1 and 18 carbon atoms, more specifically between 1 and 12 carbon atoms, between 1 and 6 carbon atoms, between 1 and 3 carbon atoms, or contain 1 or 2, preferably 1, or preferably 2 carbon atoms.

Herein, the terms "cycloalkyl", "aryl", "heterocycloalkyl", and "heteroaryl" have their ordinary meaning in the art. For more certainty:

| Term | Definition |
| --- | --- |
| aryl | a monovalent aromatic hydrocarbon radical presenting a delocalized conjugated Π system, most commonly an arrangement of alternating single and double bonds, between carbon atoms arranged in one or more rings, wherein the rings can be fused (i.e. share two ring atoms), for example:<br><br>naphthalene: 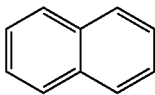<br><br>or linked together through a covalent bond, for example:<br><br>biphenyl: 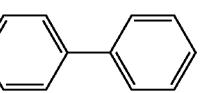<br><br>or linked together through a radical that allow continuation of the delocalized conjugated Π system between the rings (e.g. —C(=O)—, —NRR—), for example:<br><br>benzophenone: 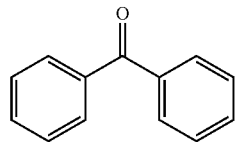 |
| heteroaryl | aryl wherein at least one of the ring carbon atoms is replaced by a heteroatom, such as nitrogen or oxygen. Examples of heteroaryl include:<br><br>indole: 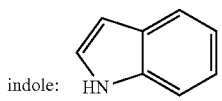<br><br>indole-5-carbonylbenzene: 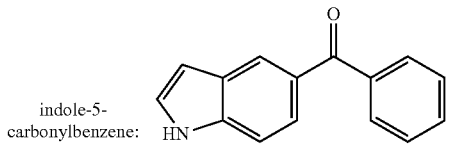 [SMILES: O=C(c1ccccc1)c1ccc2[nH]ccc2c1] |

| Term | Definition |
| --- | --- |
| cycloalkyl | monovalent saturated aliphatic hydrocarbon radical of general formula $C_nH_{2n-1}$, wherein the carbon atoms are arranged in one or more rings (also called cycles). |
| heterocycloalkyl | cycloalkyl wherein at least one of the carbon atoms is replaced by a heteroatom. |

It is to be noted that, unless otherwise specified, the ring(s) of the above groups can each comprise between 4 and 8 ring atoms, preferably between 5 or 6 ring atoms. Also, unless otherwise specified, the above groups may preferably comprise one or more rings, preferably 1 or 2 rings, more preferably a single ring.

Herein, the term "heteroatom" means nitrogen, oxygen, sulfur, phosphorus, preferably nitrogen or oxygen.

Herein, the term "arylalkyl" means an alkyl substituted with an aryl, the alkyl and aryl being as defined above. An arylalkyl groups attaches to the rest of a molecule via its alkyl moiety.

Herein, the term "alkylaryl" means an aryl substituted with an alkyl, the alkyl and aryl being as defined above. An alkylaryl groups attaches to the rest of a molecule via its aryl moiety.

Herein, "halo" refers to halogen atoms, which include fluorine (F), chlorine (Cl), bromine (Br), and iodine (I).

Herein, "azido" refers to a radical of formula $N_3$, i.e. —N=$N^+$=N—, which is in resonance with —$N^-$—$N^+$≡N.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

The present invention is illustrated in further details by the following non-limiting examples.

Example 1—Cardioprotective Activity

In Vitro Experiments

In vitro experiments were carried out to test the direct effect of compounds of the invention LCB2122, LC2165, and LCB2191 on cardiomyocytes.

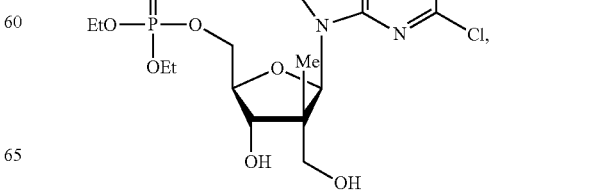

LCB2122

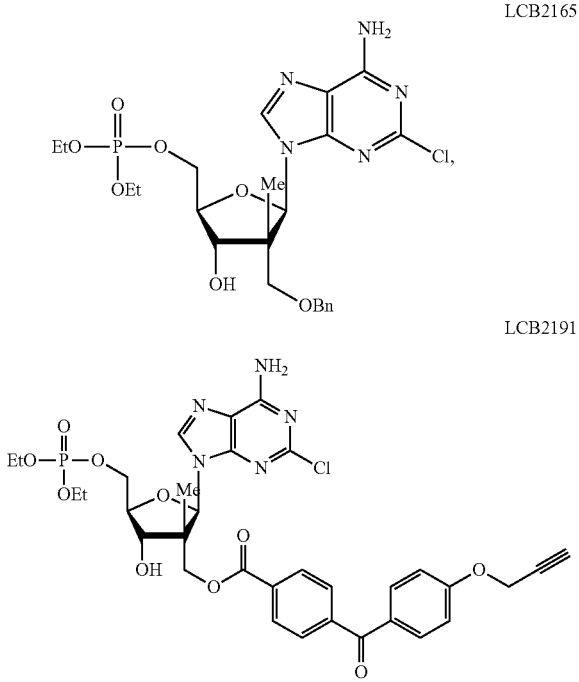

Primary cardiomyocyte monologues covered by serum free media (SF) were treated with DMSO (vehicle), Doxorubicin (DOX) (300 nM), Imatinib (Imat) (5 μM), and/or LCB2122 at varying concentrations (0.1, 0.5, 1.5 at 10 μM) diluted in SF for 3, 6, 18 or 24 hours. The TUNEL assay (Terminal Deoxynucleotidyltransferase mediated dUTP End Labeling) was utilized to detect apoptotic nuclei using an Apop Tag Red in Situ Apoptosis Detection Kit (Millipore, Temecula, Calif.). A Zeis fluorescent microscope was used for image acquisition. Cell counting was done using the Imager® Software.

Figure 3:
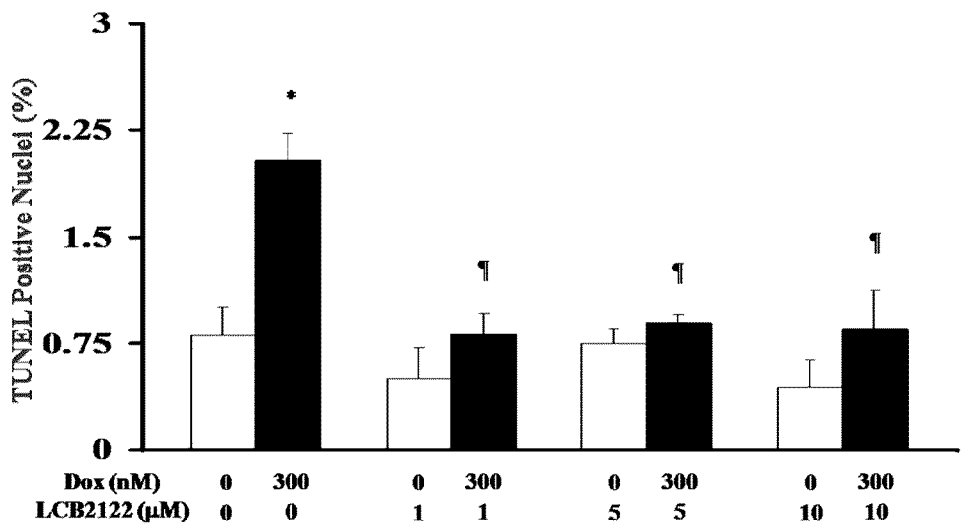
FIG. 3 shows the dose-response for cardiomyocyte monologues treated with Doxorubicin (DOX) (300 nM) and/or with LCB2122 for 6 hours (data shown are the mean±SEM of N=3 per group)
Figure 4:
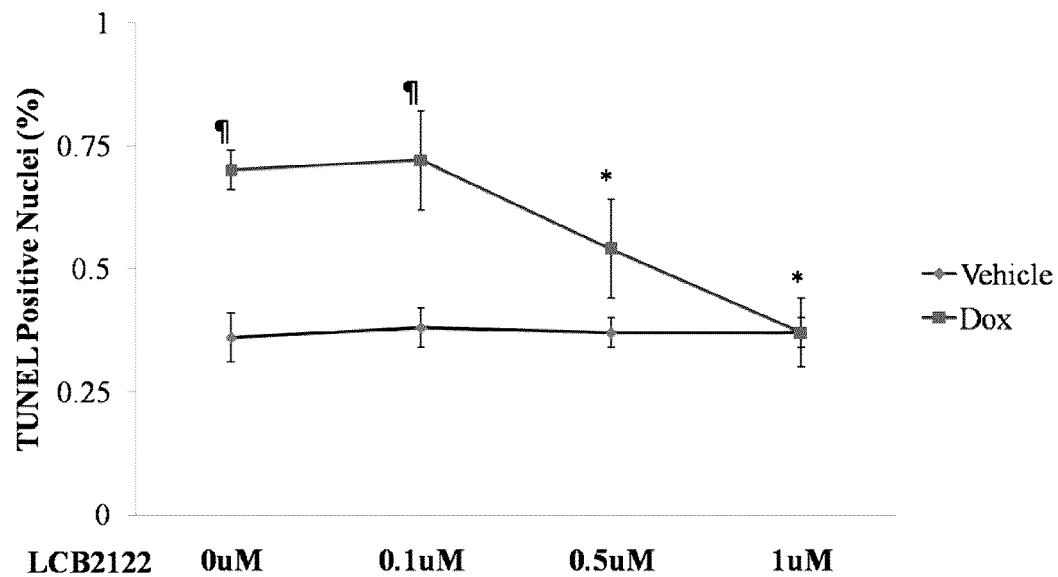
FIG. 4 shows the dose-response for cardiomyocyte monologues treated with Doxorubicin (DOX) (300 nM) and with lower concentrations of LCB2122 or with the vehicle.
Figure 5:
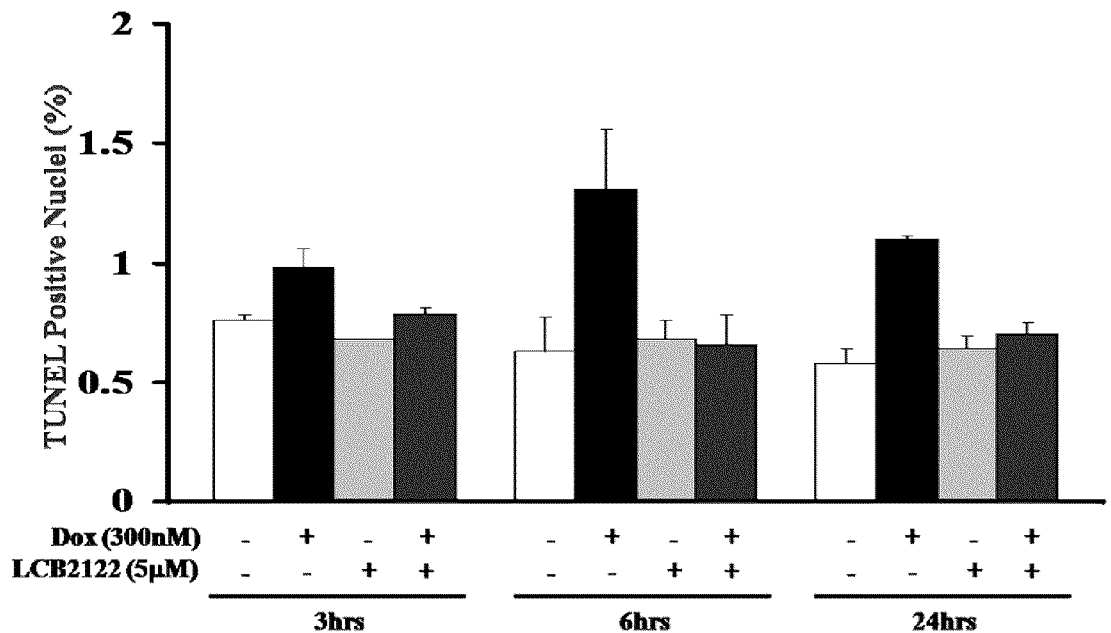
FIG. 5 shows the time course for cardiomyocyte monologues treated with Doxorubicin (DOX) (300 nM) and/or with LCB2122.

As seen in FIGS. 3 and 4, LCB2122 completely prevented DOX-induced apoptotic cell death with an $EC_{50}$ of 500 nM (FIG. 4). LCB2122 did not induce apoptosis in these cells at any time points (FIG. 5). DOX-induced apoptosis was however blocked by LCB2122 at 3, 6 or 24 hours.

Figure 6:
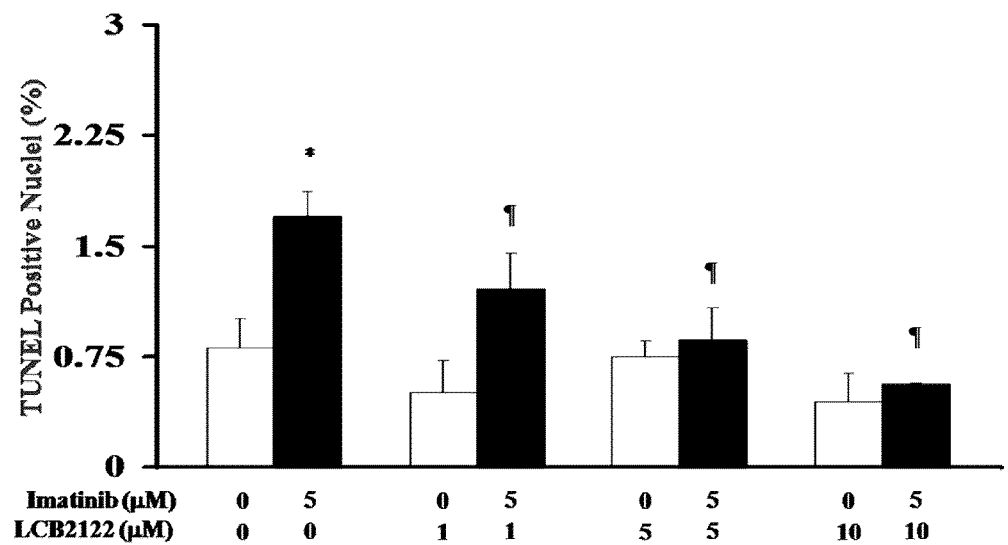
FIG. 6 shows the dose-response for cardiomyocyte monologues treated with Imatinib (Imat) (5 nM) and/or with LCB2122 for 6 hours.

As seen in FIG. 6, the apoptosis induced by Imatinib was also prevented by LCB2122 with an $EC_{50}$ of 5 μM.

The cardioprotective profile of LCB2122, LC2165, LCB2191 and LCB2177 were also investigated. As above, primary cardiomyocytes were treated with 3 μM of Doxorubicin for 6 hours alone or with the above compounds of the invention. The TUNEL assay was utilized to detect apoptotic nuclei. The results are shown in Table 1. LCB2122 showed an $IC_{50}$ of 1 μM in this assay. LCB2165, LCB2191 and LCB2177 were also active with $IC_{50}$'s of 5 μM.

TABLE 1

| Compound | $IC_{50}$ |
|---|---|
| LCB2122 | 1 μM |
| LCB2165 | 5 μM |
| LCB2191 | 5 μM |
| LCB2177 | 5 μM |

Immunofluorescence were performed on cardiomyocytes as previously described,[16] using a sarcomeric alpha-Actinin antibody (1/500).

Figure 7:
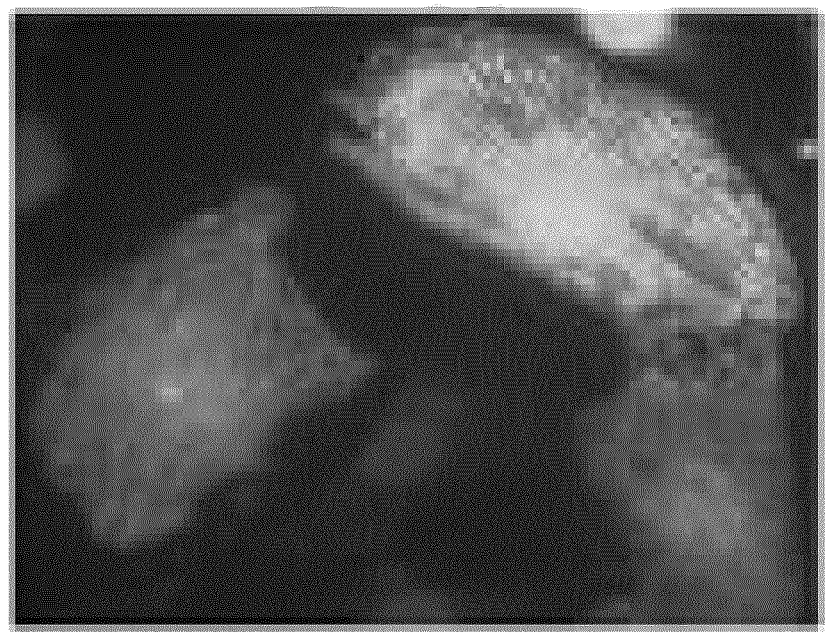
FIG. 7 is a micrograph showing actinin stained cardiomyocytes treated with a) a vehicle (DMSO) or b) with LCB2122.
Figure 7:
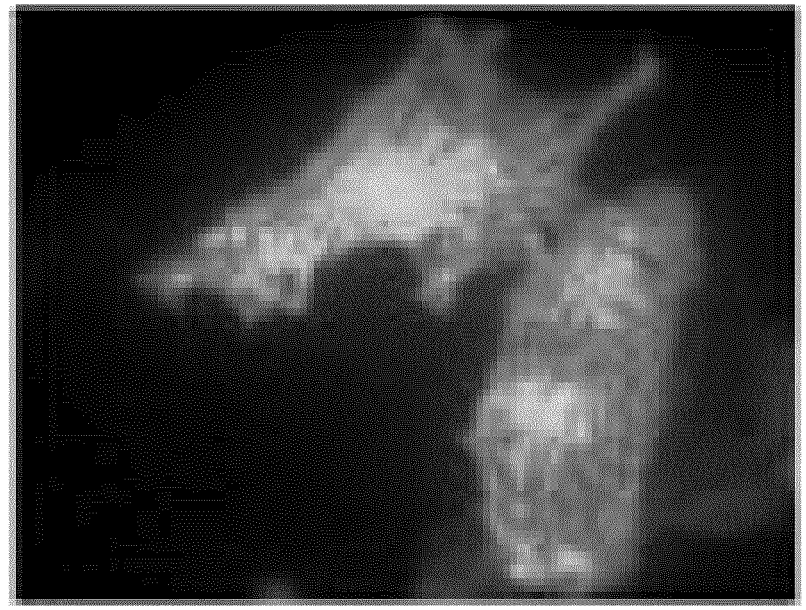

FIG. 7 is a micrograph showing α-actinin immunostaining (straight lines) of 2% PFA-fixed cardiomyocytes treated with a) vehicle (DMSO) or b) LCB2122 (5 uM) for six hours. Note how LCB2122 does not alter cytoskeletal organization or cell size. White spots mark the nuclei.

Figure 8:
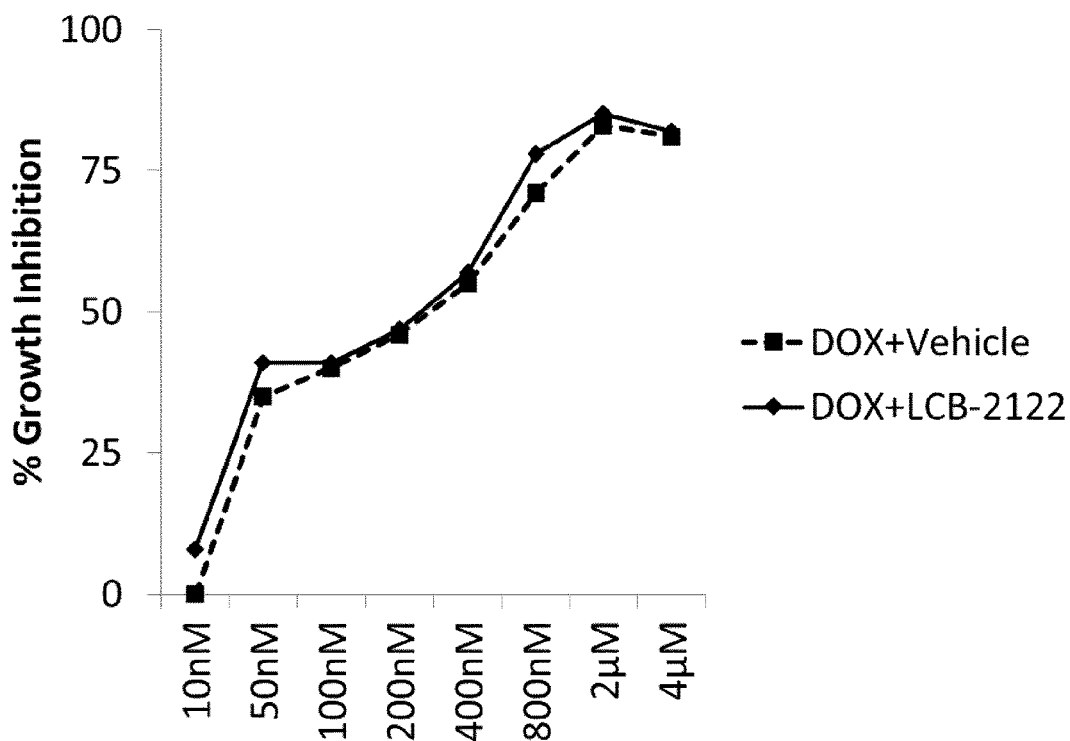
FIG. 8 is a plot representing the percent growth inhibition as measured by Cell Titer Glo assays done on HepG2 cells treated with varying concentrations of DOX+/−LCB-2122 (1 µM)

Furthermore, it was observed (FIG. 8) that LCB2122 did not affect the antiproliferative effect of DOX. Indeed, the $IC_{50}$ of DOX in HepG2 human cancer cell line was identical in the absence or presence of LCB2122. FIG. 8 is a plot representing the percent growth inhibition as measured by Cell Titer Glo assays done on HepG2 cells treated with varying concentrations of DOX+/−LCB-2122 (1 M). With up to 4 μM, LCB2122 had no effect on HepG2 sensitivity to DOX.

In Vivo Experiments

Mice were handled in accordance with institutional guidelines for animal care. Experiments were approved by the institutional Animal Care Committees and the investigation conforms with the Guide for the Care and Use of Laboratory Animals published by the US National Institutes of Health (NIH Publication N. 85-23, revised 1985). Doxorubicin treatment was a single ip injection of 5 or 15 mg/kg as previously described by Aries et al.[6] ALZET micro-osmotic pumps (Model 1002, 0.25 μl/hr, 14 days) were filled with DMSO, Ang II (0.5 μgKg/day) LCB2122 (2.0 or 2.8 μg/Kg/day) diluted in normal saline and inserted subcutaneously in mice for two weeks. M-mode echocardiography was performed using Visual-Sonics VEVO 2100 system and 30-MHz linear array transducer, on lightly anesthetized mice using 20% isofluorane, 80 ml/min of 100% oxygen, as described by Aries et al. and echocardiographic indices were calculated as described by Yang et al.[17] Heart failure was defined as EF<45%.

Figure 9:
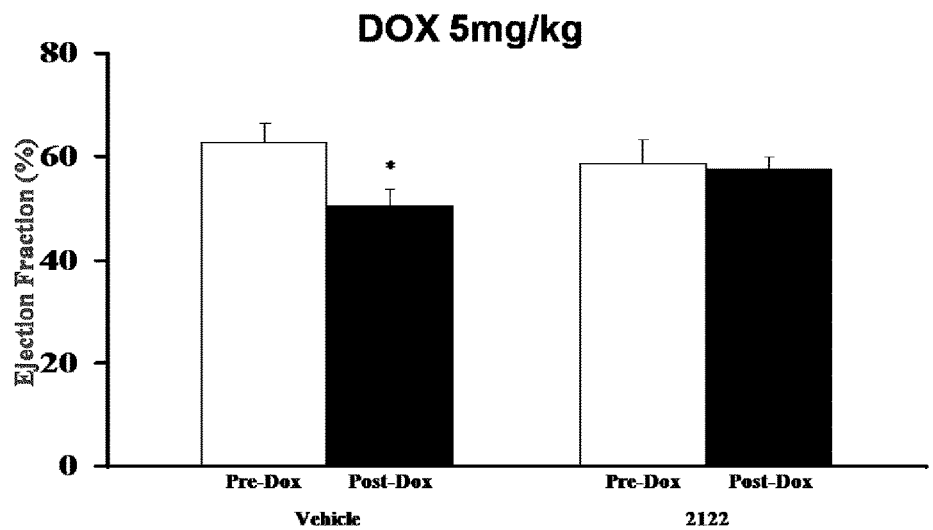
FIG. 9 shows the ejection fraction measured by in vivo echocardiography before and after treatment with DOX (5 mg/kg) in the presence and absence of LCB2122.

As seen in FIG. 9, the ejection fraction (EF, %), which is an index of cardiac contractility, was decreased significantly in mice after two weeks of DOX ip injection. LCB2122 treated mice (micropump for two weeks) were protected against DOX-induced toxicity (i.e. EF decrease).

Figure 10:
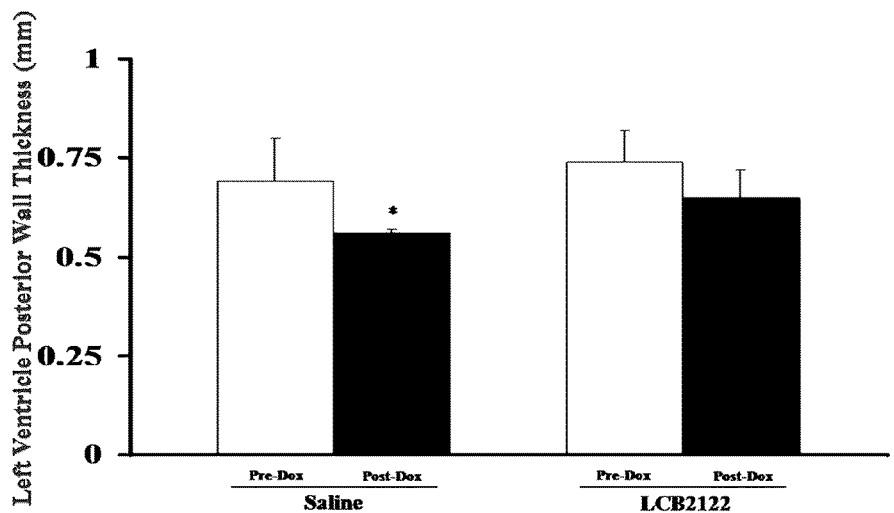
FIG. 10 shows the left ventricle posterior wall thickness measured by in vivo echocardiography before and after treatment with DOX (5 mg/kg) in the presence and absence of LCB2122.

DOX (5 μg/kg) induced also a loss of ventricular wall thickness in wild type mice. The LCB2122 treated mice were protected against this DOX-induced wall thickness (see FIG. 10).

Figure 11:
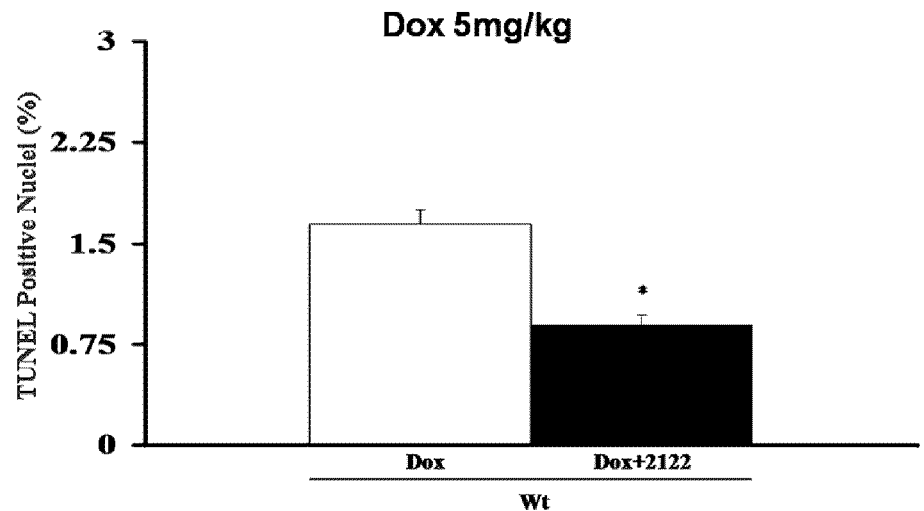
FIG. 11 shows the % of apoptotic nuclei as measured by TUNEL positive assay after treatment with DOX (5 mg/kg) in the presence and absence of LCB2122.

After these 2 weeks, heart cardiomyocytes were also tested by TUNEL assay (on heart sections). As seen in FIG. 11, a significant decrease of apoptotic cardiomyocytes was noted when LCB2122 was used.

Transgenic mice overexpressing the human angiotensin II type 1 receptor[7] (AT1R) under the control of the mouse α-myosin heavy chain were generated. These mice are a model of human HF. Cardiomyocyte specific overexpression induced in basal conditions overtime, morphologic changes that mimic those observed during the development of cardiac hypertrophy in humans. In order words, these mice develop age-dependent HF. These mice indeed displayed remodeling with increased expression of ventricular clinical natriuretic factor and interstitial collagen deposition and died prematurely of heart failure.

The effect of LCB2122 was studied in AT1R mice and wild-type mice.

Figure 12:
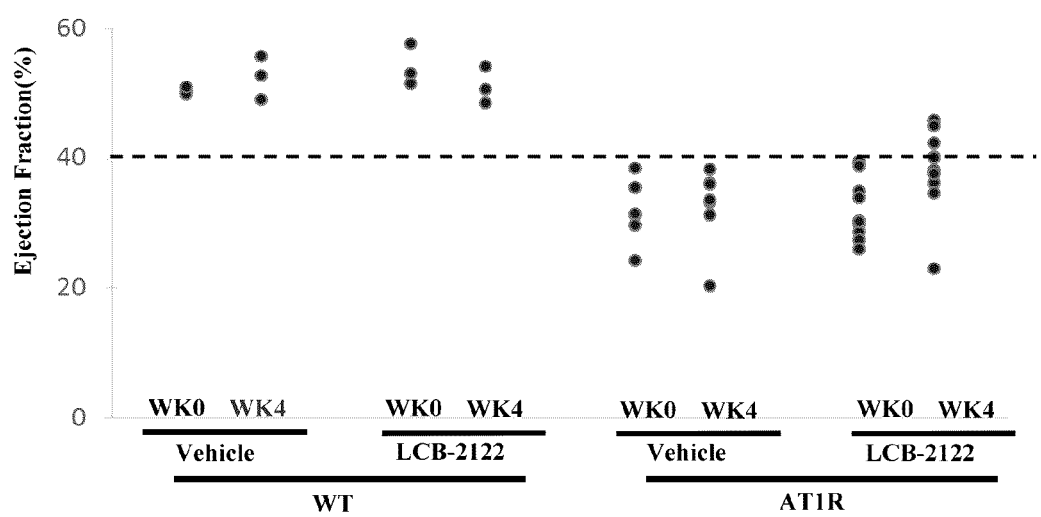
FIG. 12 shows the ejection fraction as measured by echocardiography in vehicle and LCB2122 treated (2.0 µg/kg/day for 4 weeks wild-type (WT) or AT1R mice (HFmice) pre- and 4 weeks post-minipumps (The data shown are individual values of each model of human HF)

As seen in FIG. 12, echocardiography shows changes in heart ejection fraction (EF %) for 60 day old AT1R transgenic mice. All AT1R mice had EF % less than 40%, similar to HF patients in human. Ejection fraction (%) was decreased significantly in mice after 4 weeks in 60 day AT1R mice. LCB2122 treated AT1R mice (2.0 μg/kg/day for 4 weeks) had their cardiac functions improved as opposed to untreated mice. In fact, the data shows a significant improvement of the cardiac function for AT1R mice treated for 4 weeks (2.0 µg/kg per day) with LCB2122. LCB2122 did not alter cardiac function of normal mice. The data shown are the individual values of each mouse at weeks 0 and 4. All WT mice had normal EF % independent of LCB2122 treatment throughout the study. All AT1R mice were in HF prior to any treatment. The EF % of AT1R mice+LCB2122 continued to go up, and after four weeks 55% of these mice had an EF % equal and above 40%.

Figure 13:
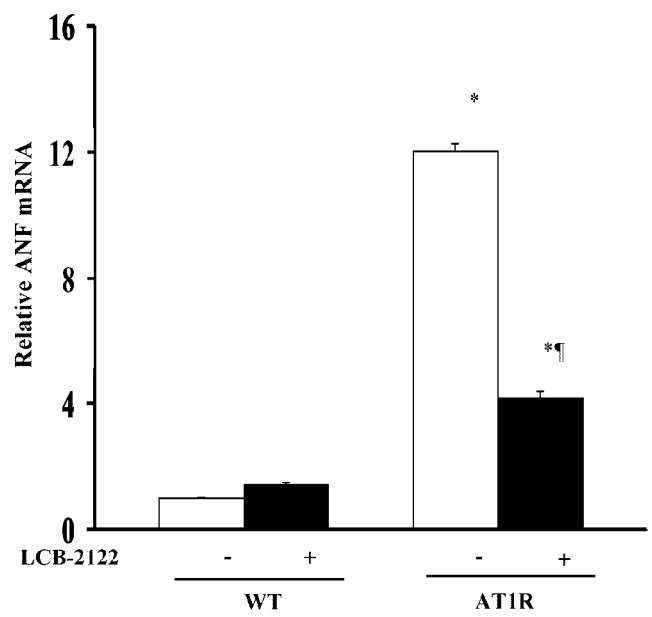
FIG. 13 shows a) ANF transcript changes using QPCR analysis on reverse transcribed RNA from vehicle and LCB2122 (2.0 µg/Kg/day, 4 weeks) treated WT and AT1R mice ventricles and b) quantification of an ANF ELISA assay done on blood plasma samples from vehicle and LCB2122 (2.0 µg/Kg/day, 4 weeks) treated WT and AT1R mice ventricles.
Figure 13:
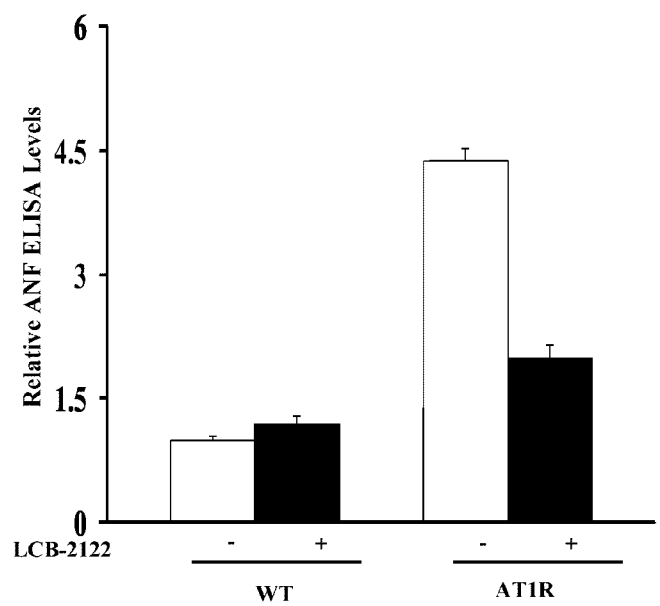

As seen in FIG. 13, both levels of atrial natriuretic factor (ANF) in RNA or ANF measured by ELISA were attenuated after the treatment as opposed to the ventricles of treated mice.

Indeed, FIG. 13a) shows ANF transcript changes using QPCR analysis on reverse transcribed RNA from vehicle and LCB2122 (2.0 µg/Kg/day, 4 weeks) treated WT and AT1R mice ventricles. The massive ANF upregulation seen in AT1R mice usually indicative of cardiac stress is attenuated in LCB2122 treated AT1R mice.

FIG. 13b) quantification of an ANF ELISA assay done on blood plasma samples from vehicle and LCB2122 (2.0 µg/Kg/day, 4 weeks) treated WT and AT1R mice ventricles. Once again, the increase in ANF plasma levels was attenuated in the LCB2122 treated AT1R mice.

Example 2—Chemical Synthesis

Example 2.1—Intermediate Compound

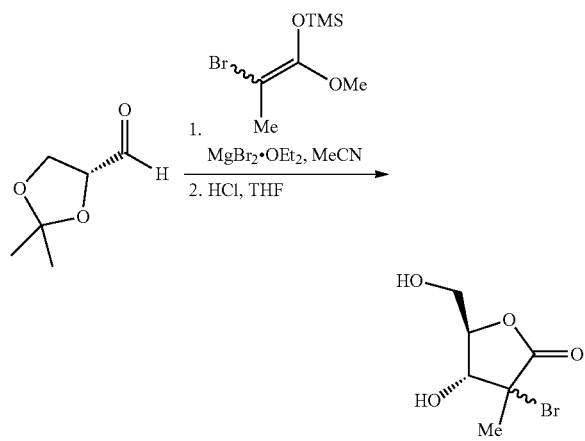

(4R,5R)-3-bromo-4-hydroxy-5-(hydroxymethyl)-3-methyldihydrofuran-2(3H)-one. To a solution of precooled glyceraldehyde (24 g, 185 mmol) in dry acetonitrile (710 mL) at −10° C. under Ar, MgBr$_2$.OEt$_2$ (37 g, 142 mmol) is added. After 15 minutes, all the solids were in solution and neat enolate (50.7 g, 142 mmol) precooled at −20° C. was added via cannula during 10 minutes. The mixture was stirred for 23 h at 0° C. and quenched by addition of 200 mL ice-H$_2$O at 0° C. The mixture was diluted with ethyl acetate, washed 2×200 mL with distilled water, the organic phase was dried over MgSO$_4$, and concentrated to produce clear brown oil (50.7 g), which was used for the next step. HCl conc (10 mL, 121.8 mmol) was added dropwise to a solution of aldol adducts (50.7 g, 137 mmol) in THF (275 mL) at 0° C. and open atmosphere for 20 minutes. After 50 minutes, the reaction was warmed to room temperature. After 5 h, the reaction mixture was concentrated producing dark green oil that was passed trough a bed of SiO$_2$ (200 mL) and rinsed with a mixture of CH$_2$Cl$_2$/EtOAc 50%. The dark brown solid was washed with hexanes, then twice with Hexanes/EtOAc (95:5) producing a clear brown solid (19 g, 59% over 2 steps).

A: major lactone (3,4-anti). $^1$H NMR (500 MHz, Methanol-d$_4$) δ 4.18 (ddd, J=8.4, 4.2, 2.1 Hz, 1H), 3.97 (dd, J=13.0, 2.1 Hz, 1H), 3.82 (d, J=8.4 Hz, 1H), 3.73 (dd, J=13.0, 4.2 Hz, 1H), 1.86 (s, 3H). $^{13}$C NMR (126 MHz, CD$_3$OD) δ 174.4, 84.3, 74.3, 62.4, 59.9, 24.4.

B: minor lactone (3,4-anti). $^1$H NMR (500 MHz, Methanol-d$_4$) δ 4.64 (d, J=6.3 Hz, 1H), 4.24 (ddd, J=6.3, 5.0, 3.2 Hz, 1H), 3.96-3.84 (m, 2H), 3.82-3.75 (m, 1H), 1.82 (s, 3H). $^{13}$C NMR (126 MHz, CD$_3$OD) δ 175.7, 86.1, 78.0, 61.4, 58.8, 22.3. R$_f$=0.05 (30% ethyl acetate in hexanes).

Example 2.2—Intermediate Compound

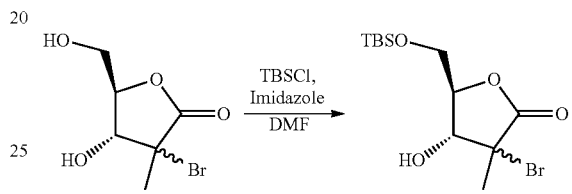

(4R,5R)-3-bromo-5-(((tert-butyldimethylsilyl)oxy)methyl)-4-hydroxy-3-methyldihydrofuran-2(3H)-one. TBSCl (12.7 g, 84.4 mmol) was added to a mixture of lactones (19 g, 84.4 mmol), and imidazole (23 g, 337.7 mmol) in dry DMF (420 mL) under Ar at −40° C. The reaction was followed by TLC, and after 5 h, 0.06 equiv of TBSCl (0.77 g, 5.10 mmol) was added. After 7 h in total, the reaction mixture was diluted with ethyl acetate (800 mL), washed sequentially with citric acid (0.1 M, 400 mL), distilled water, brine, dried over MgSO$_4$ and concentrated to produce a brown oil (27 g, 94% yield). R$_f$=0.37 (30% ethyl acetate in hexanes); IR (neat) 3457, 2952, 2931, 2855, 1771, 1256, 1132 cm$^{-1}$; Formula C$_{12}$H$_{23}$BrO$_4$Si; MW 339.2981; For major diastereomer from 3,4-anti aldol adduct: $^1$H NMR (500 MHz, CDCl$_3$) δ 4.13 (dt, J=8.1, 2.8 Hz, 1H), 4.01 (dd, J=12.1, 2.5 Hz, 1H), 3.94-3.83 (m, 2H), 1.94 (s, 3H), 0.95-0.82 (m, 9H), 0.08 (d, J=7.8 Hz, 6H); $^{13}$C NMR (125 MHz, CDCl$_3$) δ 171.5, 82.7, 74.0, 62.3, 60.0, 26.0, 24.4, 18.4, −5.2, −5.3; For minor diastereomer from 3,4-anti aldol adduct: $^1$H NMR (500 MHz, CDCl$_3$) δ 4.82 (dd, J=6.6, 2.5 Hz, 1H), 4.22 (ddd, J=6.4, 5.3, 3.8 Hz, 1H), 4.00-3.88 (m, 2H), 1.88 (s, 3H), 0.90 (s, 9H), 0.10 (s, 6H); $^{13}$C NMR (125 MHz, CDCl$_3$) δ 173.1, 83.0, 78.1, 61.7, 57.0, 26.0, 22.1, 18.4, −5.2, −5.2; MS (ESI) m/z 361.0 (M+Na$^+$, 100); HRMS calcd for [M+H$^+$]: 339.0627, found: 339.0621; calcd for [M+Na$^+$]: 361.0447, found: 361.0442.

Example 2.3—Intermediate Compound

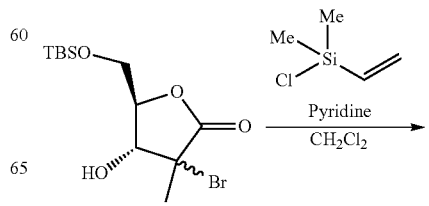

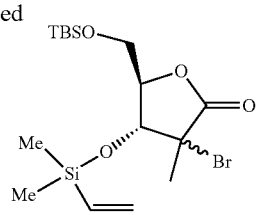

(4R,5R)-3-bromo-5-(((tert-butyldimethylsilyl)oxy)
methyl)-4-((dimethyl(vinyl)silyl)oxy)-3-methyldihydro-
furan-2(3H)-one. Chlorodimethylvinylsilane (11.2 g, 13.2
mL, 92.9 mmol) was added to a mixture of TBS-lactones
(84.43 mmol) and dry pyridine (16.6 g, 17.0 mL, 211.1
mmol) in dry $CH_2Cl_2$ (422 mL) under Ar at 0° C. The
mixture was brought to room temperature slowly and after
23 h, 0.05 equiv of chlorodimethylvinylsilane was added
(509 mg, 0.6 mL). After 28 h in total, the reaction mixture
was concentrated, suspended in a mixture of 20% ethyl
acetate in hexanes, passed trough a pad of $SiO_2$, rinsed with
500 mL of (20% ethyl acetate in hexanes), and concentrated
to produce yellow oil (32.5 g, 96% yield). $R_f$=0.6 (30% ethyl
acetate in hexanes); IR (neat) 2952, 2925, 2850, 1787, 1256,
1138 $cm^{-1}$; Formula $C_{16}H_{31}BrO_4Si_2$; MW 423.4899;

For major diastereomer from 3,4-anti aldol adduct:
$^1H$ NMR (500 MHz, $CDCl_3$) δ 6.20-6.05 (m, 2H), 5.86
(dd, J=19.4, 4.6 Hz, 1H), 4.16 (dt, J=7.9, 1.9 Hz, 1H),
4.03-3.98 (m, 2H), 3.78 (dd, J=12.6, 2.0 Hz, 1H), 1.84 (s,
3H), 0.87 (s, 9H), 0.28 (s, 6H), 0.07 (d, J=10.4 Hz, 6H); $^{13}C$
NMR (125 MHz, $CDCl_3$) δ 172.4, 136.4, 134.9, 82.5, 73.4,
60.1, 58.6, 25.9, 24.9, 18.3, −1.3, −1.5, −5.2, −5.3;

For minor diastereomer from 3,4-anti aldol adduct:
$^1H$ NMR (500 MHz, $CDCl_3$) δ 6.20-6.05 (m, 2H), 5.83
(dd, J=19.9, 4.1 Hz, 1H), 4.84 (d, J=6.0 Hz, 1H), 4.13 (ddd,
J=6.0, 4.0, 3.2 Hz, 1H), 3.96 (dd, J=12.0, 3.8 Hz, 1H), 3.81
(dd, J=11.9, 3.6 Hz, 1H), 1.80 (s, 3H), 0.90 (s, 9H),
0.30-0.28 (m, 6H), 0.08 (s, 6H); $^{13}C$ NMR (125 MHz,
$CDCl_3$) δ 173.5, 136.3, 134.7, 84.2, 77.4, 60.5, 57.5, 25.9,
22.5, 18.4, −1.4, −1.5, −5.2, −5.3; MS (ESI) m/z 447.1
(M+Na+, 100), 445.1 (M+Na+, 100), 431.2 (83); HRMS
calcd for [M+H+]: 423.1023, found: 423.1009; [M+$NH_4^+$]:
440.1288, found: 440.1274; calcd for [M+Na+]: 445.0842,
found: 445.0831.

Example 2.4—Intermediate Compound

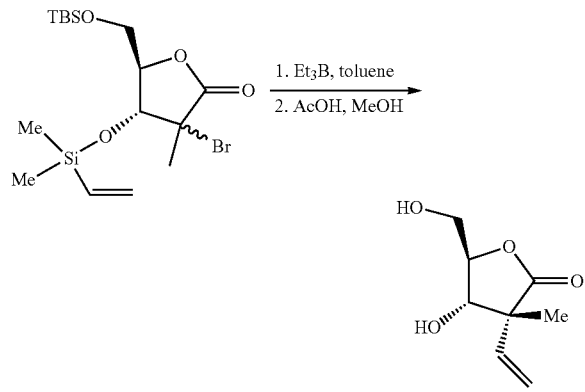

(3R,4S,5R)-4-hydroxy-5-(hydroxymethyl)-3-methyl-3-
vinyldihydrofuran-2(3H)-one. $Et_3B$ (76.8 mL, 76.8 mmol, 1
M in hexanes) was added via syringe with a rate of 15.4
mL/h to a solution of lactones (32.5 g, 76.8 mmol) in dry
toluene (153 mL) at 0° C., open atmosphere and vigorous
stirring. After 7 h, 0.1 equiv of $BEt_3$ (7.7 mL, 7.7 mmol, 1
M in hexanes) was added. The reaction was quenched after
8 h in total by consecutive addition of methanol (153 mL)
and acetic acid (9.2 g, 8.8 mL, 153.6 mmol) at 0° C. and
allowed to reach room temperature slowly (overnight). The
reaction mixture was concentrated after 17 h and the result-
ing brown oil was washed with hexanes (×1), passed through
a pad of $SiO_2$ and rinsed with a gradient of 50% ethyl
acetate/hexanes to 100% ethyl acetate. The brown solid was
dissolved in $CH_2Cl_2$ and the title product was formed as a
white solid (7.08 g, 53% yield, only one diastereomer). The
remaining brown oil (8.52 g) was purified by silica gel
column chromatography (30% ethyl acetate in hexanes) to
yield the title product as a beige solid (4.68 g, 35%, 5:1
mixture of diastereomers). Overall yield 88% and ca. 14:1
(3,4-anti:3,4-syn). $R_f$=0.09 (30% ethyl acetate in hexanes);
IR (neat) $cm^{-1}$ 3419, 2936, 1766, 1100, 1041; Formula
$C_8H_{12}O_4$; MW 172.1785; $^1H$ NMR (500 MHz, $CDCl_3$) δ
6.07-5.92 (m, 1H), 5.27 (d, J=10.7 Hz, 1H), 5.13 (d, J=17.7
Hz, 1H), 4.12-4.03 (m, 2H), 3.97-3.89 (m, 1H), 3.68 (dd,
J=13.1, 3.8 Hz, 1H), 1.32 (s, 3H); $^{13}C$ NMR (125 MHz,
$CD_3OD$) δ 178.9, 135.7, 117.0, 83.6, 75.8, 60.8, 52.7, 20.9;
MS (ESI) m/z 195.1 (M+Na+, 100), 173.1 (M+H+, 7);
HRMS calcd for [M+H+]: 173.0814, found: 173.0804; calcd
for [M+Na+]: 195.0633, found: 195.0625; $[α]_D$+53 (c 1.4,
$CH_3OH$).

Example 2.5—Intermediate Compound

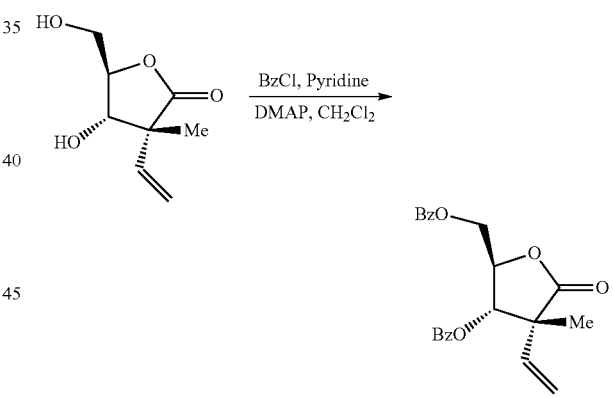

((2R,3S,4R)-3-(benzoyloxy)-4-methyl-5-oxo-4-vinyltet-
rahydrofuran-2-yl)methylbenzoate. Benzoyl chloride (26.9
g, 22.2 mL, 191.14 mmol) was added slowly to a mixture of
lactone (10.97 g, 63.71 mmol), DMAP (778 mg, 6.371
mmol) and pyridine (30.2 g, 31 mL, 382.3 mmol) under Ar
at 0° C. The mixture was slowly brought to room tempera-
ture. After 21 h, the reaction was cooled to 0° C., diethyl-
amine (3.8 g, 4.2 mL, 63.7 mmol) was added dropwise,
allowed to reach room temperature and stirred overnight.
The mixture was concentrated, suspended in a mixture of
30% ethyl acetate in hexanes, passed trough a pad of $SiO_2$,
and concentrated to yield a yellow oil (23.12 g, 95% yield).
$R_f$=0.49 (30% ethyl acetate in hexanes); IR (neat) 1787,
1723, 1449, 1267, 1111 $cm^{-1}$; Formula $C_{22}H_{20}O_6$; MW
380.3906; $^1H$ NMR (500 MHz, $CDCl_3$) δ 8.03-7.98 (m, 4H),
7.62 (td, J=7.4, 1.3 Hz, 1H), 7.55 (td, J=7.4, 1.4 Hz, 1H),
7.47 (td, J=7.9, 7.5, 1.4 Hz, 2H), 7.41-7.37 (m, 2H), 5.95

(dd, J=17.5, 10.7 Hz, 1H), 5.55 (d, J=7.5 Hz, 1H), 5.44-5.30 (m, 2H), 4.76-4.71 (m, 2H), 4.59-4.54 (m, 1H), 1.56 (s, 3H); $^{13}$C NMR (125 MHz, CDCl$_3$) δ 175.1, 166.0, 165.5, 134.0, 133.5, 132.6, 130.0, 129.9, 128.8, 128.6, 118.5, 77.2, 63.2, 51.0, 21.6; $^1$H NMR (500 MHz, C$_6$D$_6$) δ 8.04 (dd, J=8.3, 1.3 Hz, 2H), 7.96 (dd, J=8.3, 1.3 Hz, 2H), 7.17-7.12 (m, 1H), 7.11-7.06 (m, 1H), 7.07-7.01 (m, 2H), 6.99 (ddd, J=8.2, 6.8, 1.2 Hz, 2H), 5.68 (dd, J=17.5, 10.7 Hz, 1H), 5.40 (d, J=7.6 Hz, 1H), 5.23 (d, J=17.5 Hz, 1H), 5.03 (d, J=10.7 Hz, 1H), 4.46 (dd, J=12.1, 3.5 Hz, 1H), 4.38 (ddd, J=7.7, 5.8, 3.4 Hz, 1H), 4.30 (dd, J=12.1, 5.8 Hz, 1H), 1.38 (s, 3H); $^{13}$C NMR (125 MHz, C$_6$D$_6$) δ 174.4, 165.8, 165.3, 133.7, 133.3, 133.2, 130.1, 130.0, 128.8, 128.6, 117.9, 77.4, 77.4, 77.1, 63.6, 50.9, 21.5; MS (ESI) m/z 403.1 (M+Na$^+$, 50), 398.2 (M+NH$_4^+$, 100), 381.1 (M+H$^+$, 46); HRMS calcd for [M+H$^+$]: 381.1338, found: 381.1317; calcd for [M+NH$_4^+$]: 398.1604, found: 398.1580; calcd for [M+Na$^+$]: 403.1158, found: 403.1137; [α]$_D$+90 (c 2.0, CH$_2$Cl$_2$).

Example 2.6—Intermediate Compound

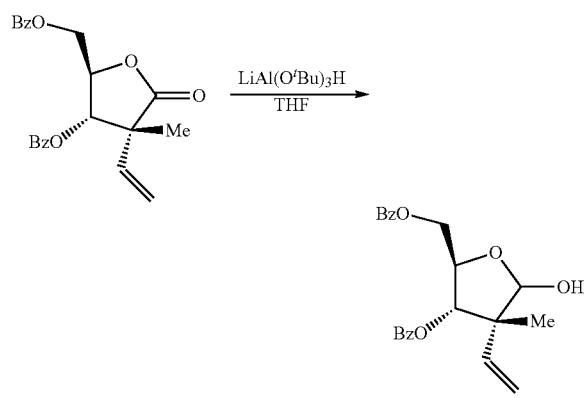

((2R,3S,4R)-3-(benzoyloxy)-5-hydroxy-4-methyl-4-vinyltetrahydrofuran-2-yl)methylbenzoate. LiAlH(OtBu)$_3$ (45 mL, 45 mmol, 1 M in THF) was added dropwise at 0° C. to solution of lactone (13.16 g, 34.60 mmol) in THF (115 mL) under Ar. The mixture was slowly brought to room temperature. After stirring for 72 hours, Na$_2$SO$_4$·10H$_2$O (16.7 g, 51.90 mmol) was added at room temperature and stirred vigorously for 1 h. The mixture was concentrated, suspended in ethyl acetate and filtered through a pad of celite-SiO$_2$, washed with ethyl acetate and concentrated to yield a clear yellow oil (11.08 g, 83%, mixture of anomers in a 1.4:1 ratio of anomers). R$_f$=0.3 (×2, 20% ethyl acetate in hexanes); IR (neat) 3457, 1723, 1449, 1272, 1116 cm$^{-1}$; Formula C$_{22}$H$_{22}$O$_6$; MW 382.4065; For mixture of both anomers: $^1$H NMR (500 MHz, CDCl$_3$) δ 8.08-7.98 (m, 9H), 7.60-7.35 (m, 17H), 6.29 (dd, J=17.8, 11.0 Hz, 1H), 6.10 (dd, J=17.6, 11.0 Hz, 1.4H), 5.57 (d, J=6.8 Hz, 1.4H), 5.36-5.15 (m, 8H), 4.77-4.57 (m, 7H), 4.42 (td, J=6.5, 4.2 Hz, 1.4H), 3.20 (dd, J=3.3, 1.7 Hz, 1H), 2.99 (dd, J=5.3, 1.4 Hz, 1H), 1.35 (x 2 s, 7H); $^{13}$C NMR (125 MHz, CDCl$_3$) δ 166.6, 166.1, 138.1, 135.3, 133.5, 133.2, 133.1, 129.9, 128.6, 128.6, 128.5, 128.5, 117.8, 116.3, 104.4, 103.4, 81.1, 80.8, 79.9, 79.6, 66.4, 65.0, 52.6, 51.8, 20.8, 16.9; MS (ESI) m/z 405.1 (M+Na$^+$, 43), 400.2 (M+NH$_4^+$, 24), 365.1 (100); HRMS calcd for [M+NH$_4^+$]: 400.1760, found: 400.1755; calcd for [M+Na$^+$]: 405.1314, found: 405.1311.

Example 2.7—Intermediate Compound

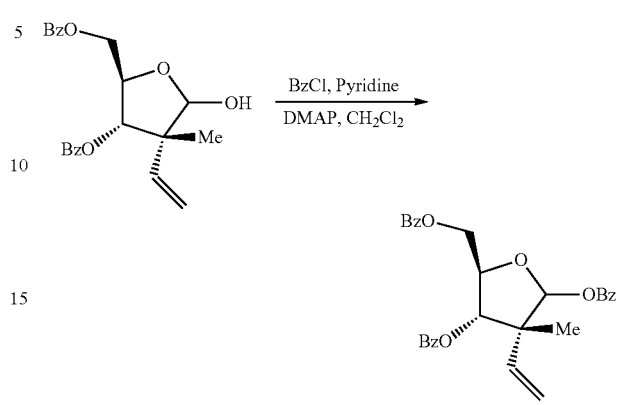

(3R,4S,5R)-5-((benzyloxy)methyl)-3-methyl-3-vinyltetrahydrofuran-2,4-diyl dibenzoate. Benzoyl chloride (7.7 g, 6.4 mL, 55.0 mmol) was added slowly to a mixture of lactols (16.18 g, 42.31 mmol), DMAP (517 mg, 4.23 mmol) and pyridine (10.0 g, 10.3 mL, 126.93 mmol) under Ar at 0° C. The mixture was slowly brought to room temperature. After 21 h, 0.2 equiv of benzoyl chloride (1.19 g, 0.98 mL, 8.46 mmol) was added. After 42 h, the reaction was cooled to 0° C., diethylamine (1.3 g, 1.4 mL, 21.16 mmol) was added dropwise (yellow precipitate formed). The mixture was concentrated, suspended in a mixture 20% ethyl acetate in hexanes, passed through a pad of SiO$_2$, concentrated to yield a clear yellow oil (18.06 g, 88% yield, 3:1 mixture of anomers) and another fraction containing 3 diastereomers (1.73 g in a 16:27:57 ratio, the first 2 coming from 3,4-anti aldol adduct and the last from 3,4-syn aldol adduct). R$_f$=0.4 (30% ethyl acetate in hexanes); IR (neat) 3065, 2968, 1728, 1599, 1449, 1272 cm$^{-1}$; Formula C$_{29}$H$_{26}$O$_7$; MW 486.5125; For major anomer: $^1$H NMR (500 MHz, CDCl$_3$) δ 8.14 (dd, J=8.4, 1.4 Hz, 1H), 8.05 (ddd, J=13.9, 8.3, 1.4 Hz, 4H), 7.93-7.90 (m, 2H), 7.59 (ddt, J=7.7, 6.1, 1.6 Hz, 2H), 7.47-7.41 (m, 4H), 7.20 (t, J=7.8 Hz, 2H), 6.43 (s, 1H), 6.18 (dd, J=17.5, 11.2 Hz, 1H), 5.81 (d, J=7.6 Hz, 1H), 5.45 (s, 1H), 5.42 (d, J=7.3 Hz, 1H), 4.70 (dd, J=11.5, 4.1 Hz, 1H), 4.60 (ddd, J=7.5, 5.6, 4.1 Hz, 1H), 4.54 (dd, J=11.6, 5.6 Hz, 1H), 1.42 (s, 3H); $^{13}$C NMR (125 MHz, CDCl$_3$) δ 166.2, 165.8, 165.2, 136.5, 133.6, 133.5, 133.0, 130.6, 129.9, 129.9, 129.7, 129.3, 128.9, 128.6, 128.6, 128.2, 117.2, 102.1, 79.6, 78.5, 65.1, 52.1, 17.5; MS (ESI) m/z 509.2 (M+Na$^+$, 84), 504.2 (M+NH$_4^+$, 100), 365.1 (61); HRMS calcd for [M+NH$_4^+$]: 504.2022, found: 504.2021; calcd for [M+Na$^+$]: 509.1576, found: 509.1576.

Example 2.8—Intermediate Compound

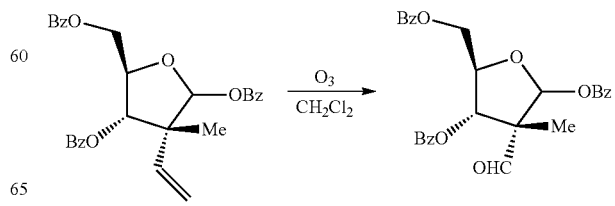

(3S,4S,5R)-5-((benzoyloxy)methyl)-3-formyl-3-methyl-tetrahydrofuran-2,4-diyl dibenzoate. O₃ was flowed into a mixture of benzoylated lactols (18.06 g, 37.12 mmol) in CH₂Cl₂ (150 mL) and pyridine (8.8 g, 9.0 mL, 111.36 mmol) at −78° C. After 5.5 h, the excess O₃ was removed under vacuum, a balloon with N₂ was attached, Et₃N (3.7 g, 5.2 mL, 37.12 mmol) was added, and allowed to reach room temperature. The mixture was concentrated, diluted with ethyl acetate, washed (×1) with citric acid [0.1 M], (×1) NaHCO₃ saturated solution, and dried over MgSO₄ to yield the title compound as a mixture of anomers in a 4:1 ratio (clear oil, 16.9 g, 93%). $R_f$=0.15 (20% ethyl acetate in hexanes); IR (neat) 1728, 1599, 1449, 1267 cm$^{-1}$; Formula C₂₈H₂₄O₈; MW 488.4854; ¹H NMR (500 MHz, CDCl₃) δ 10.06 (s, 1H), 9.97 (s, 4H), 8.08-7.23 (m, aromatics), 6.70 (s, 4H), 6.54 (s, 1H), 5.88 (d, J=6.7 Hz, 4H), 5.48 (d, J=3.7 Hz, 1H), 4.87-4.56 (m, 15H), 1.50 (s, 3H), 1.48 (s, 12H); ¹³C NMR (125 MHz, CDCl₃) δ 198.2, 197.5, 166.0, 165.8, 165.5, 165.4, 164.6, 164.6, 133.8, 133.8, 133.6, 133.6, 133.1, 132.9, 132.8, 129.7, 129.7, 129.7, 129.7, 129.6, 129.6, 129.6, 129.5, 129.5, 129.4, 129.4, 129.2, 129.0, 128.7, 128.6, 128.6, 128.5, 128.5, 128.4, 128.4, 128.3, 128.3, 128.2, 128.1, 128.0, 101.7, 98.5, 84.7, 80.8, 80.1, 79.2, 64.7, 63.7, 60.3, 58.1, 17.9, 13.3; MS (ESI) m/z 511.1 (M+Na⁺, 100); HRMS calcd for [M+NH₄⁺]: 506.1815, found: 506.1800; calcd for [M+Na⁺]: 511.1369, found: 511.1362.

Example 2.9—Intermediate Compound

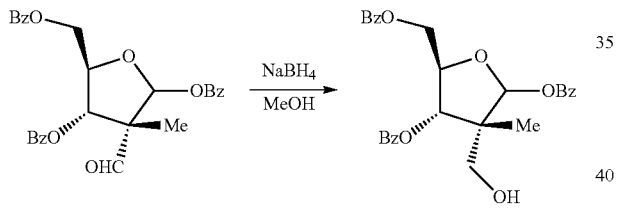

(3R,4S,5R)-5-((benzoyloxy)methyl)-3-(hydroxymethyl)-3-methyltetrahydrofuran-2,4-diyldibenzoate. NaBH₄ (1.34 g, 34.64 mmol) was slowly added in portions to a mixture of aldehydes (16.92 g, 34.64 mmol) in THF/MeOH (1:2) (345 mL) under Ar at 0° C. After 2 h, the reaction was quenched at 0° C. by addition of 20 mL of distilled water and stirred at room temperature for 40 minutes. The mixture was concentrated, suspended in ethyl acetate, and washed with distilled water. The aqueous phase was back extracted with ethyl acetate (×3), the organics were mixed and dried over MgSO₄, concentrated and purified by silica gel column chromatography (30% ethyl acetate in hexanes) to yield the title compound as a white solid (12.26 g, 72%, mixture of anomers 1.6:1). $R_f$=0.2 (30% ethyl acetate in hexanes); IR (neat) 3483, 3070, 2947, 1723, 1599, 1449, 1272 cm$^{-1}$; Formula C₂₈H₂₆O₈; MW 490.5012; For major anomer: ¹H NMR (500 MHz, CDCl₃) δ 8.08 (dd, J=8.0, 1.4 Hz, 2H), 7.99-7.94 (m, 4H), 7.61-7.54 (m, 2H), 7.50 (t, J=7.6 Hz, 1H), 7.45 (t, J=7.7 Hz, 2H), 7.38 (t, J=7.7 Hz, 2H), 7.28 (t, J=8.0 Hz, 2H), 6.59 (s, 1H), 4.62-4.51 (m, 5H), 4.42 (dd, J=8.0, 5.5 Hz, 1H), 4.37 (dt, J=8.1, 4.2 Hz, 1H), 1.35 (s, 3H); ¹³C NMR (125 MHz, CDCl₃) δ 167.0, 166.8, 165.4, 133.5, 133.4, 133.3, 129.9, 129.9, 129.8, 128.7, 128.7, 128.5, 100.7, 82.4, 77.9, 65.6, 65.2, 49.9, 16.4; MS (ESI) m/z 508.2 (M+NH₄⁺, 98), 369.1 (100); HRMS calcd for [M+NH₄⁺]: 508.1971, found: 508.1970; calcd for [M+Na⁺]: 513.1525, found: 513.1518.

For mixture of anomers: ¹H NMR (500 MHz, CDCl₃) δ 8.11-7.32 (m, 19H), 7.28 (t, J=7.9 Hz, 1H), 7.22 (t, J=7.8 Hz, 1H), 6.60 (d, J=4.8 Hz, 1H), 5.79 (d, J=6.4 Hz, 0.6H), 4.72-4.31 (m, 8H), 4.02 (d, J=11.3 Hz, 0.6H), 3.95-3.91 (m, 1H), 1.35 (5H); ¹³C NMR (125 MHz, CDCl₃) δ 167.0, 166.8, 166.3, 165.9, 165.5, 165.4, 133.8, 133.6, 133.5, 133.4, 133.3, 133.1, 129.9, 129.9, 129.8, 129.8, 129.8, 129.8, 129.7, 129.7, 129.6, 128.8, 128.7, 128.7, 128.6, 128.5, 128.4, 128.3, 101.4, 100.7, 82.4, 80.8, 79.1, 77.6, 65.6, 65.6, 65.2, 64.7, 51.4, 49.8, 16.4, 16.2.

Example 2.10—Intermediate Compound

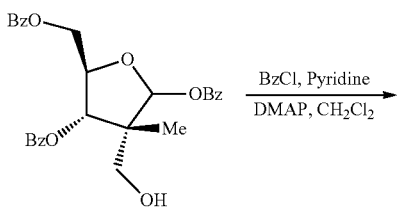

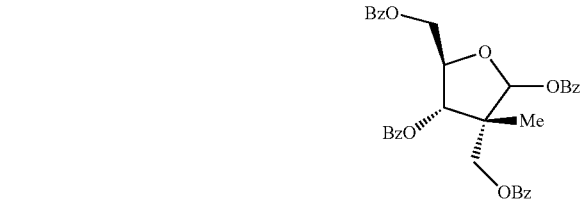

(3R,4S,5R)-3,5-bis((benzoyloxy)methyl)-3-methyltetra-hydrofuran-2,4-diyl dibenzoate. Benzoyl chloride (6.6 g, 5.4 mL, 46.89 mmol) was added slowly to a mixture of alcohols (11.5 g, 23.44 mmol), DMAP (286 mg, 2.34 mmol) and pyridine (7.4 g, 7.6 mL, 93.78 mmol) under Ar at 0° C. The mixture was slowly brought to room temperature. After 21 h, the reaction was cooled to 0° C., diethylamine (1.41 g, 1.57 mL, 23.44 mmol) was added dropwise and stirred for 4 h at rt. The mixture was concentrated, suspended in a mixture of 20% ethyl acetate in hexane, passed through a pad of SiO₂, and concentrated to yield a white foam (12.73 g, 91%, mixture of anomers with an 8:1 ratio). $R_f$=0.38 (30% ethyl acetate in hexanes); IR (neat) 1728, 1449, 1261, 1106 cm$^{-1}$; Formula C₃₅H₃₀O₉; MW 594.6073; For major anomer: ¹H NMR (500 MHz, CDCl₃) δ 8.11-8.00 (m, 6H), 7.96-7.88 (m, 2H), 7.63-7.52 (m, 3H), 7.44 (td, J=7.8, 4.5 Hz, 7H), 7.23 (t, J=7.7 Hz, 2H), 6.72 (s, 1H), 5.90 (d, J=6.6 Hz, 1H), 4.75-4.52 (m, 5H), 1.47 (s, 3H); ¹³C NMR (125 MHz, CDCl₃) δ 166.4, 166.2, 165.8, 165.3, 133.9, 133.7, 133.5, 133.1, 130.0, 130.0, 130.0, 129.8, 129.8, 129.8, 128.8, 128.7, 128.3, 101.0, 80.7, 78.6, 65.7, 65.5, 50.3, 16.7; MS (ESI) m/z 1211.4 (100), 617.2 (M+Na⁺, 75), 612.2 (M+NH₄⁺, 63), 473.2 (66); HRMS calcd for [M+NH₄⁺]: 612.2234, found: 612.2234; calcd for [M+Na⁺]: 617.1788, found: 617.1789.

Example 2.11—Intermediate Compound

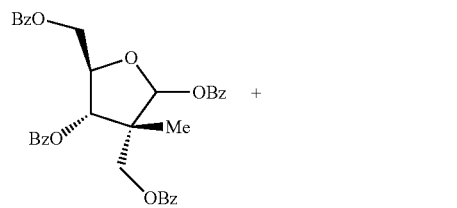

+

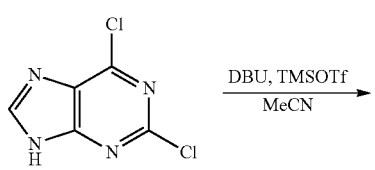

DBU, TMSOTf
————————→
MeCN

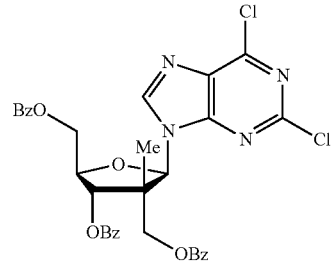

((2R,3S,4R,5R)-3-(benzoyloxy)-5-(2,6-dichloro-9H-purin-9-yl)-4-methyltetrahydrofuran-2,4-diyl)bis(methylene) dibenzoate. DBU (3.67 mL, 3.66 g, 24.06 mmol) was added to a mixture of benzoylated sugar (4.77 g, 8.02 mmol), and 2,6-dichloropurine (1.67 g, 8.82 mmol) in dry acetonitrile (32 mL), under $N_2$ at −10° C. The mixture was stirred and then TMSOTf (5.9 mL, 7.26 g, 32.08 mmol) was added dropwise over 2 minutes. After 3 h, the reaction was quenched by addition of saturated solution of $NaHCO_3$ (5 mL) at −10° C., suspended in $CH_2Cl_2$, and washed ×1 with a saturated solution of $NaHCO_3$. The aqueous phase was extracted with $CH_2Cl_2$ (×3), the organics were washed ×2 with citric acid [0.1 M], dried over $MgSO_4$, and concentrated to produce beige foam. $^1$H-NMR of the crude showed a 8:1 ratio of β:α anomers. The crude was fractionated by silica gel column chromatography (20% ethyl acetate in hexanes) to provide a white solid as a 10:1 mixture of β:α anomers (3.96 g, 74%). $R_f$=0.32 (30% ethyl acetate in hexanes); IR (neat) $v_{max}$ 3065, 2968, 1723, 1589, 1551, 1267 cm$^{-1}$; Formula $C_{33}H_{26}Cl_2N_4O_7$; MW 661.4881; $^1$H NMR (500 MHz, CDCl$_3$) δ 8.44 (s, 1H), 8.05 (ddd, J=8.0, 6.4, 1.4 Hz, 4H), 7.76-7.71 (m, 2H), 7.65-7.51 (m, 3H), 7.45 (dt, J=10.7, 7.8 Hz, 4H), 7.37 (t, J=7.8 Hz, 2H), 6.62 (s, 1H), 5.70 (d, J=5.9 Hz, 1H), 4.93-4.84 (m, 3H), 4.63 (q, J=4.8 Hz, 1H), 4.52 (d, J=11.6 Hz, 1H), 1.23 (s, 3H); $^{13}$C NMR (125 MHz, CDCl$_3$) δ 166.3, 165.8, 165.7, 153.4, 152.5, 152.2, 144.1, 134.2, 133.6, 133.6, 130.9, 130.0, 129.8, 129.5, 129.3, 129.1, 128.9, 128.8, 128.6, 128.4, 89.1, 81.1, 78.2, 65.7, 63.5, 49.3, 17.6; MS (ESI) m/z 683.1 (M+Na$^+$, 100), 360.3 (86), 226.9 (24); HRMS calcd for $C_{33}H_{26}Cl_2N_4NaO_7$ [M+Na$^+$]:683.1091 found: 683.1066.

Example 2.12—Intermediate Compound

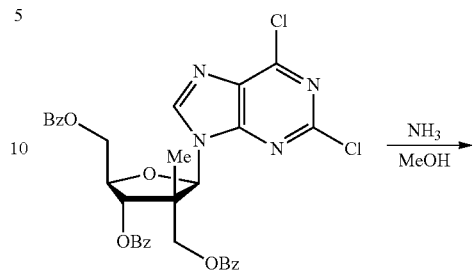

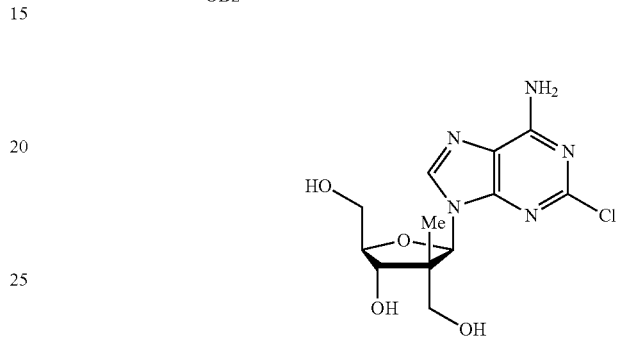

((2R,3S,4R,5R)-5-(6-amino-2-chloro-9H-purin-9-yl)-3-hydroxy-4-methyltetrahydrofuran-2,4-diyl)dimethanol $NH_3$ in MeOH [7N] (56 mL, 392.0 mmol) was added to Bz-nucleoside (3.88 g, 5.86 mmol) under $N_2$ at room temperature. After 3 days, the reaction mixture was concentrated to produce brown oil. The crude was fractionated by silica gel column chromatography (MeOH in $CH_2Cl_2$ 5%-20%) to yield the title compound as a mixture of anomers β:α (12:1) (60%, beige solid). $R_f$=0.17 (10% MeOH in $CH_2Cl_2$); IR (neat) $v_{max}$ 3339, 1653, 1594, 1309, 1036 cm$^{-1}$; Formula $C_{12}H_{16}ClN_5O_4$; MW 329.7395; $^1$H NMR (500 MHz, CD$_3$OD) δ 8.44 (s, 1H), 6.26 (s, 1H), 4.81 (s, 1H), 4.36 (d, J=8.7 Hz, 1H), 4.07 (ddd, J=8.8, 3.7, 2.3 Hz, 1H), 3.97 (dd, J=12.4, 2.4 Hz, 1H), 3.90-3.83 (m, 3H), 3.77 (d, J=11.2 Hz, 1H), 0.70 (s, 3H); $^{13}$C NMR (125 MHz, CD$_3$OD) δ 158.1, 155.2, 151.5, 141.9, 119.0, 90.6, 85.6, 76.3, 65.4, 61.7, 51.6, 17.3; MS (ESI) m/z 352.0 (M+Na$^+$, 100), 187.0; HRMS calcd for [M+H$^+$]: 330.0969, found: 330.0959; calcd for [M+Na$^+$]: 352.0789, found: 352.0783; [α]$_D$−10 (c 1.0, MeOH).

Example 2.13—Intermediate Compound

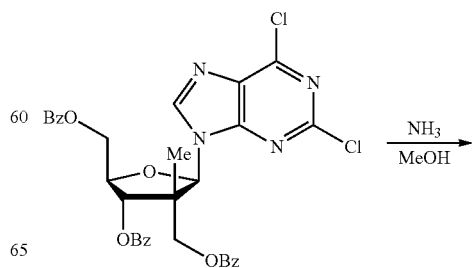

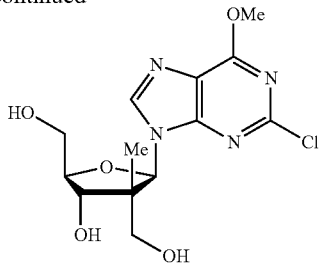

((2R,3S,4R,5R)-5-(2-chloro-6-methoxy-9H-purin-9-yl)-3-hydroxy-4-methyltetrahydrofuran-2,4-diyl)dimethanol A small amount of the title compound was also isolated and characterized after purification of the above crude mixture. The pure β-anomer was successfully crystallized in ethyl acetate (EtOAc) and proof of structure was obtained by X-ray analysis. $R_f$=0.35 (DCM/MeOH, 90:10); $[α]^{25}_D$+14 (c 0.8, MeOH); Formula: $C_{13}H_{17}ClN_4O_5$; MW: 344.75 g/mol; IR (neat) $v_{max}$ 3335, 2933, 2880, 1598, 1471 cm$^{-1}$; $^1$H NMR (500 MHz, CD$_3$OD) δ 8.76 (s, 1H), 6.40 (s, 1H), 4.37 (d, J=8.7 Hz, 1H), 4.20 (s, 3H), 4.13-4.06 (m, 1H), 3.99 (dd, J=12.4, 2.3 Hz, 1H), 3.93-3.85 (m, 2H), 3.79 (d, J=11.3 Hz, 1H), 0.70 (s, 3H) ppm (Labile protons were not observed due to exchange with deuterated solvent); $^{13}$C NMR (125 MHz, CD$_3$OD) δ 161.4, 153.1, 152.6, 143.0, 119.8, 89.5, 84.6, 74.9, 64.1, 60.4, 54.5, 50.6, 16.1 ppm; HRMS calcd for: $C_{13}H_{17}ClN_4NaO_5$ [M+Na]$^+$: 367.0780; found 367.0781 (0.46 ppm).

Example 2.14—Intermediate Compound

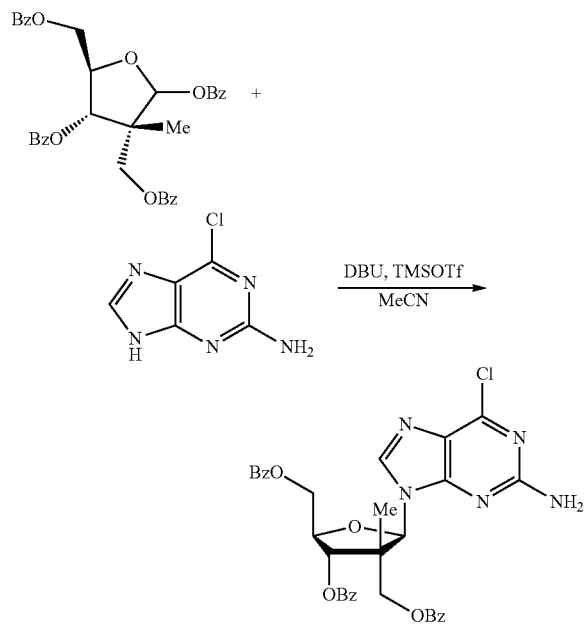

((2R,3S,4R,5R)-5-(2-amino-6-chloro-9H-purin-9-yl)-3-(benzoyloxy)-4-methyltetrahydrofuran-2,4-diyl)bis(methylene)dibenzoate. DBU (151 µL, 151 mg, 0.989 mmol) was added to a mixture of benzoylated sugar (202 mg, 0.330 mmol), and 2-amino-6-chloropurine (61.5 mg, 0.363 mmol) in dry acetonitrile (3.8 mL), under N$_2$ at 0° C. The mixture was stirred and then TMSOTf (243 µL, 299 mg, 1.32 mmol) was added dropwise over 5 minutes. After 15 minutes, the reaction was heated at 70° C. for 1 h, then diluted with CH$_2$Cl$_2$, and washed ×1 with a saturated solution of NaHCO$_3$. The aqueous phase was extracted with CH$_2$Cl$_2$ (×3), the organics dried over MgSO$_4$, and concentrated. DBU was removed by passing the crude through a pad of SiO$_2$ and washing with 2% MeOH in CH$_2$Cl$_2$ to produce an inseparable mixture of 4 compounds (83%, 177 mg, 67 (N–9 β): 13 (N–9 α) ratio and two other isomers). $R_f$=0.4 (50% ethyl acetate in hexanes); Formula $C_{33}H_{28}ClN_5O_7$; MW 642.0577;

For Major Compound:
$^1$H NMR (500 MHz, CDCl$_3$) δ 8.06-7.97 (m, 5H), 7.84-7.77 (m, 2H), 7.61-7.51 (m, 4H), 7.39 (ddd, J=13.8, 8.6, 6.9 Hz, 5H), 6.40 (s, 1H), 5.81 (d, J=5.9 Hz, 1H), 4.98 (dd, J=12.0, 4.0 Hz, 1H), 4.83-4.74 (m, 2H), 4.61 (td, J=5.8, 3.9 Hz, 1H), 4.52 (d, J=11.5 Hz, 1H), 1.20 (s, 3H); $^{13}$C NMR (125 MHz, CDCl$_3$) δ 166.4, 166.0, 165.7, 159.1, 153.1, 151.7, 140.5, 134.0, 133.6, 133.5, 129.9, 129.8, 129.4, 128.8, 128.7, 128.6, 125.4, 88.9, 80.7, 78.7, 66.0, 63.7, 49.2, 17.5; MS (ESI) m/z 664.2 (M+Na$^+$, 48), 360.3 (100), 227.0 (29); HRMS calcd for [M+H$^+$]: 642.1756, found: 642.1746; calcd for [M+Na$^+$]: 664.1575, found: 664.1568.

Example 2.15—Intermediate Compound

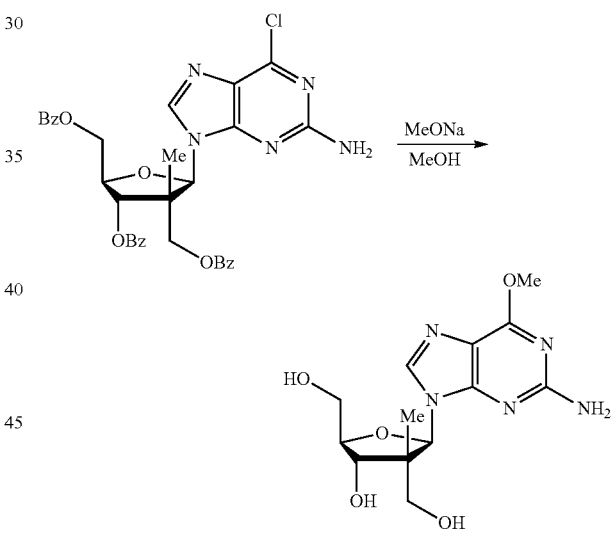

((2R,3S,4R,5R)-5-(2-amino-6-methoxy-9H-purin-9-yl)-3-hydroxy-4-methyltetrahydrofuran-2,4-diyl)dimethanol.
NaOMe in MeOH (25% wt) (73.5 µL, 0.321 mmol) was added to Bz-nucleoside (68.8 mg, 0.107 mmol) under Ar at room temperature. After 64 h, the reaction mixture was neutralized with HCl (2N), diluted in MeOH and concentrated. The crude was purified by reverse phase column chromatography (MeOH in H$_2$O 0%-100%) to yield the title compound as a mixture of isomers (82 (N–9 β): 11 (N–9 α)) (68%, 23.7 mg). $R_f$=0.05 (10% MeOH in CH$_2$Cl$_2$); Formula $C_{13}H_{19}N_5O_5$; MW 325.3205; $^1$H NMR (500 MHz, CD$_3$OD) δ 8.21 (s, 1H), 6.22 (s, 1H), 4.38-4.31 (m, 1H), 4.10-3.94 (m, 5H), 3.89-3.81 (m, 2H), 3.75 (dd, J=11.3, 1.5 Hz, 1H), 0.71 (s, 3H); $^{13}$C NMR (125 MHz, CD$_3$OD) δ 162.7, 161.7, 154.4, 139.9, 115.2, 90.3, 85.4, 76.4, 65.6, 61.7, 54.2, 51.5, 17.3; MS (ESI) m/z 348.1 (M+Na$^+$, 55), 326.1 (40), 226.9

Example 2.16—Intermediate Compound

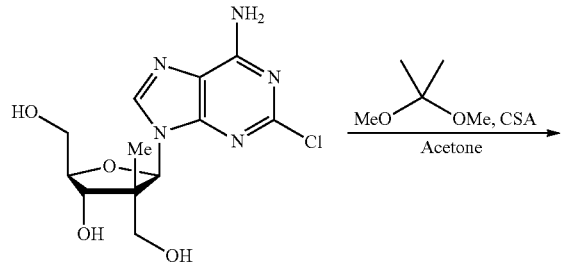

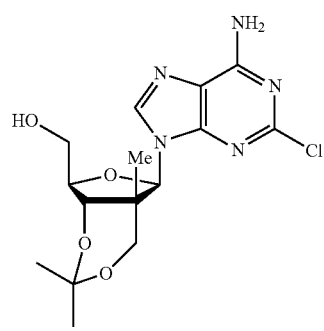

((4aR,5R,7R,7aS)-5-(6-amino-2-chloro-9H-purin-9-yl)-2,2,4α-trimethyltetrahydro-4H-furo[3,4-d][1,3]dioxin-7-yl) methanol. 2,2-dimethoxy propane (6.0 g, 7.0 mL, 57.15 mmol) was added to a mixture of nucleoside (1.05 g, 3.18 mmol), CSA (737 mg, 3.18 mmol), molecular sieves 3 Å (3 g), and dry acetone (32 mL). After 16.5 h, the reaction mixture was concentrated, diluted in CH$_2$Cl$_2$, and fractionated by silica gel column chromatography (10% methanol in dichloromethane) to yield two fractions: A) 365 mg (mixture 2:1, β:α anomers) and B) 374 mg (white solid, only β-anomer), 63% overall yield. R$_f$=0.36 (MeOH in CH$_2$Cl$_2$ 10%); IR (neat) ν$_{max}$ 3322, 3172, 2984, 2936, 1648, 1594, 1304, 1084 cm$^{-1}$; Formula C$_{15}$H$_{20}$ClN$_5$O$_4$; MW 369.8034; $^1$H NMR (500 MHz, CD$_3$OD) δ 8.31 (s, 1H), 6.31 (s, 1H), 4.17-4.07 (m, 3H), 3.89-3.77 (m, 2H), 3.62 (d, J=12.2 Hz, 1H), 1.44 (d, J=3.8 Hz, 6H), 0.80 (s, 3H); $^{13}$C NMR (125 MHz, CD$_3$OD) δ 158.0, 155.5, 151.4, 141.0, 118.9, 100.2, 90.6, 86.8, 79.4, 65.4, 63.1, 46.9, 27.2, 21.5, 16.8; MS (ESI) m/z 392.1 (M+Na$^+$, 100), 370.1 (16) 226.9; HRMS calcd for [M+H$^+$]: 370.1282, found: 370.1278; calcd for [M+Na$^+$]: 392.1102, found: 392.1102.

Example 2.17—Intermediate Compound

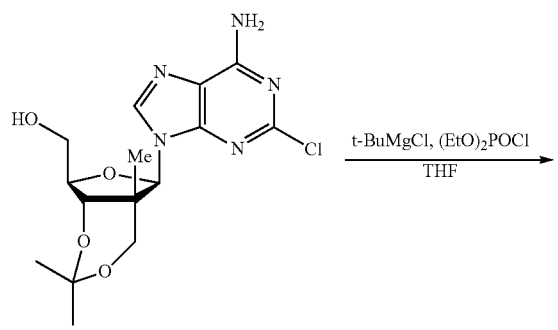

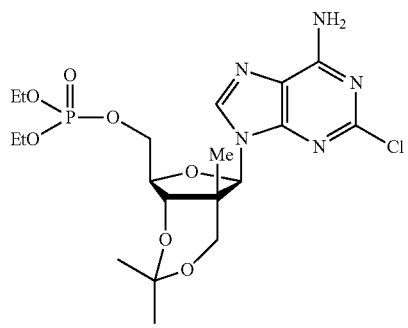

((4aR,5R,7R,7aS)-5-(6-amino-2-chloro-9H-purin-9-yl)-2,2,4α-trimethyltetrahydro-4H-furo[3,4-d][1,3]dioxin-7-yl) methyl diethyl phosphate. t-BuMgCl (2.5 mL, 2.47 mmol, 1 in THF) was added dropwise to a solution of nucleoside (365 mg, 0.987 mmol) in anhydrous THF (5.8 mL) under N$_2$ at room temperature. After addition, a clear yellow solution was formed. After 30 minutes, diethylchlorophosphate (426 mg, 357 μL, 2.47 mmol) was added dropwise. After 17.5 h, the reaction was quenched with MeOH (5 mL), concentrated, and fractionated by silica gel column chromatography (100% ethyl acetate, then 5%-10%-20% methanol in dichloromethane) to yield the product as a white solid (469 mg, 94% yield). R$_f$=0.6 (10% MeOH in CH$_2$Cl$_2$); IR (neat) ν$_{max}$ 3323, 3182, 2987, 1650, 1595, 1302, 1254, 1031 cm$^{-1}$; Formula C$_{19}$H$_{29}$ClN$_5$O$_7$P; MW 505.8896; $^1$H NMR (500 MHz, CDCl$_3$) δ 8.16 (s, 1H), 6.46 (dt, J=26.5, 12.1 Hz, 2H), 6.32 (s, 1H), 4.36-4.28 (m, 2H), 4.26 (dt, J=4.4, 2.0 Hz, 1H), 4.20-4.12 (m, 5H), 4.03 (d, J=2.4 Hz, 1H), 3.59 (d, J=12.2 Hz, 1H), 1.42 (d, J=25.3 Hz, 6H), 1.39-1.32 (m, 6H), 0.79 (s, 3H); $^{13}$C NMR (125 MHz, CDCl$_3$) δ 156.4, 154.3, 150.3, 139.4, 118.5, 99.4, 89.6, 82.7, 82.7, 78.1, 66.6, 66.5, 64.7, 64.3, 64.3, 46.4, 26.2, 21.6, 16.8, 16.3, 16.2; MS (ESI) m/z 528.1 (M+Na$^+$, 100), 506.1 (27); HRMS calcd for [M+H$^+$]: 506.1571, found: 506.1565; calcd for [M+Na$^+$]: 528.1391, found: 528.1386; [α]$_D$+35 (c 1.0, MeOH).

Example 2.18—Cardioprotective Compound-LCB2122

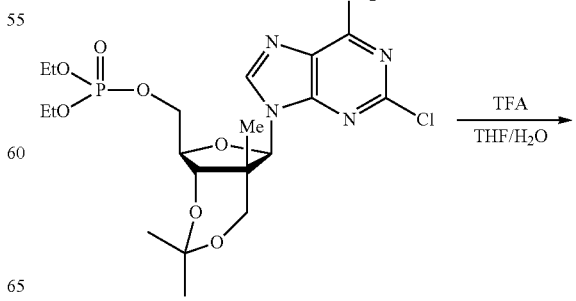

-continued

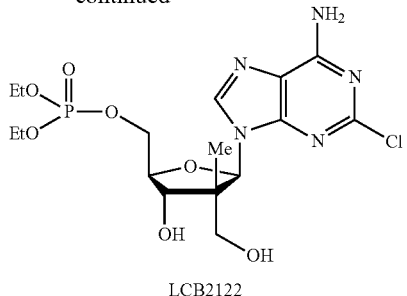

LCB2122

((2R,3S,4R,5R)-5-(6-amino-2-chloro-9H-purin-9-yl)-3-hydroxy-4-(hydroxymethyl)-4-methyltetrahydrofuran-2-yl)methyl diethyl phosphate (LCB2122). A mixture of TFA/H$_2$O (8:2) (7.1 mL) was added to a solution of the prodrug (360 mg, 0.711 mmol) in THF (7.1 mL) at room temperature and open atmosphere. After 1 h, the solvent was removed under vacuum, concentrated ×3 from MeOH and purified by silica gel column chromatography (MeOH in CH$_2$Cl$_2$ 5-20%) to yield the title compound as white solid (294 mg, 88% yield). R$_f$=0.2 (10% MeOH in CH$_2$Cl$_2$); IR (neat) v$_{max}$ 3327, 3156, 2984, 1648, 1596, 1313, 1243, 1029 cm$^{-1}$; Formula C$_{16}$H$_{25}$ClN$_5$O$_7$P; MW 465.8258; $^1$H NMR (500 MHz, CD$_3$OD) δ 8.18 (s, 1H), 6.27 (s, 1H), 4.56-4.47 (m, 1H), 4.45-4.33 (m, 2H), 4.30-4.23 (m, 1H), 4.17-4.03 (m, 4H), 3.88 (d, J=11.2 Hz, 1H), 3.74 (d, J=11.2 Hz, 1H), 1.29 (qd, J=7.0, 1.0 Hz, 6H), 0.72 (s, 3H); $^{13}$C NMR (125 MHz, CD$_3$OD) δ 158.2, 155.3, 151.4, 141.7, 119.3, 90.9, 83.7, 77.0, 68.4, 65.6, 65.5, 65.5, 65.3, 51.5, 17.1, 16.4, 16.3, 16.3; MS (ESI) m/z 488.1 (M+Na$^+$, 100), 360.3 (15); HRMS calcd for [M+H$^+$]: 466.1258, found: 466.1247; calcd for [M+Na$^+$]: 488.1078, found: 488.1072.

Example 2.19—Cardioprotective Compound-LCB2195

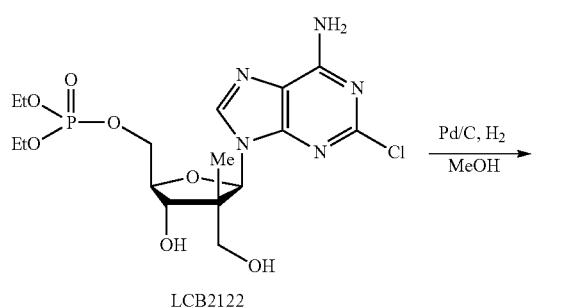

((2R,3S,4R,5R)-5-(6-amino-9H-purin-9-yl)-3-hydroxy-4-(hydroxymethyl)-4-methyltetrahydrofuran-2-yl)methyl diethyl phosphate (LCB2195). To a solution of LCB2122 (22.9 mg, 0.0492 mmol) in MeOH (0.5 mL, 0.1 M) at room temperature was added palladium on carbon (10 wt. %) (22.9 mg) and the N$_2$ (g) was removed from the reaction and replaced by a positive pressure of H$_2$. After 6 hours at room temperature, the mixture was filtered over celite with MeOH/EtOAc (50:50) and concentrated in vacuo. Crude product was purified by reverse phase (C18) flash chromatography (H$_2$O/MeCN, 60:40 to give the final product as a white solid (15.2 mg, 72% yield). R$_f$=0.2 (DCM/MeOH, 95:5); [α]$^{25}_D$ -2 (c 0.8, MeOH); Formula: C$_{16}$H$_{26}$N$_5$O$_7$P; MW: 431.39 g/mol; IR (neat) v$_{max}$ 3330, 3195, 2981, 1647, 1600 cm$^{-1}$; $^1$H NMR (500 MHz, CD$_3$OD) δ 8.27 (s, 1H), 8.23 (s, 1H), 6.38 (s, 1H), 4.51-4.36 (m, 3H), 4.32-4.26 (m, 1H), 4.20-4.09 (m, 4H), 3.90 (d, J=11.2 Hz, 1H), 3.77 (d, J=11.2 Hz, 1H), 1.32 (tdd, J=7.1, 2.0, 1.0 Hz, 6H), 0.71 (s, 3H) ppm (Labile protons were not observed due to exchange with deuterated solvent); $^{13}$C NMR (125 MHz, CD$_3$OD) δ 156.0, 152.5, 149.0, 139.9, 118.8, 89.1, 82.1 (d, J=7.5 Hz), 75.4, 66.8 (d, J=5.8 Hz), 64.23 (d, J=5.7 Hz), 64.18 (d, J=5.8 Hz), 63.9, 50.1, 15.7, 15.0 (d, J=5.1 Hz), 14.9 (d, J=5.0 Hz) ppm; HRMS calcd for: C$_{16}$H$_{27}$N$_5$O$_7$P [M+H]$^+$: 432.1643; found 432.1642 (−0.13 ppm).

Example 2.20—Intermediate Compound

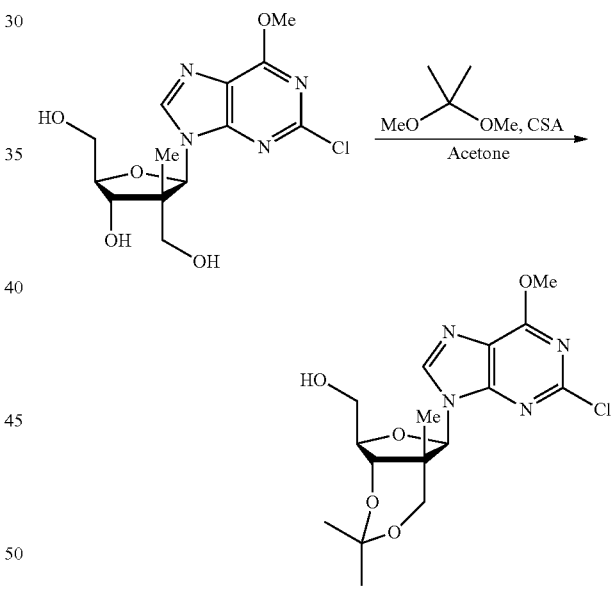

((4aR,5R,7R,7aS)-5-(2-chloro-6-methoxy-9H-purin-9-yl)-2,2,4α-trimethyltetrahydro-4H-furo[3,4-d][1,3]dioxin-7-yl)methanol. 2,2-dimethoxy propane (1.60 mL, 18.0 equiv., 13.1 mmol) was added to a mixture of nucleoside (250 mg, 725 umol), CSA (168 mg, 725 umol), molecular sieves 3 Å (500 mg), and dry acetone (8 mL). After 16.5 h, the reaction mixture was concentrated, diluted in CH$_2$Cl$_2$, and purified by silica gel column chromatography (5-10% methanol in dichloromethane) to yield the product 278 mg (99.6%) as a white/yellow powder. Formula C$_{16}$H$_{21}$ClN$_4$O$_5$; MW 384.8170; $^1$H NMR (500 MHz, CD$_3$OD) δ 8.53 (s, 1H), 6.41 (s, 1H), 4.19 (d, J=0.7 Hz, 4H), 4.17 (d, J=2.2 Hz, 1H), 4.14-4.12 (m, 1H), 3.87 (dd, J=12.2, 4.5 Hz, 1H), 3.81 (dd, J=12.1, 5.3 Hz, 1H), 3.65 (d, J=12.3 Hz, 1H), 1.45 (s, 3H), 1.45 (s, 3H), 0.80 (s, 3H) (Labile protons were not observed due to exchange with deuterated solvent).

Example 2.21—Intermediate Compound

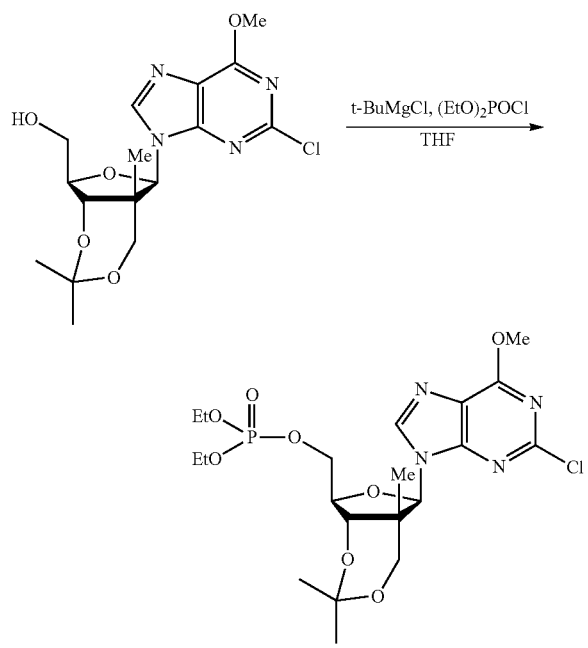

((4aR,5R,7R,7aS)-5-(2-chloro-6-methoxy-9H-purin-9-yl)-2,2,4α-trimethyltetrahydro-4H-furo[3,4-d][1,3]dioxin-7-yl)methyl diethyl phosphate. t-BuMgCl (1.08 mL, 1.50 equiv., 1.08 mmol, 1 M in THF) was added dropwise to a solution of nucleoside (278 mg, 722 umol) in anhydrous THF (7.2 mL) under $N_2$ at room temperature. After addition, a clear yellow solution was formed. After 40 minutes, diethylchlorophosphate (157 μL, 1.50 equiv., 1.08 mmol) was added dropwise. After 5 h, the reaction was quenched with MeOH, concentrated, and purified by silica gel column chromatography (5%-10% methanol in dichloromethane) to yield the product as a yellow oil (262 mg, 70% yield). Formula $C_{20}H_{30}ClN_4O_8P$; MW 520.9038; 1H NMR (500 MHz, $CD_3OD$) δ 8.52 (s, 1H), 6.50 (s, 1H), 4.42-4.35 (m, 2H), 4.24 (d, J=2.0 Hz, 1H), 4.23-4.14 (m, 7H), 4.14-4.09 (m, 2H), 3.70 (d, J=12.4 Hz, 1H), 1.47 (s, 6H), 1.40-1.27 (m, 6H), 0.81 (s, 3H).

Example 2.22—Cardioprotective Compound-LCB2223

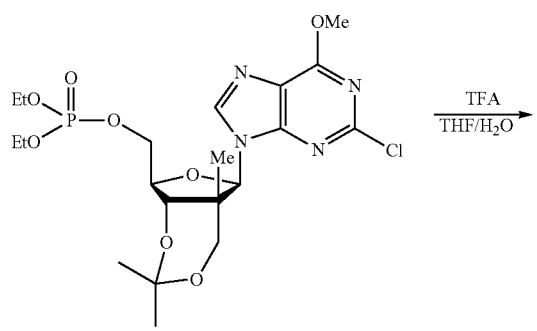

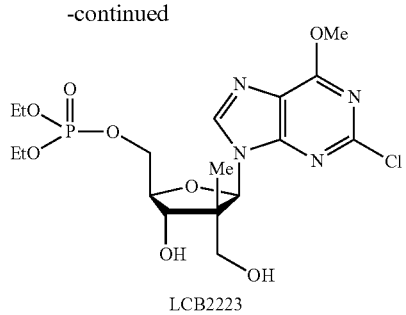

((2R,3S,4R,5R)-5-(2-chloro-6-methoxy-9H-purin-9-yl)-3-hydroxy-4-(hydroxymethyl)-4-methyltetrahydrofuran-2-yl)methyl diethyl phosphate (LCB2223). A mixture of TFA/$H_2O$ (8:2) (5.2 mL, 0.1 M) was added to a solution of the prodrug (262 mg, 503 umol) in THF (5.2 mL, 0.1 M) at room temperature and open atmosphere. After 3 h, MeOH was added and the solvent was removed under vacuum, concentrated ×3 from MeOH and purified by reverse phase column chromatography (C18) ($H_2O$/MeCN, 60:40) to yield the title compound as white solid (128 mg, 53% yield). $R_f$=0.4 (10% MeOH in $CH_2Cl_2$); $[α]^{25}_D$+13 (c 0.7, MeOH); Formula: $C_{17}H_{26}ClN_4O_8P$; MW: 480.8388 g/mol; IR (neat) $v_{max}$ 3333, 2983, 2359, 1597, 1472, 1387 $cm^{-1}$; $^1H$ NMR (500 MHz, $CD_3OD$) δ 8.38 (s, 1H), 6.38 (s, 1H), 4.55-4.47 (m, 1H), 4.44-4.36 (m, 2H), 4.32-4.26 (m, 1H), 4.19 (s, 3H), 4.15-4.09 (m, 4H), 3.89 (d, J=11.2 Hz, 1H), 3.74 (d, J=11.2 Hz, 1H), 1.34-1.25 (m, 6H), 0.70 (s, 3H) (Labile protons were not observed due to exchange with deuterated solvent); $^{13}C$ NMR (125 MHz, $CD_3OD$) δ 162.7, 154.3, 153.7, 144.1, 121.4, 91.2, 83.83, 83.77, 76.9, 68.4 (d, J=5.8 Hz), 65.6 (t, J=5.3 Hz), 65.2, 55.7, 51.6, 17.1, 16.4 (d, J=4.7 Hz), 16.3 (d, J=4.7 Hz); HRMS calcd for $[M+Na^+]$: 503.1069, found: 503.1055 (-2.78 ppm).

Example 2.23—Intermediate Compound

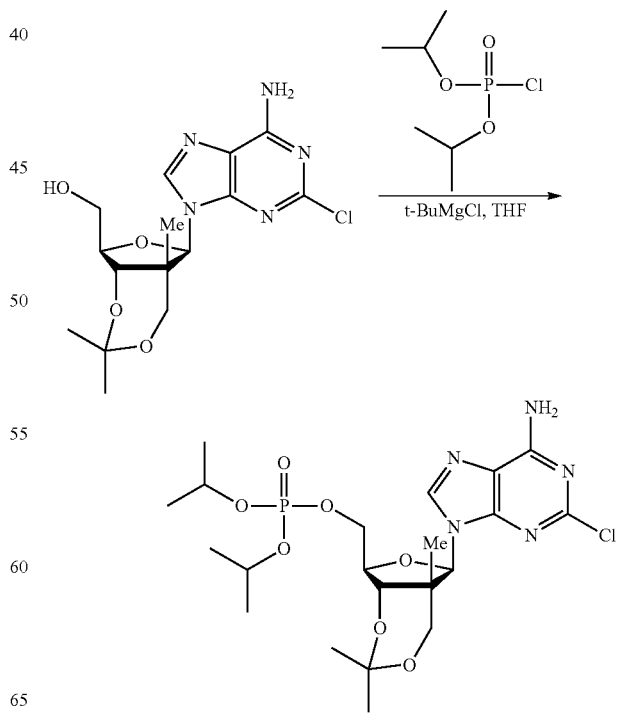

((4aR,5R,7R,7aS)-5-(6-amino-2-chloro-9H-purin-9-yl)-2,2,4α-trimethyltetrahydro-4H-furo[3,4-d][1,3]dioxin-7-yl) methyl diisopropyl phosphate. To a solution of acetonide (34.7 mg, 0.0938 mmol) in THF (1 mL, 0.1 M) was added t-BuMgCl (141 μL, 0.141 mmol) dropwise at room temperature and the mixture was stirred for 45 minutes. Diisopropylchlorophosphate (24.9 μL, 0.141 mmol) was added slowly and the reaction was stirred for 4 hours. The reaction was quenched by addition of MeOH and concentrated in vacuo. Crude product was purified by reverse phase (C18) flash chromatography (H$_2$O/MeCN, 50:50) to give the product as a white solid (34.8 mg, 70% yield). R$_f$=0.55 (DCM/MeOH, 90:10); [α]$^{25}$$_D$+25 (c 2.36, MeOH); Formula: C$_{21}$H$_{33}$ClN$_5$O$_7$P; MW: 533.95 g/mol; IR (neat) v$_{max}$ 3324, 3182, 2983, 2937, 1650, 1595 cm$^{-1}$; $^1$H NMR (500 MHz, CD$_3$OD) δ 8.32 (s, 1H), 6.40 (s, 1H), 4.70 (hept, J=12.7, 6.3 Hz, 2H), 4.35 (dd, J=8.2, 5.0 Hz, 2H), 4.32-4.27 (m, 1H), 4.23 (d, J=2.0 Hz, 1H), 4.12 (d, J=12.3 Hz, 1H), 3.67 (d, J=12.4 Hz, 1H), 1.47 (s, 3H), 1.46 (s, 3H), 1.38 (t, J=6.4 Hz, 12H), 0.83 (s, 3H) ppm (Labile protons were not observed due to exchange with deuterated solvent); $^{13}$C NMR (125 MHz, CD$_3$OD) δ 156.6, 154.2, 150.0, 139.4, 117.5, 98.8, 89.0, 83.0 (d, J=7.0 Hz), 77.8, 73.5 (d, J=2.8 Hz), 73.4 (d, J=2.5 Hz), 66.7 (d, J=5.8 Hz), 63.6, 44.9, 26.0, 22.6, 22.54, 22.51, 22.50, 19.8, 15.5 ppm; HRMS calcd for: C$_{21}$H$_{34}$ClN$_5$O$_7$P [M+H]$^+$: 534.1879; found 534.1868 (−1.97 ppm).

Example 2.24—Cardioprotective Compound-LCB2177

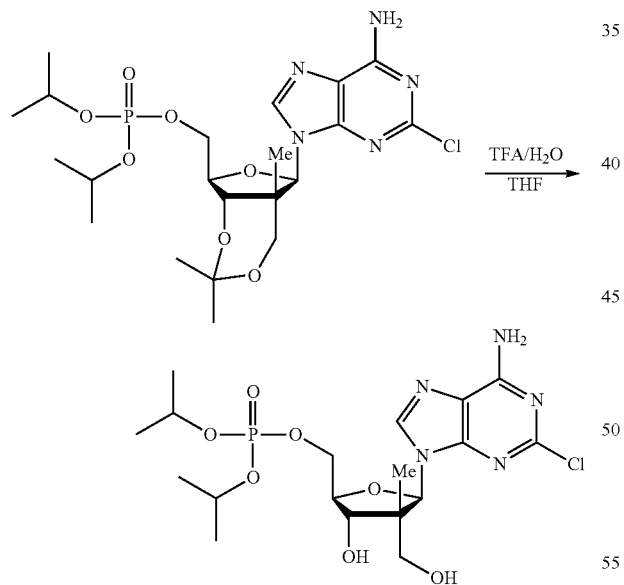

((2R,3S,4R,5R)-5-(6-amino-2-chloro-9H-purin-9-yl)-3-hydroxy-4-(hydroxymethyl)-4-methyltetrahydrofuran-2-yl) methyl diisopropyl phosphate (LCB2177). To a solution of nucleoside (34.8 mg, 0.0652 mmol) in THF (0.7 mL, 0.1 M) was slowly added a mixture of TFA/H$_2$O (8:2) (0.7 mL, 0.1 M) at room temperature and open atmosphere. After 4 hours, MeOH was added and the reaction was concentrated in vacuo, then co-evaporated with MeOH (3×). Crude product was purified by reverse phase (C18) flash chromatography (H$_2$O/MeCN, 60:40) to give the final product as a white solid (23.9 mg, 74% yield). R$_f$=0.3 (DCM/MeOH, 90:10); [α]$^{25}$$_D$+7 (c 1.72, MeOH); Formula: C$_{18}$H$_{29}$ClN$_5$O$_7$P; MW: 493.88 g/mol; IR (neat) v$_{max}$ 3344, 2984, 2936, 2405, 1615 cm$^{-1}$; $^1$H NMR (500 MHz, CD$_3$OD) δ 8.20 (s, 1H), 6.28 (s, 1H), 4.71-4.58 (m, 2H), 4.50 (dt, J=11.6, 5.9 Hz, 1H), 4.43 (d, J=8.8 Hz, 1H), 4.37 (ddd, J=11.3, 5.2, 2.1 Hz, 1H), 4.31-4.22 (m, 1H), 3.89 (d, J=11.2 Hz, 1H), 3.76 (d, J=11.2 Hz, 1H), 1.33 (dd, J=6.3, 2.3 Hz, 9H), 1.29 (d, J=6.2 Hz, 3H), 0.73 (s, 3H) ppm (Labile protons were not observed due to exchange with deuterated solvent); $^{13}$C NMR (125 MHz, CD$_3$OD) δ 156.8, 153.9, 150.0, 140.4, 117.9, 89.5, 82.4 (d, J=8.0 Hz), 75.5, 73.3 (d, J=2.9 Hz), 73.2 (d, J=2.8 Hz), 66.9 (d, J=5.9 Hz), 63.9, 50.1, 22.4 (td, J=5.1, 3.5 Hz) (4C), 15.7 ppm; HRMS calcd for: C$_{18}$H$_{30}$ClN$_5$O$_7$P [M+H]$^+$: 494.1566; found 494.1579 (2.70 ppm).

Example 2.25—Intermediate Compound

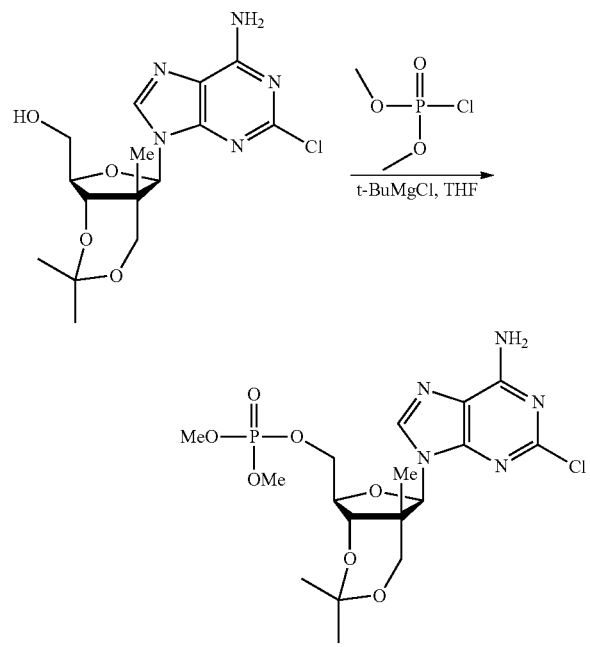

((4aR,5R,7R,7aS)-5-(6-amino-2-chloro-9H-purin-9-yl)-2,2,4α-trimethyltetrahydro-4H-furo[3,4-d][1,3]dioxin-7-yl) methyl dimethyl phosphate. Following the same procedure as in example 2.23 using Dimethylchlorophosphite and purification by silica gel column chromatography (5:95 MeOH:DCM), the product was obtained. R$_f$=0.57 (DCM/MeOH, 95:5); [α]$^{25}$$_D$+35 (c 0.9, CD$_3$OD); Formula: C$_{17}$H$_{25}$ClN$_5$O$_7$P; MW: 477.84 g/mol; IR (neat) v$_{max}$ 3365, 3182, 2989, 2936, 1610 cm$^{-1}$; $^1$H NMR (500 MHz, (CD$_3$)$_2$SO) δ 8.36 (s, 1H), 7.87 (s, 2H), 6.35 (s, 1H), 4.31 (dd, J=8.6, 6.1 Hz, 2H), 4.26 (d, J=1.4 Hz, 1H), 4.20-4.14 (m, 1H), 3.86 (d, J=12.5 Hz, 1H), 3.72 (d, J=3.6 Hz, 3H), 3.70 (d, J=3.7 Hz, 3H), 3.61 (d, J=12.4 Hz, 1H), 1.43 (s, 3H), 1.39 (s, 3H), 0.75 (s, 3H); $^{13}$C NMR (125 MHz, CD$_3$OD) δ 158.1, 155.6, 151.5, 140.9, 118.9, 100.2, 90.3, 84.4 (d, J=6.2 Hz), 79.1, 68.7 (d, J=5.8 Hz), 64.9, 55.5 (d, J=6.2 Hz), 55.4 (d, J=6.2 Hz), 46.1, 27.5, 21.1, 16.8 ppm; HRMS calcd for: C$_{17}$H$_{26}$ClN$_5$O$_7$P [M+H]$^+$: 478.1253; found 478.1249 (−0.91 ppm).

Example 2.26—Cardioprotective Compound-LCB2234

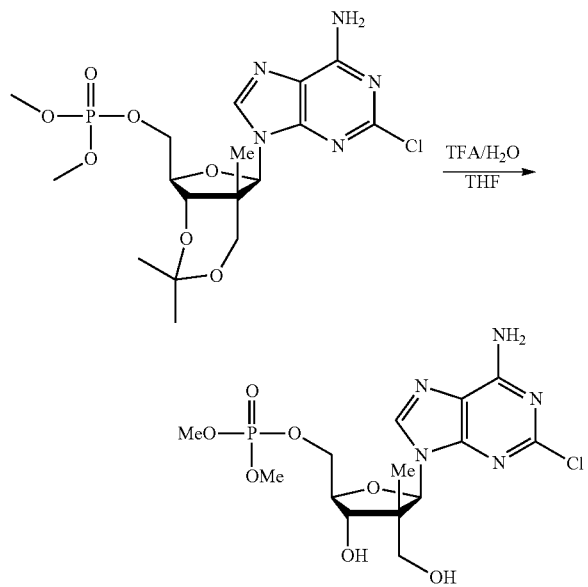

((2R,3S,4R,5R)-5-(6-amino-2-chloro-9H-purin-9-yl)-3-hydroxy-4-(hydroxymethyl)-4-methyltetrahydrofuran-2-yl) methyl dimethyl phosphate (LCB2234). Following the same procedure as in example 2.24 and purification by reverse phase column chromatography (H$_2$O:MeCN), the product was obtained. R$_f$=0.38 (DCM/MeOH, 90:10); [α]$^{25}_D$+4.1 (c 0.8, CD$_3$OD); Formula: C$_{14}$H$_{21}$ClN$_5$O$_7$P; MW: 437.77 g/mol; IR (neat) v$_{max}$ 3333, 3210, 2952, 1616 cm$^{-1}$; $^1$H NMR (500 MHz, CD$_3$OD) δ 8.18 (s, 1H), 6.28 (s, 1H), 4.57-4.51 (m, 1H), 4.43-4.37 (m, 2H), 4.29-4.24 (m, 1H), 3.88 (d, J=11.2 Hz, 1H), 3.78 (d, J=6.6 Hz, 3H), 3.77 (d, J=6.6 Hz, 3H), 3.74 (d, J=11.2 Hz, 1H), 0.72 (s, 3H) ppm (Labile protons were not observed due to exchange with deuterated solvent); $^{13}$C NMR (125 MHz, CD$_3$OD) δ 158.2, 155.4, 151.4, 141.7, 119.3, 90.9, 83.6 (d, J=7.3 Hz), 77.0, 68.7 (d, J=5.7 Hz), 65.3, 55.31 (d, J=6.0 Hz), 55.25 (d, J=6.1 Hz), 51.6, 17.1 ppm; HRMS calcd for: C$_{14}$H$_{22}$ClN$_5$O$_7$P [M+H]$^+$: 438.0940; found 438.0946 (1.42 ppm).

Example 2.27—Intermediate Compound

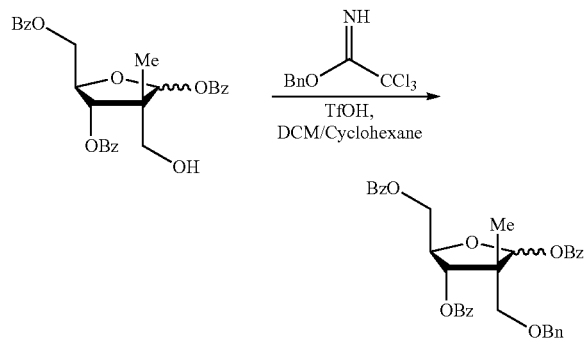

(3R,4S,5R)-5-((benzoyloxy)methyl)-3-((benzyloxy)methyl)-3-methyltetrahydrofuran-2,4-diyl dibenzoate. To a solution of free alcohol (2.87 g, 5.85 mmol) in DCM/Cyclohexane (1:2) (60 mL, 0.1 M) at 0° C. was added benzyl 2,2,2-trichloroacetimidate (3.26 mL, 17.55 mmol) and TfOH (51.6 μL, 0.585 mmol) dropwise. After 16 hours at rt, the reaction was quenched by Et$_3$N (122 μL, 0.878 mmol) at 0° C., stirred for 15 minutes and concentrated in vacuo. The product was filtered over celite with DCM, concentrated in vacuo and the crude product was purified by flash chromatography on silica gel (Hexanes/EtOAc, 80:20) to give a mixture of products in a ~5:1 ratio (2.53 g, 75% yield). R$_f$=0.4 (Hexanes/EtOAc, 70:30); Formula: C$_{35}$H$_{32}$O$_8$; MW: 580.63 g/mol; IR (neat) v$_{max}$ 3065, 3033, 2941, 2882, 1720 cm$^{-1}$; $^1$H NMR (500 MHz, CDCl$_3$) δ 8.10 (d, J=7.4 Hz, 2H$_a$), 8.06 (d, J=7.5 Hz, 4H$_b$), 8.00 (d, J=7.4 Hz, 2H$_a$), 7.96 (d, J=7.6 Hz, 2H$_a$), 7.92 (d, J=7.5 Hz, 2H$_b$), 7.59 (t, J=7.3 Hz, 3H$_a$), 7.52 (t, J=7.5 Hz, 3H$_b$), 7.50-7.29 (m, 20H$_{a,b}$), 7.26-7.20 (m, 2H$_{a,b}$), 6.66 (s, 1H$_b$), 6.62 (s, 1H$_a$), 5.79 (d, J=6.6 Hz, 1H$_b$), 4.74 (s, 2H$_a$), 4.68 (d, J=11.6 Hz, 1H$_a$), 4.64 (s, 2H$_b$), 4.63-4.49 (m, 6H$_{a,b}$), 4.44 (dd, J=11.8, 5.1 Hz, 1H$_a$), 4.29 (d, J=7.2 Hz, 1H$_a$), 3.84 (d, J=9.3 Hz, 1H$_b$), 3.66 (d, J=9.2 Hz, 1H$_b$), 1.41 (s, 3H$_a$), 1.38 (s, 3H$_b$) ppm; $^{13}$C NMR (125 MHz, CDCl$_3$) δ 166.4, 166.3, 165.3, 137.3, 133.4, 133.2, 133.1, 129.72 (3C), 129.68 (3C), 129.67 (3C), 128.6 (2C), 128.53 (2C), 128.52 (2C), 128.3 (2C), 128.2, 127.7 (2C), 101.0, 84.6, 81.6, 73.9, 65.9, 65.3, 50.0, 17.3 ppm; HRMS calcd for: C$_{35}$H$_{32}$NaO$_8$ [M+Na]$^+$: 603.1989; found 603.1975 (−2.34 ppm).

Example 2.28—Intermediate Compound

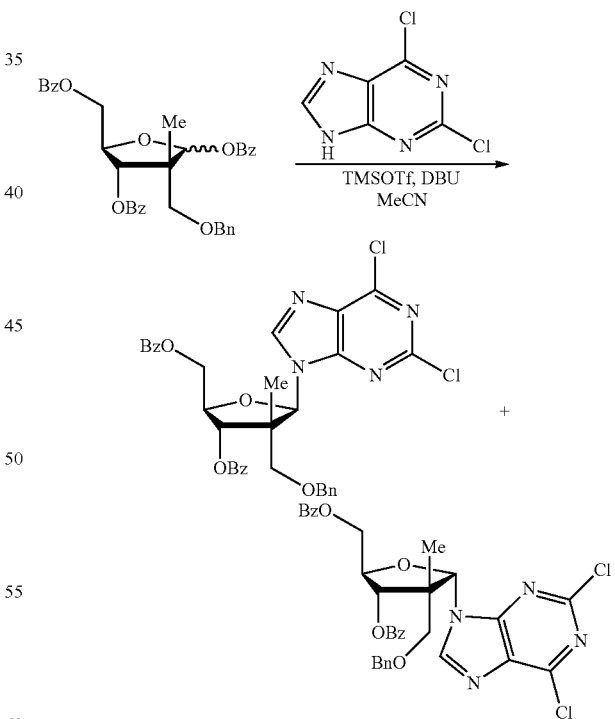

((2R,3S,4R,5R)-3-(benzoyloxy)-4-((benzyloxy)methyl)-5-(2,6-dichloro-9H-purin-9-yl)-4-methyltetrahydrofuran-2-yl)methyl benzoate (β-anomer). To a mixture of anomeric benzoates (2.53 g, 4.36 mmol) and 2,6-dichloropurine (907 mg, 4.79 mmol) in dry acetonitrile (22 mL, 0.2 M) at −10° C. was added DBU (1.99 mL, 13.1 mmol). The mixture was stirred and then TMSOTf (3.21 mL, 17.4 mmol) was added dropwise over 2 minutes. After 5 hours at −10° C., the reaction was quenched by addition of a saturated solution of NaHCO$_3$ at −10° C., suspended in DCM and washed with a saturated solution of NaHCO$_3$. The aqueous layer was extracted with DCM (3×) and the combined organic fractions were washed with an aqueous solution of citric acid (0.1 M), dried (MgSO$_4$), filtered and concentrated in vacuo. $^1$H-NMR of the crude showed a ~7:1 ratio of β:α anomers. Crude product was purified by flash chromatography on silica gel (Hexanes/EtOAc, 70:30) to provide the pure β-anomer (1.08 g, 40% yield). R$_f$=0.25 (Hexanes/EtOAc, 70:30); [α]$^{25}_D$+16 (c 0.76, MeOH); Formula: C$_{33}$H$_{28}$Cl$_2$N$_4$O$_6$; MW: 647.51 g/mol; IR (neat) v$_{max}$ 3124, 3065, 2920, 1719, 1268 cm$^{-1}$; $^1$H NMR (500 MHz, CDCl$_3$) δ 8.37 (s, 1H), 8.04 (dd, J=8.4, 1.3 Hz, 2H), 7.91 (dd, J=8.3, 1.4 Hz, 2H), 7.65 (t, J=7.5 Hz, 1H), 7.60 (t, J=7.5 Hz, 1H), 7.52 (appt, J=7.8 Hz, 2H), 7.45 (appt, J=7.8 Hz, 2H), 7.34 (d, J=4.4 Hz, 4H), 7.33-7.29 (m, 1H), 6.54 (s, 1H), 4.79 (d, J=11.7 Hz, 1H), 4.71 (d, J=5.5 Hz, 2H), 4.70-4.67 (m, 2H), 4.57 (d, J=11.7 Hz, 1H), 4.55-4.51 (m, 1H), 4.24 (d, J=6.8 Hz, 1H), 1.03 (s, 3H) ppm; $^{13}$C NMR (125 MHz, CDCl$_3$) δ 166.2, 166.1, 153.2, 152.4, 152.0, 144.0, 136.6, 133.6, 133.4, 130.9, 129.6 (3C), 129.4 (3C), 129.3, 128.8 (2C), 128.7 (2C), 128.6 (2C), 128.2 (2C), 89.1, 82.9, 81.1, 73.6, 66.3, 63.7, 49.4, 17.9 ppm; HRMS calcd for: C$_{33}$H$_{28}$Cl$_2$N$_4$NaO$_6$ [M+Na]$^+$: 669.1278; found 669.1272 (−0.98 ppm).

Example 2.29—Intermediate Compound

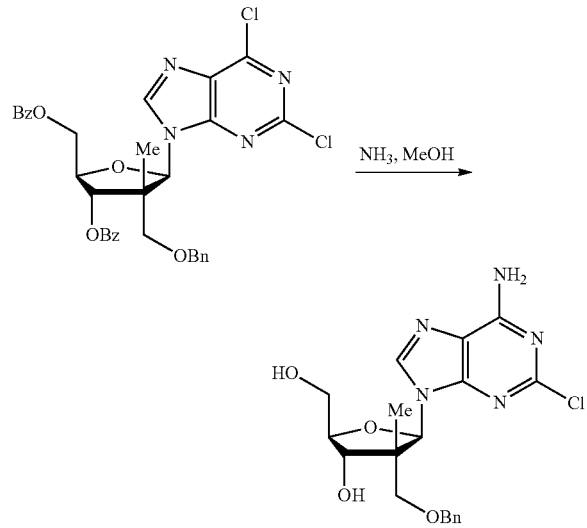

(2R,3S,4R,5R)-5-(6-amino-2-chloro-9H-purin-9-yl)-4-((benzyloxy)methyl)-2-(hydroxymethyl)-4-methyltetrahydrofuran-3-ol. To a solution of protected nucleoside (371 mg, 0.573 mmol) in MeOH (12 mL, 0.05 M) in a high-pressure flask at room temperature was bubbled NH$_{3(g)}$ until saturation of the system, then the flask was rapidly closed with a high-pressure seal and the solution was stirred at 80° C. for 24 hours. NH$_{3(g)}$ was bubbled for a second time until saturation of the system and after closing the flask with the high-pressure seal, the reaction was stirred for another 16 hours at 80° C. The mixture was diluted with MeOH (10 mL) and concentrated in vacuo. Crude product was purified by flash chromatography on silica gel (DCM/MeOH, 90:10) to give the product as a white solid (178 mg, 74% yield). R$_f$=0.4 (DCM/MeOH, 90:10); [α]$^{25}_D$−13 (c 1.13, MeOH); Formula: C$_{19}$H$_{22}$ClN$_5$O$_4$; MW: 419.87 g/mol; IR (neat) v$_{max}$ 3357, 2936, 2882, 2362, 1614 cm$^{-1}$; $^1$H NMR (500 MHz, CD$_3$OD) δ 8.45 (s, 1H), 7.41 (d, J=6.8 Hz, 2H), 7.36 (appt, J=7.4 Hz, 2H), 7.30 (t, J=7.2 Hz, 1H), 6.27 (s, 1H), 4.76-4.66 (m, 2H), 4.39 (d, J=8.3 Hz, 1H), 4.20 (ddd, J=8.3, 3.6, 2.5 Hz, 1H), 3.97 (dd, J=12.4, 2.4 Hz, 1H), 3.91 (d, J=11.3 Hz, 1H), 3.86 (dd, J=12.4, 3.7 Hz, 1H), 3.77 (d, J=11.3 Hz, 1H), 0.68 (s, 3H) ppm (Labile protons were not observed due to exchange with deuterated solvent); $^{13}$C NMR (125 MHz, CD$_3$OD) δ 156.7, 153.9, 150.1, 140.5, 138.1, 128.0 (2C), 127.9 (2C), 127.6, 117.6, 89.2, 83.6, 82.4, 73.4, 64.0, 60.8, 50.6, 16.5 ppm; HRMS calcd for: C$_{19}$H$_{23}$ClN$_5$O$_4$ [M+H]$^+$: 420.1433; found 420.1429 (−0.90 ppm).

Example 2.30—Intermediate Compound

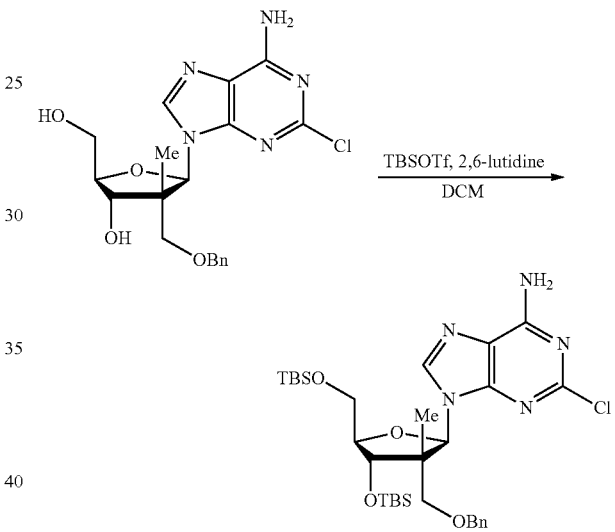

9-((2R,3R,4S,5R)-3-((benzyloxy)methyl)-4-((tert-butyldimethylsilyl)oxy)-5-(((tert-butyldimethylsilyl)oxy)methyl)-3-methyltetrahydrofuran-2-yl)-2-chloro-9H-purin-6-amine. To a solution of nucleoside (317 mg, 0.756 mmol) in DCM (7.6 mL, 0.1 M) and DMF (1 drop) at 0° C. was added 2,6-lutidine (438 µL, 3.78 mmol) and TBSOTf (0.515 mL, 2.27 mmol) dropwise. The reaction was stirred for 16 hours at room temperature, then quenched by addition of a saturated solution of NaHCO$_3$ and concentrated in vacuo. The product was diluted with Et$_2$O, washed with brine and HCl [0.1 M], dried (MgSO$_4$), filtered and concentrated in vacuo. Crude product was purified by flash chromatography on silica gel (Hexanes/EtOAc, 60:40) to give the product as a white foam (321 mg, 65% yield). R$_f$=0.3 (Hexanes/EtOAc, 60:40); [α]$^{25}_D$+7 (c 1.42, MeOH); Formula: C$_{31}$H$_{50}$ClN$_5$O$_4$Si$_2$; MW: 648.39 g/mol; IR (neat) v$_{max}$ 2925, 2855, 2324, 1612 cm$^{-1}$; $^1$H NMR (500 MHz, CD$_3$OD) δ 8.48 (s, 1H), 7.36 (d, J=4.4 Hz, 4H), 7.34-7.28 (m, 1H), 6.30 (s, 1H), 4.68 (s, 2H), 4.31 (d, J=8.1 Hz, 1H), 4.23 (dt, J=8.2, 3.0 Hz, 1H), 4.04 (dd, J=11.7, 2.5 Hz, 1H), 4.01 (d, J=10.0 Hz, 1H), 3.95 (dd, J=11.7, 3.2 Hz, 1H), 3.78 (d, J=10.1 Hz, 1H), 0.98 (s, 9H), 0.95 (s, 9H), 0.70 (s, 3H), 0.15 (s, 3H), 0.15 (s, 3H), 0.12 (s, 6H) ppm (Labile protons were not observed due to exchange with deuterated solvent); $^{13}$C NMR (125 MHz, CD$_3$OD) δ 156.6, 154.1, 150.2, 140.0, 138.1, 128.1 (2C), 127.62, 127.60 (2C), 117.4, 88.5, 83.5, 82.1, 73.4, 64.9, 62.3, 50.8, 25.2 (3C), 25.1 (3C), 18.0, 17.8, 16.8, −6.59, −6.61, −6.7, −6.9 ppm; HRMS calcd for: C$_{31}$H$_{51}$ClN$_5$O$_4$Si$_2$ [M+H]$^+$: 648.3163; found 648.3175 (1.98 ppm).

Example 2.31—Intermediate Compound

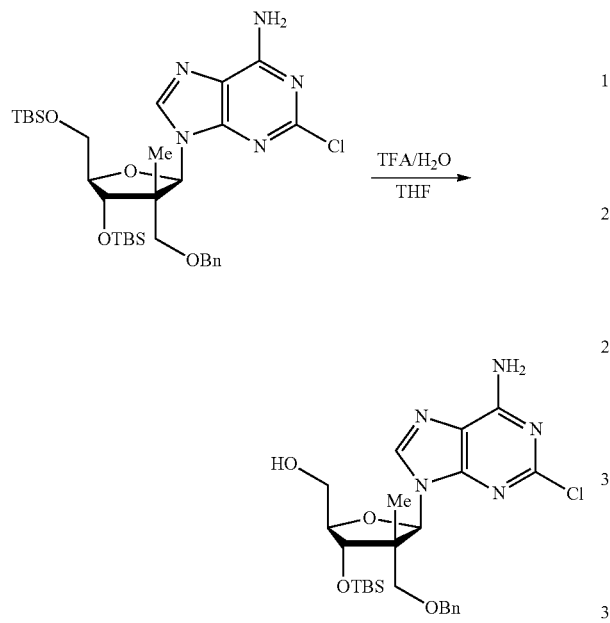

((2R,3S,4R,5R)-5-(6-amino-2-chloro-9H-purin-9-yl)-4-((benzyloxy)methyl)-3-((tert-butyldimethylsilyl)oxy)-4-methyltetrahydrofuran-2-yl)methanol. To a solution of nucleoside (358 mg, 0.552 mmol) in THF (6.1 mL, 0.09 M) at 0° C. was added TFA/H$_2$O (1:1, 3.08 mL, 0.18 M) and the mixture was stirred for 4 hours at 0° C., then quenched slowly with a saturated solution of NaHCO$_3$. Aqueous phase was extracted with Et$_2$O (2×) and the organic fractions were washed with brine, dried (MgSO$_4$), filtered and concentrated in vacuo. Crude product was purified by flash chromatography on silica gel (DCM/MeOH, 95:5) to give the product as a white solid (207 mg, 70% yield). R$_f$=0.5 (DCM/MeOH, 95:5); [α]$^{25}_D$-14 (c 0.62, MeOH); Formula: C$_{25}$H$_{36}$ClN$_5$O$_4$Si; MW: 534.13 g/mol; IR (neat) v$_{max}$ 2931, 2850, 2566, 2313, 1613 cm$^{-1}$; $^1$H NMR (500 MHz, CD$_3$OD) δ 8.49 (s, 1H), 7.42-7.33 (m, 4H), 7.33-7.28 (m, 1H), 6.31 (s, 1H), 4.79-4.60 (m, 2H), 4.32 (d, J=8.0 Hz, 1H), 4.20 (dt, J=8.1, 3.0 Hz, 1H), 4.01 (d, J=10.0 Hz, 1H), 3.97 (dd, J=12.4, 2.5 Hz, 1H), 3.84 (dd, J=12.4, 3.5 Hz, 1H), 3.77 (d, J=10.0 Hz, 1H), 0.94 (s, 9H), 0.69 (s, 3H), 0.11 (s, 6H) ppm (Labile protons were not observed due to exchange with deuterated solvent); $^{13}$C NMR (125 MHz, CD$_3$OD) δ 156.6, 154.0, 150.2, 140.4, 138.2, 128.0 (2C), 127.7 (2C), 127.5, 117.4, 88.8, 83.6, 82.2, 73.4, 65.0, 60.7, 50.7, 25.0 (3C), 17.8, 16.7, −6.7, −6.9 ppm; HRMS calcd for: C$_{25}$H$_{37}$ClN$_5$O$_4$Si [M+H]$^+$: 534.2298; found 534.2290 (−1.40 ppm).

Example 2.32—Intermediate Compound

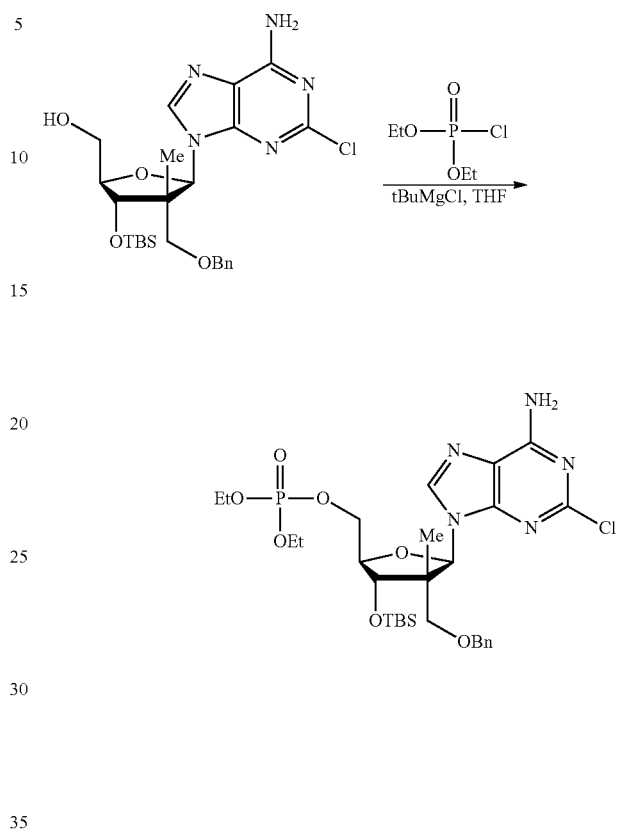

((2R,3R,4S,5R)-5-(6-amino-2-chloro-9H-purin-9-yl)-4-((benzyloxy)methyl)-3-((tert-butyldimethylsilyl)oxy)-4-methyltetrahydrofuran-2-yl)methyl diethyl phosphate. To a solution of nucleoside (200 mg, 0.374 mmol) in THF (4 mL, 0.1 M) was added t-BuMgCl (0.562 mL, 0.562 mmol) dropwise at room temperature and the mixture was stirred for 45 minutes. Diethylchlorophosphate (81.3 μL, 0.562 mmol) was added slowly and the reaction was stirred for 16 hours. The reaction was quenched by addition of MeOH and concentrated in vacuo. Crude product was purified by reverse phase (C18) flash chromatography (H$_2$O→MeCN) to give the product as a white foam (216 mg, 86% yield). R$_f$=0.5 (DCM/MeOH, 95:5); [α]$^{25}_D$+1 (c 0.78, MeOH); Formula: C$_{29}$H$_{45}$ClN$_5$O$_7$PSi; MW: 670.22 g/mol; IR (neat) v$_{max}$ 3172, 2931, 2855, 2362, 1642, 1583 cm$^{-1}$; $^1$H NMR (500 MHz, CD$_3$OD) δ 8.18 (s, 1H), 7.45-7.36 (m, 4H), 7.36-7.30 (m, 1H), 6.28 (s, 1H), 4.71 (d, J=3.2 Hz, 2H), 4.44-4.38 (m, 1H), 4.37 (s, 2H), 4.27 (dd, J=10.6, 5.7 Hz, 1H), 4.17-4.05 (m, 4H), 4.03 (d, J=10.1 Hz, 1H), 3.76 (d, J=10.1 Hz, 1H), 1.30 (qt, J=7.1, 1.1 Hz, 6H), 0.95 (s, 9H), 0.73 (s, 3H), 0.13 (s, 6H) ppm (Labile protons were not observed due to exchange with deuterated solvent); $^{13}$C NMR (125 MHz, CD$_3$OD) δ 156.7, 154.0, 150.1, 140.2, 137.9, 128.2 (2C), 127.9 (2C), 127.7, 117.7, 89.3, 83.0, 81.6 (d, J=7.6 Hz), 73.5, 67.0 (d, J=5.8 Hz), 65.1, 64.2 (t, J=5.4 Hz) (2C), 50.5, 25.0 (3C), 17.7, 16.6, 15.0 (t, J=5.8 Hz) (2C), −6.7, −6.9 ppm; HRMS calcd for: C$_{29}$H$_{45}$ClN$_5$NaO$_7$PSi [M+Na]$^+$: 692.2407; found 692.2419 (1.78 ppm).

Example 2.33—Cardioprotective Compound-LCB2165

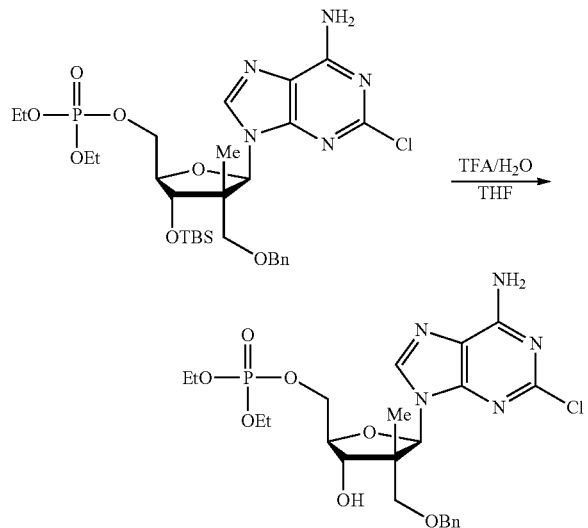

((2R,3S,4R,5R)-5-(6-amino-2-chloro-9H-purin-9-yl)-4-((benzyloxy)methyl)-3-hydroxy-4-methyltetrahydrofuran-2-yl)methyl diethyl phosphate (LCB2165). To a solution of TBS protected nucleoside (29.3 mg, 0.0437 mmol) in THF (0.5 mL, 0.1 M) was slowly added a mixture of TFA/H$_2$O (8:2) (0.5 mL, 0.1 M) at room temperature and open atmosphere. After 4 hours, MeOH was added and the reaction was concentrated in vacuo, then co-evaporated with MeOH (3×). Crude product was purified by reverse phase (C18) flash chromatography (H$_2$O/MeCN, 50:50) to provide the final product as a white solid (10.9 mg, 45% yield). R$_f$=0.4 (DCM/MeOH, 90:10); [α]$^{25}_D$+8 (c 1.02, MeOH); Formula: C$_{23}$H$_{31}$ClN$_5$O$_7$P; MW: 555.95 g/mol; IR (neat) v$_{max}$ 3370, 2979, 2909, 2383, 1613 cm$^{-1}$; $^1$H NMR (500 MHz, CD$_3$OD) δ 8.17 (s, 1H), 7.43 (d, J=6.8 Hz, 2H), 7.39 (appt, J=7.2 Hz, 2H), 7.36-7.31 (m, 1H), 6.25 (s, 1H), 4.77-4.64 (m, 2H), 4.50-4.40 (m, 2H), 4.38-4.32 (m, 1H), 4.25 (ddd, J=11.1, 5.7, 2.5 Hz, 1H), 4.17-4.02 (m, 4H), 3.93 (d, J=11.2 Hz, 1H), 3.77 (d, J=11.2 Hz, 1H), 1.28 (dtd, J=10.7, 7.1, 1.0 Hz, 6H), 0.74 (s, 3H) ppm (Labile protons were not observed due to exchange with deuterated solvent); $^{13}$C NMR (125 MHz, CD$_3$OD) δ 156.8, 153.9, 149.9, 140.5, 137.9, 128.2 (2C), 128.1 (2C), 127.8, 117.9, 89.6, 83.0, 81.6 (d, J=7.7 Hz), 73.5, 67.1 (d, J=5.8 Hz), 64.2 (t, J=5.7 Hz) (2C), 64.0, 50.4, 16.4, 15.0 (t, J=5.8 Hz) (2C) ppm; HRMS calcd for: C$_{23}$H$_{32}$ClN$_5$O$_7$P [M+H]$^+$: 556.1722; found 556.1748 (4.61 ppm).

Example 2.34—Intermediate Compound

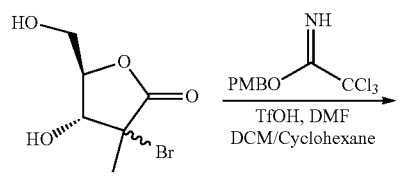

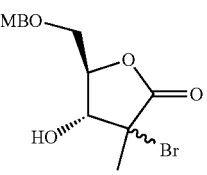

(4R,5R)-3-bromo-4-hydroxy-5-(((4-methoxybenzyl)oxy)methyl)-3-methyldihydrofuran-2(3H)-one. To a solution of lactones (2.01 g, 8.92 mmol) in DCM/Cyclohexane (1:2, 90 mL, 0.1 M) with DMF (~3 mL) at 0° C. was added 4-methoxybenzyl-2,2,2-trichloroacetimidate (2.04 mL, 9.81 mmol) and TfOH (78.7 μL, 0.892 mmol) dropwise. The mixture was warmed to room temperature, stirred for 16 hours and quenched with Et$_3$N (187 μL, 1.34 mmol) at 0° C. After 10 minutes, the reaction was concentrated in vacuo and the crude product was purified by flash chromatography on silica gel (Hexanes/Et$_2$O, 30:70) to give the products (2.60 g, 84% yield) as a pale yellow solid in a ~16:1 ratio. R$_f$=0.25 (Hexanes/Et$_2$O, 30:70); Formula: C$_{14}$H$_{17}$BrO$_5$; MW: 345.19 g/mol; IR (neat) v$_{max}$ 3435, 2931, 2866, 1782, 1513 cm$^{-1}$; $^1$H NMR (500 MHz, CDCl$_3$) δ 7.26 (d, J=8.6 Hz, 4H$_{a,b}$), 6.90 (d, J=8.6 Hz, 4H$_{a,b}$), 4.71 (d, J=6.0 Hz, 2H$_b$), 4.53 (d, J=2.0 Hz, 2H$_a$), 4.35 (dt, J=5.9, 4.9 Hz, 1H$_b$), 4.25 (ddd, J=8.3, 4.0, 2.8 Hz, 1H$_a$), 3.85 (dd, J=11.5, 2.8 Hz, 2H$_a$), 3.82 (s, 6H$_{a,b}$), 3.80-3.77 (m, 3H$_b$), 3.74 (dd, J=11.5, 4.0 Hz, 1H$_a$), 1.95 (s, 3H$_a$), 1.87 (s, 3H$_b$) ppm (Labile protons were not observed due to exchange with deuterated solvent); $^{13}$C NMR (125 MHz, CDCl$_3$) δ 171.5, 159.5, 129.5 (2C), 129.3, 113.9 (2C), 81.5, 74.3, 73.4, 66.1, 61.7, 55.3, 24.0 ppm; HRMS calcd for: C$_{14}$H$_{17}$BrNaO$_5$ [M+Na]$^+$: 367.0152; found 367.0151 (-0.21 ppm).

Example 2.35—Intermediate Compound

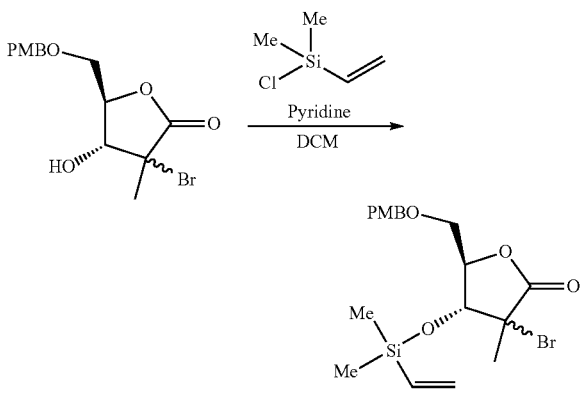

(4R,5R)-3-bromo-4-((dimethyl(vinyl)silyl)oxy)-5-(((4-methoxybenzyl)oxy)methyl)-3-methyldihydrofuran-2(3H)-one. To a solution of lactones (2.60 g, 7.53 mmol) in DCM (75 mL, 0.1 M) at 0° C. was added pyridine (1.83 mL, 22.6 mmol) and chloro(dimethyl)vinylsilane (1.13 mL, 8.29 mmol). The reaction was stirred at room temperature for 16 hours, then concentrated in vacuo. Precipitate was removed by filtration over celite with Et$_2$O and crude product was purified by flash chromatography on silica gel (Hexanes/Et$_2$O, 60:40) to give the two products (2.63 g, 81% yield) as a colorless oil in α-3:1 ratio. R$_f$=0.5 (Hexanes/Et$_2$O, 50:50); Formula: C$_{18}$H$_{25}$BrO$_5$Si; MW: 429.38 g/mol; IR (neat) v$_{max}$ 2947, 2866, 1793, 1513 cm$^{-1}$; $^1$H NMR (500 MHz, CDCl$_3$) δ 7.26 (d, J=8.6 Hz, 4H$_{a,b}$), 6.91 (d, J=8.7 Hz, 4H$_{a,b}$), 6.17-6.05 (m, 4H$_{a,b}$), 5.85 (dd, J=17.4, 6.6 Hz, 1H$_a$), 5.82 (dd, J=18.9, 5.1 Hz, 1H$_b$), 4.73 (d, J=5.8 Hz, 1H$_b$), 4.54 (s, 2H$_b$), 4.51 (d, J=1.5 Hz, 2H$_a$), 4.33-4.24 (m, 2H$_{a,b}$), 3.94 (d, J=8.1 Hz, 1H$_a$), 3.83 (s, 6H$_{a,b}$), 3.81 (d, J=2.0 Hz, 1H$_a$), 3.78 (dd, J=11.2, 4.0 Hz, 1H$_b$), 3.68 (dd, J=11.2, 4.9 Hz, 1H$_b$), 3.63 (dd, J=11.8, 3.2 Hz, 1H$_a$), 1.87 (s, 3H$_a$), 1.82 (s, 3H$_b$), 0.28 (s, 3H$_b$), 0.27 (s, 6H$_{a,b}$), 0.26 (s, 3H$_a$) ppm; $^{13}$C NMR (125 MHz, CDCl$_3$) δ 173.2, 172.1, 159.4, 136.2, 136.1, 134.8, 134.7, 129.52 (2C), 129.46, 113.9 (2C), 83.1, 81.3, 78.2, 74.1, 73.3, 73.2, 67.2, 65.2, 59.9, 56.8, 55.3, 24.5, 22.1, −1.4, −1.58, −1.62, −1.7 ppm; HRMS calcd for: C$_{18}$H$_{25}$BrNaO$_5$Si [M+Na]$^+$: 451.0547; found 451.0545 (−0.51 ppm).

Example 2.36—Intermediate Compound

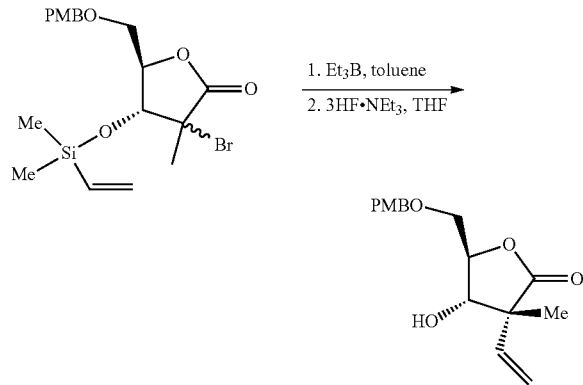

(3R,4S,5R)-4-hydroxy-5-(((4-methoxybenzyl)oxy) methyl)-3-methyl-3-vinyldihydroofuran-2(3H)-one. To a solution of lactones (1.15 g, 2.68 mmol) in toluene (27 mL, 0.1 M) at 0° C. with open atmosphere was added triethylborane (2.68 mL, 2.68 mmol) over 5 hours with air bubbling into the solution. The reaction was transferred into a plastic flask, then 3HF·NEt$_3$ (873 µL, 5.36 mmol) and THF (27 mL, 0.1 M) were added at 0° C. The mixture was stirred for 16 hours at room temperature and quenched slowly by cannulation into a saturated solution of NaHCO$_3$ at 0° C. Aqueous phase was extracted with Et$_2$O (2×) and organic fractions were dried (MgSO$_4$), filtered and concentrated in vacuo. Crude product was purified by flash chromatography on silica gel (Hexanes/Et$_2$O, 40:60) to give the product (475 mg, 61% yield) as a colorless oil. R$_f$=0.3 (Hexanes/Et$_2$O, 20:80); [α]$^2_D$+57 (c 0.57, MeOH); Formula: C$_{16}$H$_{20}$O$_5$; MW: 292.33 g/mol; IR (neat) ν$_{max}$ 3435, 2935, 2866, 1771, 1513 cm$^{-1}$; $^1$H NMR (500 MHz, CDCl$_3$) δ 7.27 (d, J=8.6 Hz, 2H), 6.91 (d, J=8.6 Hz, 2H), 5.93 (dd, J=17.6, 10.7 Hz, 1H), 5.39 (d, J=10.7 Hz, 1H), 5.27 (d, J=17.6 Hz, 1H), 4.54 (d, J=1.4 Hz, 2H), 4.21 (dt, J=8.8, 4.4 Hz, 1H), 4.10 (d, J=8.4 Hz, 1H), 3.83 (s, 3H), 3.76 (dd, J=4.5, 2.3 Hz, 2H), 1.41 (s, 3H) ppm (Labile protons were not observed due to exchange with deuterated solvent); $^{13}$C NMR (125 MHz, CDCl$_3$) δ 176.2, 159.5, 132.9, 129.5 (2C), 129.4, 118.4, 113.9 (2C), 79.8, 77.1, 73.5, 68.2, 55.3, 51.1, 20.5 ppm; HRMS calcd for: C$_{16}$H$_{20}$NaO$_5$ [M+Na]$^+$: 315.1203; found 315.1199 (−1.15 ppm).

Example 2.37—Intermediate Compound

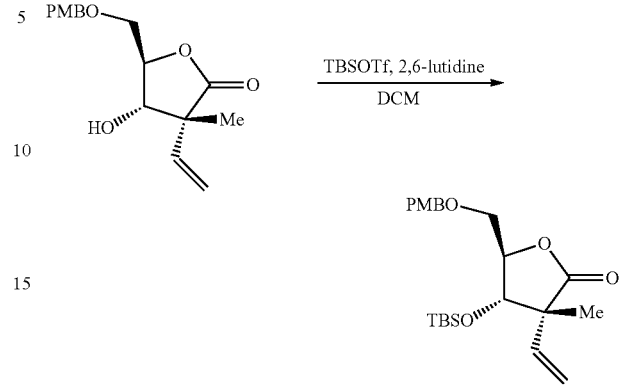

(3R,4S,5R)-4-((tert-butyldimethylsilyl)oxy)-5-(((4-methoxybenzyl)oxy)methyl)-3-methyl-3-vinyldihydrofuran-2(3H)-one. To a solution of lactone (1.71 g, 5.84 mmol) in DCM (60 mL, 0.1 M) at 0° C. was added 2,6-lutidine (1.69 mL, 14.6 mmol) and TBSOTf (2.65 mL, 11.7 mmol) dropwise. The reaction was stirred at room temperature for 16 hours, then quenched by slowly adding a saturated solution of NaHCO$_3$ and concentrated in vacuo. The product was diluted with Et$_2$O, washed with brine and HCl [0.1 M], dried (MgSO$_4$), filtered and concentrated in vacuo. Crude product was purified by flash chromatography on silica gel (Hexanes/Et$_2$O, 60:40) to give the product (1.87 g, 79% yield) as a yellow oil. R$_f$=0.3 (Hexanes/Et$_2$O, 60:40); [α]$^{25}_D$+56 (c 1.11, MeOH); Formula: C$_{22}$H$_{34}$O$_5$Si; MW: 406.59 g/mol; IR (neat) ν$_{max}$ 2958, 2931, 2855, 1787, 1513 cm$^{-1}$; $^1$H NMR (500 MHz, CDCl$_3$) δ 7.27 (d, J=9.7 Hz, 2H), 6.90 (d, J=8.6 Hz, 2H), 5.96 (dd, J=17.6, 10.7 Hz, 1H), 5.28 (d, J=10.7 Hz, 1H), 5.22 (d, J=17.7 Hz, 1H), 4.52 (s, 2H), 4.18 (d, J=8.4 Hz, 1H), 4.14 (ddd, J=8.4, 3.8, 1.9 Hz, 1H), 3.83 (s, 3H), 3.79 (dd, J=11.6, 1.9 Hz, 1H), 3.59 (dd, J=11.6, 3.8 Hz, 1H), 1.36 (s, 3H), 0.90 (s, 9H), 0.11 (s, 3H), 0.05 (s, 3H) ppm; $^{13}$C NMR (125 MHz, CDCl$_3$) δ 176.3, 159.3, 133.8, 129.6, 129.5 (2C), 116.9, 113.8 (2C), 81.1, 76.0, 73.2, 66.6, 55.3, 51.4, 25.6 (3C), 21.0, 17.9, −4.3, −4.8 ppm; HRMS calcd for: C$_{22}$H$_{34}$NaO$_5$Si [M+Na]$^+$: 429.2068; found 429.2071 (0.84 ppm).

Example 2.38—Intermediate Compound

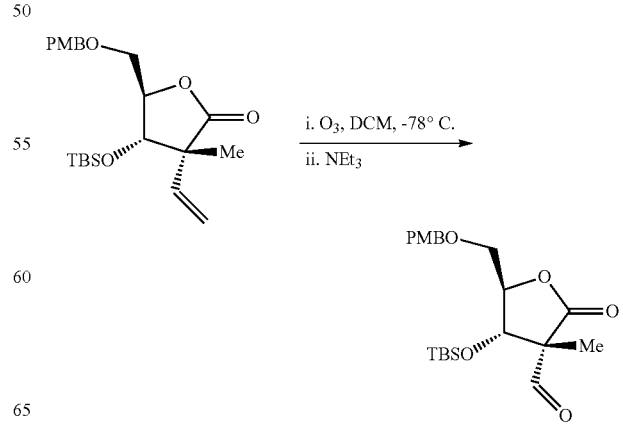

(3S,4S,5R)-4-((tert-butyldimethylsilyl)oxy)-5-(((4-methoxybenzyl)oxy)methyl)-3-methyl-2-oxotetrahydrofuran-3-carbaldehyde. To a solution of lactone (1.78 g, 4.38 mmol) in DCM (88 mL, 0.05 M) was added a pinch of Sudan Red 7B and the reaction (red/purple solution) was cooled to −78° C. Ozone was bubbled into the solution for 30 minutes (solution turned orange), then Et$_3$N (1.22 mL, 8.76 mmol) was added, the mixture was warmed to room temperature, stirred for 30 minutes and concentrated in vacuo. The product was filtered over silica with Et$_2$O to give the desired aldehyde (1.77 g, quantitative yield) as an orange oil that was used for the next reaction without further purification. R$_f$=0.55 (Hexanes/Et$_2$O, 20:80); [α]$^{25}_D$+41 (c 1.16, MeOH); Formula: C$_{21}$H$_{32}$O$_6$Si; MW: 408.57 g/mol; IR (neat) v$_{max}$ 2958, 2931, 2855, 1787, 1723, 1508 cm$^{-1}$; $^1$H NMR (500 MHz, CDCl$_3$) δ 9.58 (s, 1H), 7.25 (d, J=8.7 Hz, 2H), 6.90 (d, J=8.7 Hz, 2H), 4.54 (d, J=11.6 Hz, 1H), 4.50 (d, J=11.6 Hz, 1H), 4.48-4.42 (m, 2H), 3.83 (s, 3H), 3.78 (dd, J=11.5, 2.2 Hz, 1H), 3.62 (dd, J=11.5, 2.8 Hz, 1H), 1.51 (s, 3H), 0.86 (s, 9H), 0.10 (s, 3H), 0.03 (s, 3H) ppm; $^{13}$C NMR (125 MHz, CDCl$_3$) δ 195.8, 172.7, 159.5, 129.6 (2C), 129.3, 113.9 (2C), 82.8, 77.6, 73.4, 66.3, 60.1, 55.3, 25.5 (3C), 17.8, 15.3, −4.6, −4.9 ppm; HRMS calcd for: C$_{21}$H$_{32}$NaO$_6$Si [M+Na]$^+$: 431.1860; found 431.1860 (−0.074 ppm).

Example 2.39—Intermediate Compound

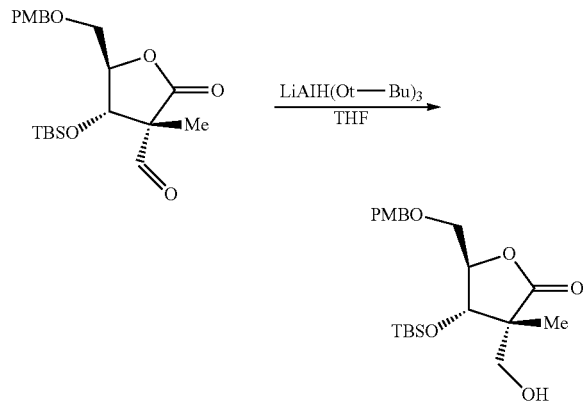

(3R,4S,5R)-4((tert-butyldimethylsilyl)oxy)-3-(hydroxymethyl)-5-(((4-methoxybenzyl)oxy)methyl)-3-methyldihydrofuran-2(3H)-one. To a solution of aldehyde (1.77 g, 4.33 mmol) in THF (44 mL, 0.1 M) at −40° C. was added LiAlH(Ot-Bu)$_3$ (6.50 mL, 6.50 mmol) dropwise and the reaction was stirred for 2 hours at −40° C. Sodium sulfate decahydrate (2.79 g, 8.66 mmol) was added and the mixture was warmed to room temperature, stirred for 45 minutes and concentrated in vacuo. The product was filtered over silica with Et$_2$O and was obtained as an orange oil that was used for the next reaction without further purification (1.25 g, 70% yield). R$_f$=0.45 (Hexanes/Et$_2$O, 20:80); [α]$^2_D$+38 (c 2.05, MeOH); Formula: C$_{21}$H$_{34}$O$_6$Si; MW: 410.58 g/mol; IR (neat) v$_{max}$ 3494, 2929, 2857, 1773, 1513, 1249 cm$^{-1}$; $^1$H NMR (500 MHz, CDCl$_3$) δ 7.25 (d, J=8.4 Hz, 2H), 6.90 (d, J=8.4 Hz, 2H), 4.55 (d, J=11.6 Hz, 1H), 4.49 (d, J=11.7 Hz, 1H), 4.38 (d, J=5.9 Hz, 1H), 4.35-4.30 (m, 1H), 3.83 (s, 3H), 3.81 (d, J=4.6 Hz, 1H), 3.79-3.71 (m, 2H), 3.61 (dd, J=11.3, 3.0 Hz, 1H), 1.19 (s, 3H), 0.92 (s, 9H), 0.14 (s, 3H), 0.07 (s, 3H) ppm (Labile protons were not observed due to exchange with deuterated solvent); $^{13}$C NMR (125 MHz, CDCl$_3$) δ 178.7, 159.4, 129.52 (2C), 129.47, 113.9 (2C), 83.7, 76.9, 73.3, 67.4, 66.4, 55.3, 49.8, 25.6 (3C), 18.8, 17.8, −4.5, −4.8 ppm; HRMS calcd for: C$_{21}$H$_{34}$NaO$_6$Si [M+Na]$^+$: 433.2017; found 433.2017 (0.14 ppm).

Example 2.40—Intermediate Compound

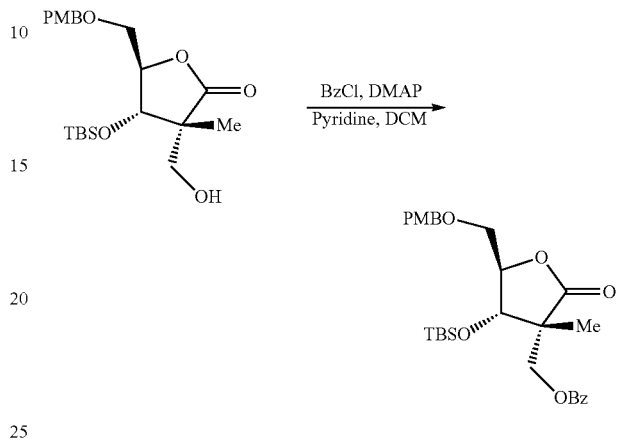

((3R,4S,5R)-4-((tert-butyldimethylsilyl)oxy)-5-(((4-methoxybenzyl)oxy)methyl)-3-methyl-2-oxotetrahydrofuran-3-yl)methyl benzoate. To a solution of alcohol (1.21 g, 2.95 mmol) in DCM (30 mL, 0.1 M) was added DMAP (36 mg, 0.295 mmol) and pyridine (1.19 mL, 14.7 mmol) at 25° C. The mixture was cooled to 0° C. and benzoyl chloride (0.856 mL, 7.37 mmol) was added. The reaction was warmed to room temperature and stirred for 24 hours, then ethylenediamine (0.395 mL, 5.89 mmol) was added slowly at 0° C. and the resultant mixture was stirred for 45 minutes at 0° C. After concentration in vacuo, the mixture was filtered over celite with Et$_2$O to remove the precipitate. The resultant oil was filtered over silica with Et$_2$O and the desired product (1.59 g, quantitative yield) was obtained as a yellow oil that was used for the next reaction without further purification. R$_f$=0.5 (Hexanes/Et$_2$O, 30:70); [α]$^{25}_D$+40 (c 1.20, MeOH); Formula: C$_{28}$H$_{38}$O$_7$Si; MW: 514.69 g/mol; IR (neat) v$_{max}$ 2953, 2931, 2857, 1782, 1725, 1268 cm$^{-1}$; $^1$H NMR (500 MHz, CDCl$_3$) δ 8.00 (d, J=7.9 Hz, 2H), 7.58 (t, J=7.5 Hz, 1H), 7.45 (appt, J=7.6 Hz, 2H), 7.27 (d, J=8.3 Hz, 2H), 6.90 (d, J=8.3 Hz, 2H), 4.70 (d, J=10.8 Hz, 1H), 4.54 (d, J=6.6 Hz, 2H), 4.41-4.33 (m, 2H), 4.18 (d, J=10.8 Hz, 1H), 3.83 (s, 3H), 3.79 (d, J=11.7 Hz, 1H), 3.60 (dd, J=11.7, 3.0 Hz, 1H), 1.35 (s, 3H), 0.84 (s, 9H), 0.11 (s, 3H), 0.02 (s, 3H) ppm; $^{13}$C NMR (125 MHz, CDCl$_3$) δ 177.0, 165.5, 159.4, 133.1, 129.7, 129.54 (3C), 129.50 (2C), 128.5 (2C), 113.9 (2C), 82.8, 74.8, 73.3, 66.9, 65.4, 55.3, 47.4, 25.6 (3C), 19.1, 17.8, −4.2, −4.9 ppm; HRMS calcd for: C$_{28}$H$_{39}$O$_7$Si [M+H]$^+$: 515.2460; found 515.2460 (0.0039 ppm).

Example 2.41—Intermediate Compound

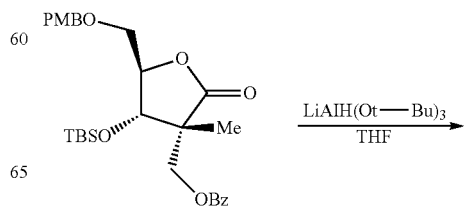

-continued

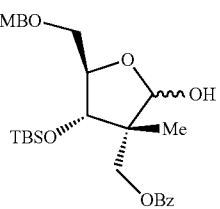

((3R,4S,5R)-4-((tert-butyldimethylsilyl)oxy)-2-hydroxy-5-(((4-methoxybenzyl)oxy)methyl)-3-methyltetrahydrofuran-3-yl)methyl benzoate. To a solution of lactone (1.59 g, 3.09 mmol) in THF (31 mL, 0.1 M) at 0° C. was added LiAlH(Ot-Bu)$_3$ (6.18 mL, 6.18 mmol) dropwise and the reaction was stirred for 24 hours at room temperature. Sodium sulfate decahydrate (1.99 g, 6.18 mmol) was added and the mixture was stirred for 45 minutes, then concentrated in vacuo. The product was filtered over silica with Et$_2$O and the desired products (1.26 g, 79% yield) were obtained in a ~3:1 ratio of anomers as a yellow oil that was used for the next reaction without further purification. R$_f$=0.45 (Hexanes/Et$_2$O, 30:70); Formula: C$_{28}$H$_{40}$O$_7$Si; MW: 516.71 g/mol; IR (neat) v$_{max}$ 3435, 2952, 2925, 2855, 1717, 1513, 1272 cm$^{-1}$; $^1$H NMR (500 MHz, CDCl$_3$) δ 8.06 (dd, J=8.3, 1.4 Hz, 4H$_{a,b}$), 7.57 (t, J=7.4 Hz, 2H$_{a,b}$), 7.46 (appq, J=8.1 Hz, 4H$_{a,b}$), 7.29 (d, J=8.6 Hz, 4H$_{a,b}$), 6.92 (d, J=8.7 Hz, 4H$_{a,b}$), 5.26 (s, 1H$_a$), 5.11 (s, 1H$_b$), 4.65 (d, J=11.5 Hz, 1H$_a$), 4.56-4.48 (m, 3H$_{a,b}$), 4.40 (d, J=11.5 Hz, 2H$_{a,b}$), 4.35 (d, J=11.5 Hz, 2H$_{a,b}$), 4.30 (d, J=6.3 Hz, 1H$_a$), 4.06 (dt, J=6.3, 2.5 Hz, 2H$_{a,b}$), 3.99 (d, J=2.6 Hz, 1H$_b$), 3.83 (s, 6H$_{a,b}$), 3.65 (dd, J=10.3, 2.5 Hz, 1H$_a$), 3.62-3.56 (m, 2H$_b$), 3.54 (dd, J=10.3, 2.6 Hz, 1H$_a$), 1.23 (s, 3H$_a$), 1.16 (s, 3H$_b$), 0.89 (s, 18H$_{a,b}$), 0.09 (s, 3H$_a$), 0.06 (s, 3H$_b$), 0.05 (s, 3H$_b$), -0.04 (s, 3H$_a$) ppm (Labile protons were not observed due to exchange with deuterated solvent); $^{13}$C NMR (125 MHz, CDCl$_3$) δ 166.54, 166.48, 159.6, 159.3, 133.0, 132.9, 130.2, 129.7 (2C), 129.6 (3C), 129.5, 129.4 (3C), 129.1 (2C), 128.41 (2C), 128.38 (2C), 114.0 (2C), 113.8 (2C), 104.0, 101.5, 86.2, 83.7, 79.0, 77.4, 73.3, 73.0, 69.8, 68.6, 66.7, 65.3, 55.3 ($^2$C$_{a,b}$), 50.9, 49.8, 25.7 ($^6$C$_{a,b}$), 19.9, 17.9, 17.8, 16.3, -4.4, -4.57, -4.61, -5.1 ppm; HRMS calcd for: C$_{28}$H$_{40}$NaO$_7$Si [M+Na]$^+$: 539.2436; found 539.2437 (0.22 ppm).

Example 2.42—Intermediate Compound

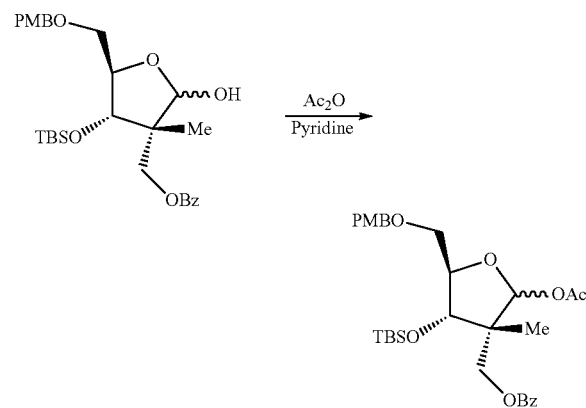

((3R,4S,5R)-2-acetoxy-4-((tert-butyldimethylsilyl)oxy)-5-(((4-methoxybenzyl)oxy)methyl)-3-methyltetrahydrofuran-3-yl)methyl benzoate. To a solution of lactols (97.8 mg, 0.189 mmol) in pyridine (2 mL, 0.1 M) at 0° C. was added acetic anhydride (71.6 μL, 0.757 mmol). The reaction was warmed to room temperature, stirred for 24 hours and concentrated in vacuo. The product was diluted with EtOAc, washed with brine, dried (MgSO$_4$), filtered and concentrated in vacuo. Crude product was purified by flash chromatography on silica gel (Hexanes/Et$_2$O, 65:35) to give a yellow oil as a mixture of products (76.7 mg, 73% yield) in a ~9:1 ratio of anomers. R$_f$=0.35 (Hexanes/Et$_2$O, 60:40); Formula: C$_{30}$H$_{42}$O$_8$Si; MW: 558.74 g/mol; IR (neat) v$_{max}$ 2952, 2931, 2850, 1744, 1723, 1513, 1272 cm$^{-1}$; $^1$H NMR (500 MHz, CDCl$_3$) δ 8.07 (dd, J=8.3, 1.4 Hz, 2H$_a$), 8.04-7.97 (m, 2H$_b$), 7.58 (t, J=7.4 Hz, 2H$_{a,b}$), 7.46 (appt, J=7.8 Hz, 4H$_{a,b}$), 7.28 (d, J=8.5 Hz, 4H$_{a,b}$), 6.90 (d, J=8.7 Hz, 4H$_{a,b}$), 6.32 (s, 1H$_a$), 6.14 (s, 1H$_b$), 4.71 (d, J=10.8 Hz, 1H$_b$), 4.53 (s, 4H$_{a,b}$), 4.47 (d, J=11.5 Hz, 1H$_a$), 4.39 (d, J=11.5 Hz, 1H$_a$), 4.26 (d, J=7.3 Hz, 1H$_a$), 4.18 (d, J=10.8 Hz, 1H$_b$), 4.09 (ddd, J=7.6, 5.0, 2.9 Hz, 2H$_{a,b}$), 3.98 (d, J=3.7 Hz, 1H$_b$), 3.83 (s, 6H$_{a,b}$), 3.67 (dd, J=10.9, 2.9 Hz, 1H$_a$), 3.63 (dd, J=4.6, 1.4 Hz, 1H$_b$), 3.60 (dd, J=11.5, 3.1 Hz, 1H$_b$), 3.54 (dd, J=10.9, 5.0 Hz, 1H$_a$), 2.04 (s, 3H$_b$), 1.99 (s, 3H$_a$), 1.25 (s, 3H$_b$), 1.20 (s, 3H$_a$), 0.90 (s, 9H$_a$), 0.84 (s, 9H$_b$), 0.13 (s, 3H$_a$), 0.05 (s, 3H$_a$), 0.02 (s, 3H$_b$), 0.01 (s, 3H$_b$) ppm; $^{13}$C NMR (125 MHz, CDCl$_3$) δ 170.1, 166.4, 159.2, 133.0, 129.6 (3C), 129.5, 129.2 (2C), 128.4 (2C), 113.7 (2C), 100.0, 84.0, 77.5, 72.8, 69.7, 66.0, 55.3, 49.5, 25.7 (3C), 21.2, 17.9, 16.1, -4.3, -4.6 ppm; HRMS calcd for: C$_{30}$H$_{42}$NaO$_8$Si [M+Na]$^+$: 581.2541; found 581.2542 (0.082 ppm).

Example 2.43—Intermediate Compound

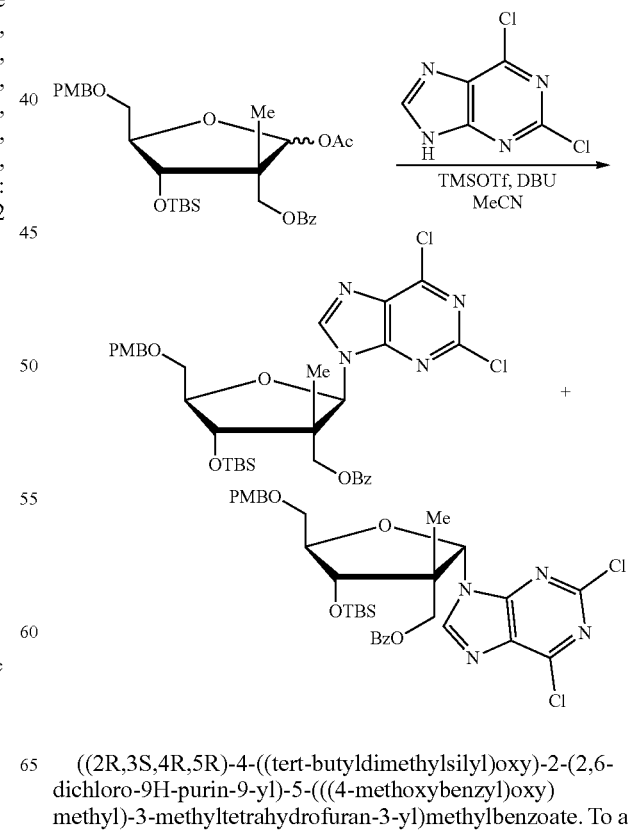

((2R,3S,4R,5R)-4-((tert-butyldimethylsilyl)oxy)-2-(2,6-dichloro-9H-purin-9-yl)-5-(((4-methoxybenzyl)oxy)methyl)-3-methyltetrahydrofuran-3-yl)methylbenzoate. To a mixture of anomeric acetates (1.95 g, 3.50 mmol) and 2,6-dichloropurine (727 mg, 3.85 mmol) in dry acetonitrile (35 mL, 0.1 M) at −10° C. was added DBU (915 μL, 6.12 mmol). The mixture was stirred and then TMSOTf (1.27 mL, 6.99 mmol) was added dropwise over 2 minutes. After 4 hours at −10° C., the reaction was warmed to room temperature, stirred for 2 hours and quenched by addition of a saturated solution of NaHCO$_3$ at 0° C. The aqueous layer was extracted with DCM (3×) and the combined organic fractions were dried (MgSO$_4$), filtered and concentrated in vacuo. $^1$H-NMR of the crude showed a ~18:1 ratio of β:α anomers. Crude product was purified by flash chromatography on silica gel (Hexanes/Et$_2$O, 60:40) to provide the pure β-anomer (1.32 g, 55% yield) as a white foam. R$_f$=0.4 (Hexanes/Et$_2$O, 50:50); [α]$^{25}_D$−14 (c 0.54, MeOH); Formula: C$_{33}$H$_{40}$Cl$_2$N$_4$O$_6$Si; MW: 687.69 g/mol; IR (neat) v$_{max}$ 3113, 2958, 2925, 2855, 1723, 1589, 1556, 1358, 1250 cm$^{-1}$; $^1$H NMR (500 MHz, CDCl$_3$) δ 9.09 (s, 1H), 8.27 (dd, J=8.3, 1.4 Hz, 2H), 7.63 (t, J=7.4 Hz, 1H), 7.55 (appt, J=7.5 Hz, 2H), 7.33 (d, J=8.7 Hz, 2H), 6.95 (d, J=8.6 Hz, 2H), 6.63 (s, 1H), 4.64 (d, J=11.6 Hz, 1H), 4.63-4.57 (m, 2H), 4.55 (d, J=8.6 Hz, 1H), 4.49 (d, J=11.7 Hz, 1H), 4.16 (dt, J=8.6, 2.0 Hz, 1H), 3.94 (dd, J=11.3, 2.0 Hz, 1H), 3.85 (s, 3H), 3.69 (dd, J=11.3, 2.0 Hz, 1H), 0.92 (s, 9H), 0.86 (s, 3H), 0.09 (s, 3H), 0.05 (s, 3H) ppm; $^{13}$C NMR (125 MHz, CDCl$_3$) δ 166.6, 159.7, 152.9, 152.7, 151.7, 145.2, 133.3, 130.8, 130.0 (2C), 129.9 (2C), 129.6, 128.8, 128.7 (2C), 114.1 (2C), 88.2, 83.1, 74.6, 73.5, 66.6, 66.1, 55.3, 50.1, 25.7 (3C), 17.9, 17.3, −4.3, −4.7 ppm; HRMS calcd for: C$_{33}$H$_{40}$Cl$_2$N$_4$NaO$_6$Si [M+Na]$^+$: 709.1986; found 709.1980 (−0.96 ppm).

Example 2.44—Intermediate Compound

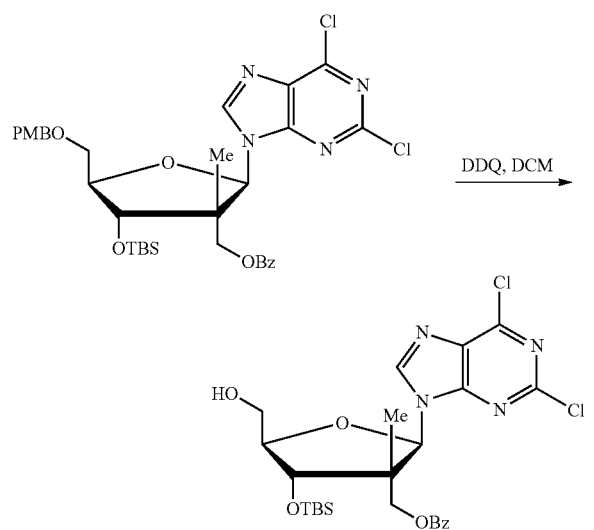

((2R,3R,4S,5R)-4-((tert-butyldimethylsilyl)oxy)-2-(2,6-dichloro-9H-purin-9-yl)-5-(hydroxymethyl)-3-methyltetrahydrofuran-3-yl)methyl benzoate. To a solution of protected nucleoside (493 mg, 717 μmol) in DCM (15 mL, 0.05 M) at room temperature with open atmosphere was added DDQ (488 mg, 2.15 mmol) and the mixture was stirred for 16 hours. A few drops of water were added and the reaction was stirred for another 7 hours. The mixture was slowly poured into a saturated solution of NaHCO$_3$. The aqueous layer was extracted with DCM (3×) and the combined organic fractions were washed with brine, dried (MgSO$_4$), filtered and concentrated in vacuo. Crude product was purified by flash chromatography on silica gel (Hexanes/Et$_2$O, 40:60) to give the product (367 mg, 90% yield) as a white solid. R$_f$=0.2 (Hexanes/Et$_2$O, 50:50); [α]$^{25}_D$−12 (c 1.67, MeOH); Formula: C$_{25}$H$_{32}$Cl$_2$N$_4$O$_5$Si; MW: 567.54 g/mol; IR (neat) v$_{max}$ 3317, 3102, 3065, 2925, 2855, 1723, 1594, 1551, 1363 cm$^{-1}$; $^1$H NMR (500 MHz, CDCl$_3$) δ 9.27 (s, 1H), 8.25 (dd, J=8.4, 1.4 Hz, 2H), 7.64 (t, J=7.4 Hz, 1H), 7.55 (appt, J=7.6 Hz, 2H), 6.62 (s, 1H), 4.66 (d, J=8.6 Hz, 1H), 4.63 (d, J=11.7 Hz, 1H), 4.52 (d, J=11.6 Hz, 1H), 4.31 (ddd, J=12.2, 4.2, 2.0 Hz, 1H), 4.16 (dt, J=8.6, 2.0 Hz, 1H), 4.06 (t, J=4.0 Hz, 1H), 3.97 (ddd, J=12.3, 3.9, 1.9 Hz, 1H), 0.96 (s, 9H), 0.92 (s, 3H), 0.22 (s, 3H), 0.17 (s, 3H) ppm; $^{13}$C NMR (125 MHz, CDCl$_3$) δ 166.5, 153.1, 152.5, 151.6, 145.5, 133.4, 130.4, 129.8 (2C), 129.5, 128.7 (2C), 88.8, 84.2, 74.2, 66.4, 59.4, 50.2, 25.7 (3C), 17.9, 17.5, −4.2, −4.6 ppm; HRMS calcd for: C$_{25}$H$_{32}$Cl$_2$N$_4$NaO$_5$Si [M+Na]$^+$: 589.1411; found 589.1398 (−2.32 ppm).

Example 2.45—Intermediate Compound

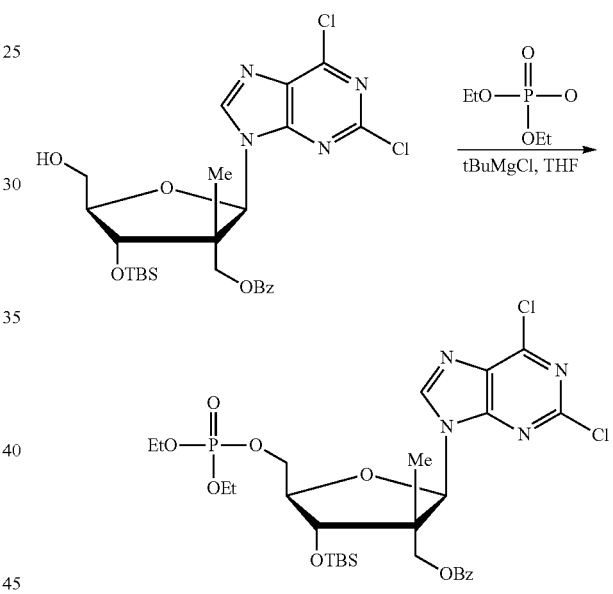

((2R,3S,4R,5R)-4-((tert-butyldimethylsilyl)oxy)-2-(2,6-dichloro-9H-purin-9-yl)-5-(((diethoxyphosphoryl)oxy)methyl)-3-methyltetrahydrofuran-3-yl)methyl benzoate. To a solution of nucleoside (349 mg, 615 μmol) in THF (6.15 mL, 0.1 M) was added t-BuMgCl (1.35 mL, 1.08 mmol) dropwise at room temperature and the mixture was stirred for 45 minutes. Diethylchlorophosphate (156 μL, 1.08 mmol) was added slowly and the reaction was stirred for 4 hours. The reaction was quenched by addition of MeOH and concentrated in vacuo. Crude product was purified by flash chromatography on silica gel (Hexanes/EtOAc, 50:50) to give the product (389 mg, 90% yield) as a yellow oil. R$_f$=0.35 (Hexanes/EtOAc, 40:60); [α]$^{25}_D$+10 (c 1.36, MeOH); Formula: C$_{29}$H$_{41}$Cl$_2$N$_4$O$_8$PSi; MW: 703.63 g/mol; IR (neat) v$_{max}$ 2953, 2931, 2850, 1723, 1589, 1551, 1358, 1267 cm$^{-1}$; $^1$H NMR (500 MHz, CDCl$_3$) δ 8.62 (s, 1H), 8.11 (dd, J=8.3, 1.4 Hz, 2H), 7.62 (t, J=7.4 Hz, 1H), 7.51 (appt, J=7.8 Hz, 2H), 6.62 (s, 1H), 4.65 (d, J=11.7 Hz, 1H), 4.52 (ddd, J=11.8, 4.7, 2.2 Hz, 1H), 4.49-4.43 (m, 2H), 4.32 (ddd, J=11.8, 4.5, 2.8 Hz, 1H), 4.26-4.17 (m, 5H), 1.43-1.35 (m, 6H), 0.95 (s, 9H), 0.94 (s, 3H), 0.20 (s, 3H), 0.17 (s, 3H)

ppm; $^{13}$C NMR (125 MHz, CDCl$_3$) δ 166.3, 153.1, 152.6, 151.9, 144.4, 133.4, 130.8, 129.6 (2C), 129.4, 128.7 (2C), 88.5, 82.5 (d, J=8.6 Hz), 75.5, 66.3, 64.5 (d, J=4.8 Hz), 64.4 (d, J=5.8 Hz), 64.3 (d, J=5.7 Hz), 49.8, 25.7 (3C), 17.9, 17.4, 16.3 (d, J=4.9 Hz), 16.2 (d, J=5.1 Hz), −4.3, −4.5 ppm; HRMS calcd for: C$_{29}$H$_{41}$Cl$_2$N$_4$NaO$_8$PSi [M+Na]$^+$: 725.1701; found 725.1688 (−1.73 ppm).

Example 2.46—Intermediate Compound

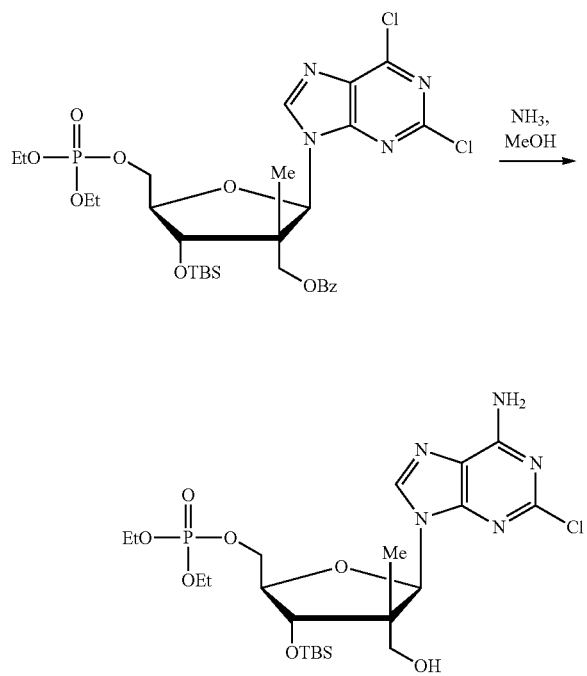

((2R,3R,4S,5R)-5-(6-amino-2-chloro-9H-purin-9-yl)-3-((tert-butyldimethylsilyl)oxy)-4-(hydroxymethyl)-4-methyltetrahydrofuran-2-yl)methyl diethyl phosphate. To a solution of nucleoside (596 mg, 847 μmol) in MeOH (21 mL, 0.04 M) in a high-pressure flask at room temperature was bubbled NH$_{3(g)}$ until saturation of the system, then the flask was rapidly closed with a high-pressure seal and the solution was stirred at 80° C. for 24 hours. The mixture was diluted with MeOH (20 mL), cooled to room temperature and concentrated in vacuo. Crude product was purified by flash chromatography on silica gel (DCM/MeOH, 95:5) to give the product (251 mg, 51% yield) as a white solid. R$_f$=0.15 (DCM/MeOH, 95:5); [α]$^{25}_D$+2 (c 1.06, MeOH); Formula: C$_{22}$H$_{39}$ClN$_5$O$_7$PSi; MW: 580.09 g/mol; IR (neat) v$_{max}$ 3296, 2952, 2928, 2855, 1613 cm$^{-1}$; $^1$H NMR (500 MHz, CDCl$_3$) δ 8.11 (s, 1H), 6.30 (s, 1H), 5.77 (s, 2H), 4.44 (ddd, J=11.5, 5.7, 2.3 Hz, 1H), 4.40 (d, J=7.3 Hz, 1H), 4.31 (dt, J=11.2, 5.1 Hz, 1H), 4.24-4.12 (m, 5H), 3.94 (dd, J=11.8, 5.6 Hz, 1H), 3.85 (dd, J=11.8, 7.6 Hz, 1H), 2.67 (dd, J=7.5, 5.6 Hz, 1H), 1.37 (tdd, J=7.1, 3.2, 1.0 Hz, 6H), 0.96 (s, 9H), 0.76 (s, 3H), 0.20 (s, 3H), 0.17 (s, 3H) ppm; $^{13}$C NMR (125 MHz, CD$_3$OD) δ 156.9, 153.8, 149.9, 140.7, 118.1, 89.4, 82.6 (d, J=7.7 Hz), 76.6, 66.9 (t, J=4.9 Hz), 64.2 (q, J=5.2, 4.5 Hz) (2C), 63.6, 50.5, 24.9 (3C), 17.5, 15.9, 15.0 (d, J=3.5 Hz), 14.9 (d, J=3.8 Hz), −5.2, −5.6 ppm; HRMS calcd for: C$_{22}$H$_{40}$ClN$_5$O$_7$PSi [M+H]$^+$: 580.2118; found 580.2121 (0.54 ppm).

Example 2.47—Intermediate Compound

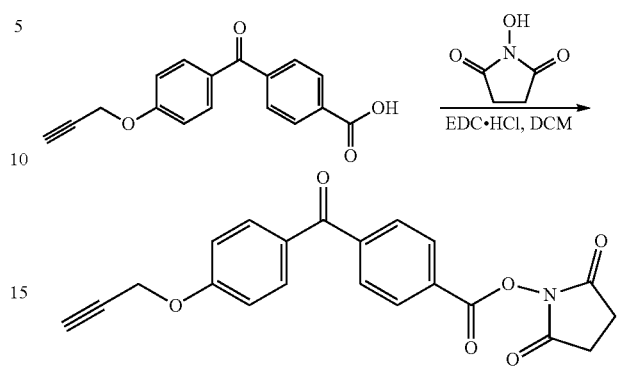

2,5-dioxopyrrolidin-1-yl 4-(4-(prop-2-yn-1-yloxy)benzoyl)benzoate. To a solution of the corresponding acid[18,19] (480 mg, 1.71 mmol) in DCM (10 mL, 0.17 M) was added N-hydroxysuccinimide (221 mg, 1.92 mmol) and EDC·HCl (368 mg, 1.92 mmol) at room temperature and the mixture was stirred for 16 hours, before addition of H$_2$O and Et$_2$O. The aqueous layer was extracted with Et$_2$O (2×) and the combined organic fractions were washed with brine, dried (MgSO$_4$), filtered and concentrated in vacuo. Crude product was purified by flash chromatography on silica gel (Hexanes/Et$_2$O, 50:50→Et$_2$O 100%) to give the product (500 mg, 77% yield) as a pale yellow solid. R$_f$=0.25 (Et$_2$O 100%); Formula: C$_{21}$H$_{15}$NO$_6$; MW: 377.35 g/mol; IR (neat) v$_{max}$ 3300, 1725, 1325, 1180 cm$^{-1}$; $^1$H NMR (500 MHz, CDCl$_3$) δ 8.27 (d, J=8.1 Hz, 2H), 7.87 (d, J=8.2 Hz, 2H), 7.84 (d, J=8.8 Hz, 2H), 7.09 (d, J=8.7 Hz, 2H), 4.81 (d, J=2.3 Hz, 2H), 2.95 (s, 4H), 2.59 (t, J=2.3 Hz, 1H) ppm; $^{13}$C NMR (125 MHz, CDCl$_3$) δ 194.2, 169.0 (2C), 161.6, 161.3, 143.7, 132.5 (2C), 130.5 (2C), 130.0, 129.7 (2C), 127.7, 114.7 (2C), 77.6, 76.4, 55.9, 25.7 (2C) ppm; HRMS calcd for: C$_{21}$H$_{15}$NO$_6$Na [M+Na]$^+$: 400.0791; found 400.0797 (1.29 ppm).

Example 2.48—Cardioprotective Compound-LCB2191

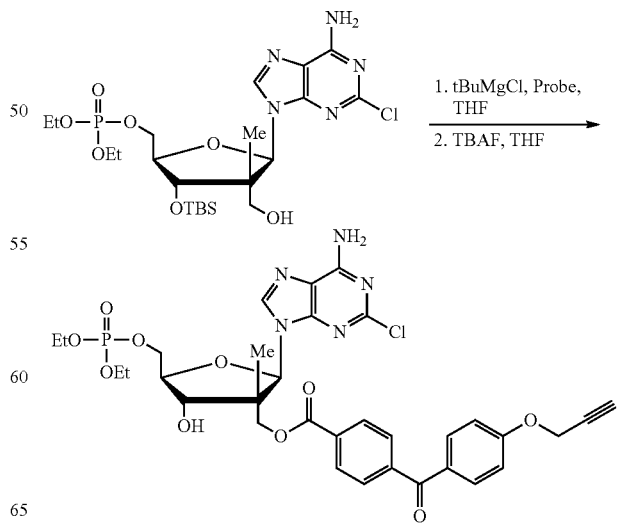

((2R,3R,4S,5R)-2-(6-amino-2-chloro-9H-purin-9-yl)-5-(((diethoxyphosphoryl)oxy)methyl)-4-hydroxy-3-methyl-tetrahydrofuran-3-yl)methyl 4-(4-(prop-2-yn-1-yloxy)benzoyl)benzoate (LCB2191). To a solution of nucleoside (26.9 mg, 0.0464 mmol) in THF (1 mL) was added t-BuMgCl (64.9 μL, 64.9 μmol) dropwise at room temperature and the mixture was stirred for 45 minutes. The photoaffinity probe (22.7 mg, 60.3 μmol) was added slowly and the reaction was stirred for 16 hours. The reaction was quenched by addition of MeOH and concentrated in vacuo. The TBS-protected intermediate was obtained as a white powder and the crude mixture was then used as such for the next reaction. To the crude mixture (12 mg, 14.2 μmol) in THF (142 μL, 0.1 M) at 0° C. was slowly added TBAF (21.4 μL, 21.4 μmol), then the mixture was warmed to room temperature and stirred for 16 hours. The reaction was quenched with a saturated solution of NaHCO$_3$ and the aqueous layer was extracted with EtOAc (3×). The combined organic fractions were dried (MgSO$_4$), filtered and concentrated in vacuo. Crude product was purified by reverse phase (C18) flash chromatography (H$_2$O/MeCN, 60:40) to give the final product as a white solid (5.3 mg, 47% yield over 2 steps). R$_f$=0.3 (DCM/MeOH, 90:10); Formula: C$_{33}$H$_{35}$ClN$_5$O$_{10}$P; MW: 728.09 g/mol; IR (neat) v$_{max}$ 3285, 2979, 2904, 2571, 2345, 1719, 1605, 1454, 1266 cm$^{-1}$; $^1$H NMR (500 MHz, CD$_3$OD) δ 8.31 (s, 1H), 8.22 (d, J=8.0 Hz, 2H), 7.85 (t, J=8.9 Hz, 4H), 7.16 (d, J=8.7 Hz, 2H), 6.52 (s, 1H), 4.91 (d, J=2.3 Hz, 2H), 4.71 (d, J=11.4 Hz, 1H), 4.54 (d, J=11.4 Hz, 1H), 4.50-4.48 (m, 2H), 4.42 (d, J=8.1 Hz, 1H), 4.30 (dd, J=8.0, 3.9 Hz, 1H), 4.23-4.13 (m, 4H), 3.05 (t, J=2.3 Hz, 1H), 1.38-1.31 (m, 6H), 0.97 (s, 3H) ppm (Labile protons were not observed due to exchange with deuterated solvent); HRMS calcd for: C$_{33}$H$_{36}$ClN$_5$O$_{10}$P [M+H]$^+$: 728.1883; found 728.1882 (−0.072 ppm).

Example 2.49—Intermediate Compound

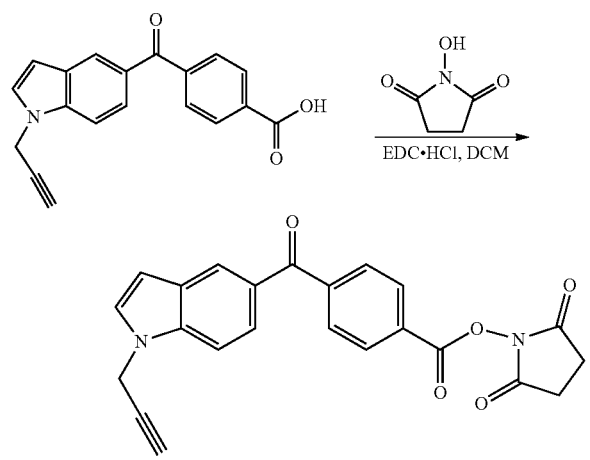

2,5-dioxopyrrolidin-1-yl 4-(1-(prop-2-yn-1-yl)-1H-indole-5-carbonyl)benzoate. To a solution of the corresponding acid[20] (506 mg, 1.67 mmol) in DCM (10 mL, 0.17 M) was added N-hydroxysuccinimide (230 mg, 2.00 mmol) and EDC·HCl (358 mg, 1.87 mmol) at rt and the mixture was stirred for 16 hours, before addition of H$_2$O. The aqueous layer was extracted with DCM (3×) and the combined organic fractions were washed with brine, dried (MgSO$_4$), filtered and concentrated in vacuo. Crude product was purified by flash chromatography on silica gel (Hexanes/EtOAc, 50:50) to give the product (257 mg, 39% yield) as a pale yellow foam. R$_f$=0.45 (Hexanes/EtOAc, 30:70); Formula: C$_{23}$H$_{16}$N$_2$O$_5$; MW: 400.39 g/mol; IR (neat) v$_{max}$ 0.3280, 1771, 1739, 1648, 1599, 1202 cm$^{-1}$; $^1$H NMR (500 MHz, CDCl$_3$) δ 8.28 (d, J=8.6 Hz, 2H), 8.10 (dd, J=1.7, 0.6 Hz, 1H), 7.91 (d, J=8.6 Hz, 2H), 7.85 (dd, J=8.7, 1.7 Hz, 1H), 7.52 (dt, J=8.7, 0.8 Hz, 1H), 7.34 (d, J=3.2 Hz, 1H), 6.67 (dd, J=3.3, 0.8 Hz, 1H), 4.96 (d, J=2.6 Hz, 2H), 2.96 (s, 4H), 2.48 (t, J=2.6 Hz, 1H) ppm; $^{13}$C NMR (125 MHz, CDCl$_3$) δ 195.8, 169.0 (2C), 161.4, 144.7, 138.4, 130.4 (2C), 129.8 (2C), 129.2, 128.9, 128.3, 127.3, 125.8, 124.0, 109.6, 104.1, 76.9, 74.2, 36.2, 25.7 (2C) ppm; HRMS calcd for: C$_{23}$H$_{16}$N$_2$NaO$_5$ [M+Na]$^+$: 423.0951; found 423.0938 (−3.26 ppm).

Example 2.50—Cardioprotective Compound-LCB2194

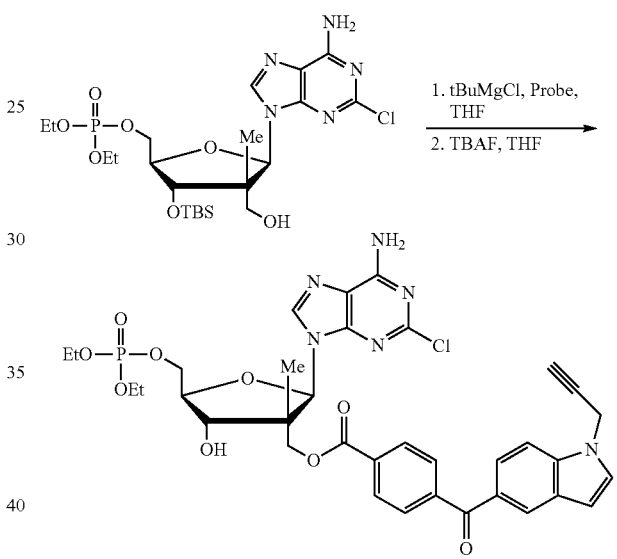

((2R,3R,4S,5R)-2-(6-amino-2-chloro-9H-purin-9-yl)-5-(((diethoxyphosphoryl)oxy)methyl)-4-hydroxy-3-methyl-tetrahydrofuran-3-yl)methyl 4-(1-(prop-2-yn-1-yl)-1H-indole-5-carbonyl)benzoate (LCB2194). To a solution of the TBS protected nucleoside (41.0 mg, 70.7 μmol) in THF (1 mL) was added t-BuMgCl (98.9 μL, 98.9 μmol) dropwise at room temperature and the mixture was stirred for 45 minutes. The photoaffinity probe (31.1 mg, 77.7 μmol) was added slowly and the reaction stirred for 16 hours. The reaction was quenched by addition of MeOH and concentrated in vacuo. The intermediate was obtained as a white powder and the crude mixture was then used as such for the next reaction. To the crude mixture (40 mg, 46.2 μmol) in THF (460 μL, 0.1 M) at 0° C. was slowly added TBAF (69.3 μL, 69.3 μmol), then the mixture was warmed to room temperature and stirred for 16 hours. The reaction was quenched with a saturated solution of NaHCO$_3$ and the aqueous layer was extracted with EtOAc (3×). The combined organic fractions were dried (MgSO$_4$), filtered and concentrated in vacuo. Crude product was purified by reverse phase (C18) flash chromatography (H$_2$O/MeCN, 60:40) to give the final product as a white solid (20 mg, 38% yield over 2 steps). R$_f$=0.3 (DCM/MeOH, 90:10); [α]$^{25}_D$−27 (c 0.35, MeOH); Formula: C$_{35}$H$_{36}$ClN$_6$O$_9$P; MW: 751.13 g/mol; IR (neat) $v_{max}$ 3269, 2968, 2909, 2362, 2329, 1722, 1612, 1316, 1259 cm$^{-1}$; $^1$H NMR (500 MHz, CD$_3$OD) δ 8.31 (s, 1H), 8.24 (d, J=7.8 Hz, 2H), 8.09 (d, J=1.8 Hz, 1H), 7.86 (d, J=7.9 Hz, 2H), 7.78 (dd, J=8.6, 1.6 Hz, 1H), 7.63 (dd, J=8.7, 0.9 Hz, 1H), 7.45 (d, J=3.3 Hz, 1H), 6.66 (dd, J=3.3, 0.8 Hz, 1H), 6.52 (s, 1H), 5.09 (d, J=2.5 Hz, 2H), 4.69 (d, J=11.4 Hz, 1H), 4.54 (d, J=11.5 Hz, 1H), 4.52-4.47 (m, 2H), 4.42 (d, J=8.3 Hz, 1H), 4.31 (dd, J=8.0, 3.9 Hz, 1H), 4.22-4.13 (m, 4H), 2.90 (t, J=2.5 Hz, 1H), 1.34 (tdd, J=7.0, 5.2, 1.0 Hz, 6H), 0.96 (s, 3H) ppm (Labile protons were not observed due to exchange with deuterated solvent); $^{13}$C NMR (125 MHz, CD$_3$OD) δ 196.9, 165.7, 156.7, 154.1, 150.2, 142.9, 139.6, 138.6, 132.2, 129.5, 129.4 (2C), 129.2 (2C), 128.5, 128.3, 125.2, 123.3, 117.6, 109.5, 103.3, 88.6, 82.1 (d, J=8.0 Hz), 77.4, 74.9, 73.6, 66.8, 66.3 (d, J=4.1 Hz), 64.4 (d, J=2.9 Hz), 64.3 (d, J=2.7 Hz), 49.1, 35.2, 16.1, 15.1 (d, J=2.9 Hz), 15.0 (d, J=3.0 Hz) ppm; HRMS calcd for: $C_{35}H_{37}ClN_6O_9P$ [M+H]$^+$: 751.2043; found 751.2043 (0.078 ppm).

REFERENCES

The present description refers to a number of documents, the content of which is herein incorporated by reference in their entirety. These documents include, but are not limited to, the following:

1. Zhou, S. Y., Mamdani, M., Qanud, K., Shen, J. B., Pappano, A. J., Kumar, T. S., Jacobson, K. A., Hintze, T., Recchia, F. A., and Liang, B. T. (2010) Treatment of heart failure by a methanocarba derivative of adenosine monophosphate: implication for a role of cardiac purinergic P2X receptors. *J. Pharmacol. Exp. Ther.* 333, 920-928
2. Kumar, T. S., Yang, T., Mishra, S., Cronin, C., Chakraborty, S., Shen, J. B., Liang, B. T., and Jacobson, K. A. (2013) 5'-Phosphate and 5'-phosphonate ester derivatives of (N)-methanocarba adenosine with in vivo cardioprotective activity. *J. Med. Chem.* 56, 902-914
3. Rochette, L., Guenancia, C., Gudjoncik, A., Hachet, O., Zeller, M., Cottin, Y., and Vergely, C. (2015) Anthracyclines/trastuzumab: new aspects of cardiotoxicity and molecular mechanisms. *Trends Pharmacol. Sci.* 36, 326-348
4. Lipshultz, S. E., Adams, M. J., Colan, S. D., Constine, L. S., Herman, E. H., Hsu, D. T., Hudson, M. M., Kremer, L. C., Landy, D. C., Miller, T. L., Oeffinger, K. C., Rosenthal, D. N., Sable, C. A., Sallan, S. E., Singh, G. K., Steinberger, J., Cochran, T. R., Wilkinson, J. D., American Heart Association Congenital Heart Defects Committee of the Council on Cardiovascular Disease in the Young, C. o. B. C. S. C. o. C., and Stroke Nursing, C. o. C. R. (2013) Long-term cardiovascular toxicity in children, adolescents, and young adults who receive cancer therapy: pathophysiology, course, monitoring, management, prevention, and research directions: a scientific statement from the American Heart Association. *Circulation* 128, 1927-1995
5. Zidan, A., Sherief, L. M., El-sheikh, A., Saleh, S. H., Shahbah, D. A., Kamal, N. M., Sherbiny, H. S., and Ahmad, H. (2015) NT-proBNP as early marker of subclinical late cardiotoxicity after doxorubicin therapy and mediastinal irradiation in childhood cancer survivors. *Dis. Markers* 2015, 513219
6. Aries, A., Paradis, P., Lefebvre, C., Schwartz, R. J., and Nemer, M. (2004) Essential role of GATA-4 in cell survival and drug-induced cardiotoxicity. *Proc Natl Acad Sci USA* 101, 6975-6980
7. Paradis, P., Dali-Youcef, N., Paradis, F. W., Thibault, G., and Nemer, M. (2000) Overexpression of angiotensin II type I receptor in cardiomyocytes induces cardiac hypertrophy and remodeling. *Proc Natl Acad Sci USA* 97, 931-936
8. Maharsy, W., Aries, A., Mansour, O., Komati, H., and Nemer, M. (2014) Ageing is a risk factor in imatinib mesylate cardiotoxicity. *Eur. J. Heart Fail.* 16, 367-376
9. van Berlo, J. H., Maillet, M., and Molkentin, J. D. (2013) Signaling effectors underlying pathologic growth and remodeling of the heart. *J. Clin. Invest.* 123, 37-45
10. Charron, F., Tsimiklis, G., Arcand, M., Robitaille, L., Liang, Q., Molkentin, J. D., Meloche, S., and Nemer, M. (2001) Tissue-specific GATA factors are transcriptional effectors of the small GTPase RhoA. *Genes Dev.* 15, 2702-2719
11. Aries, A., Whitcomb, J., Shao, W., Komati, H., Saleh, M., and Nemer, M. (2014) Caspase-1 cleavage of transcription factor GATA4 and regulation of cardiac cell fate. *Cell Death Dis* 5, e1566
12. Berge, S. M., Bighley, L. D., and Monkhouse, D. C. (1977) Pharmaceutical salts. *J. Pharm. Sci.* 66, 1-19
13. Remington's Pharmaceutical Sciences, t. E., (Mack Publishing Company, Easton, Pa., 1990).
14. Broder, H., Gottlieb, R. A., and Lepor, N. E. (2008) Chemotherapy and cardiotoxicity. *Rev. Cardiovasc. Med.* 9, 75-83
15. Pantazi, E., Bejaoui, M., Folch-Puy, E., Adam, R., and Rosello-Catafau, J. (2016) Advances in treatment strategies for ischemia reperfusion injury. *Expert Opin. Pharmacother.* 17, 169-179
16. Komati, H., Maharsy, W., Beauregard, J., Hayek, S., and Nemer, M. (2011) ZFP260 is an inducer of cardiac hypertrophy and a nuclear mediator of endothelin-1 signaling. *J. Biol. Chem.* 286, 1508-1516
17. Yang, X. P., Liu, Y. H., Rhaleb, N. E., Kurihara, N., Kim, H. E., and Carretero, O. A. (1999) Echocardiographic assessment of cardiac function in conscious and anesthetized mice. *Am. J. Physiol.* 277, H1967-1974
18. Wilkinson, M. C. (2011) "Greener" Friedel-Crafts acylations: a metal- and halogen-free methodology. *Org. Lett.* 13, 2232-2235
19. Bandyopadhyay, S. B., D. *Eur. J. Org. Chem.* 2011, 751-758.
20. Cisar, J. S., and Cravatt, B. F. (2012) Fully functionalized small-molecule probes for integrated phenotypic screening and target identification. *J. Am. Chem. Soc.* 134, 10385-10388.
21. Merck Sharp & Dohme Corp: WO 2012/142085.

The invention claimed is:

1. A compound of formula:

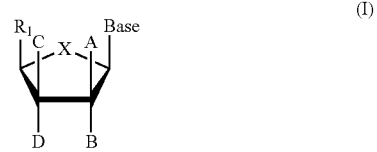

or a pharmaceutically acceptable salt thereof, wherein:
A is $C_1$-$C_6$ alkyl,
B is —$(CH_2)_n$M, —C≡N, or

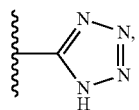

n is 1 to 3;
$R_1$ is

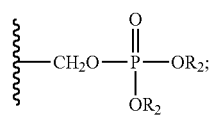

$R_2$ is the same or different and is $C_2$-$C_6$ alkyl;
M is —$OR_3$, —$SR_3$, aryl, —$C(O)OR_3$, or —$OC(O)R_4$;
$R_3$ is —H, $C_1$-$C_6$ alkyl, aryl, aryl-$C_1$-$C_6$ alkyl, or $C_1$-$C_6$ alkylaryl, wherein each of the alkyl and aryl groups is optionally substituted with one or more groups selected from halo, mono- to per-halo $C_1$-$C_6$ alkyl, —CN, —C(O)OH, —C(O)$OR_4$, —$N_3$, —$C_1$-$C_6$ alkyl-C(O)$OR_4$, —$CF_3$, —$C_1$-$C_6$ alkyl-$N_3$, and —$SiF_5$;
$R_4$ is $C_1$-$C_6$ alkyl, aryl, heteroaryl, $C_1$-$C_6$ alkylaryl, aryl-$C_1$-$C_6$ alkyl, wherein each of the alkyl, aryl and heteroaryl groups is optionally substituted with one or more groups selected from halo, —CN, alkynyl, alkynyloxy, —C(O)OH, —$N_3$, —$CF_3$, —$C_1$-$C_6$ alkyl-$N_3$, —$SiF_5$, —$NH_2$, and —$NHR_3$;
C is —H, halo, azido, —$OR_3$, —CN, or —$CF_3$;
D is OH;
X is O or S; and
Base is

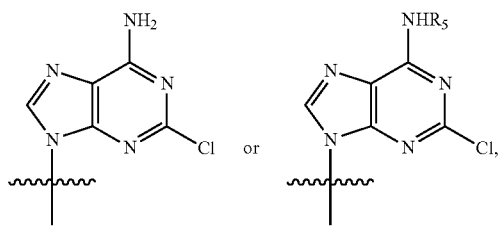

and
$R_5$ is —H, —C(O)—$C_1$-$C_4$ alkyl, aryl, alkylaryl, or arylalkyl, wherein each of the alkyl and aryl group is optionally substituted with one or more groups selected from halo, —$R_4$, —$CF_3$, and —$N_3$.

2. The compound of claim 1, wherein n is 1.
3. The compound of claim 1, wherein M is —$OR_3$ or —$OC(O)R_4$.
4. The compound of claim 3, wherein $R_3$ is —H, $C_1$-$C_6$ alkyl, or aryl-$C_1$-$C_6$ alkyl, wherein the aryl of the aryl-$C_1$-$C_6$ alkyl is optionally substituted with one or more:
a) halo,
b) mono- to per-halo $C_1$-$C_6$ alkyl,
c) —$N_3$, and/or
d) —$C_1$-$C_6$ alkyl-$N_3$.

5. The compound of claim 4, wherein $R_3$ is —H, methyl, isopropyl, benzyl,

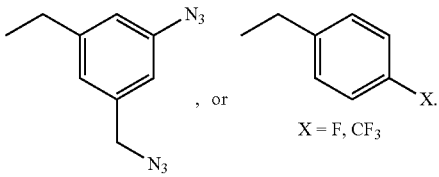

6. The compound of claim 3, wherein, in —OC(O)$R_4$ in M, $R_4$ is aryl or heteroaryl, the aryl and heteroaryl being optionally substituted with one or more groups selected from halo, —CN, alkynyl, alkynyloxy, —C(O)OH, —$N_3$, —$CF_3$, —$C_1$-$C_6$ alkyl-$N_3$, —$SiF_5$, —$NH_2$, and —$NHR_3$.

7. The compound of claim 3, wherein, in —OC(O)$R_4$ in M, $R_4$ is

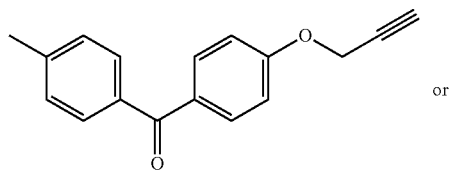

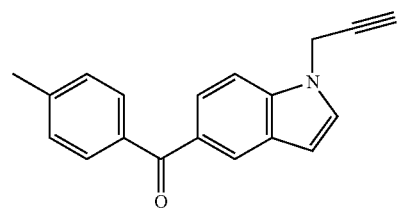

8. The compound of claim 1, wherein X is O.
9. The compound of claim 1, wherein $R_5$ represents —H, —C(O)—$C_1$-$C_4$ alkyl, arylalkyl, or aryl, wherein the aryl group is optionally substituted with one or more groups selected from halo, —$R_4$, —$CF_3$, and —$N_3$.

10. The compound of claim 1 being:

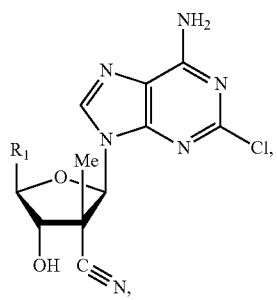

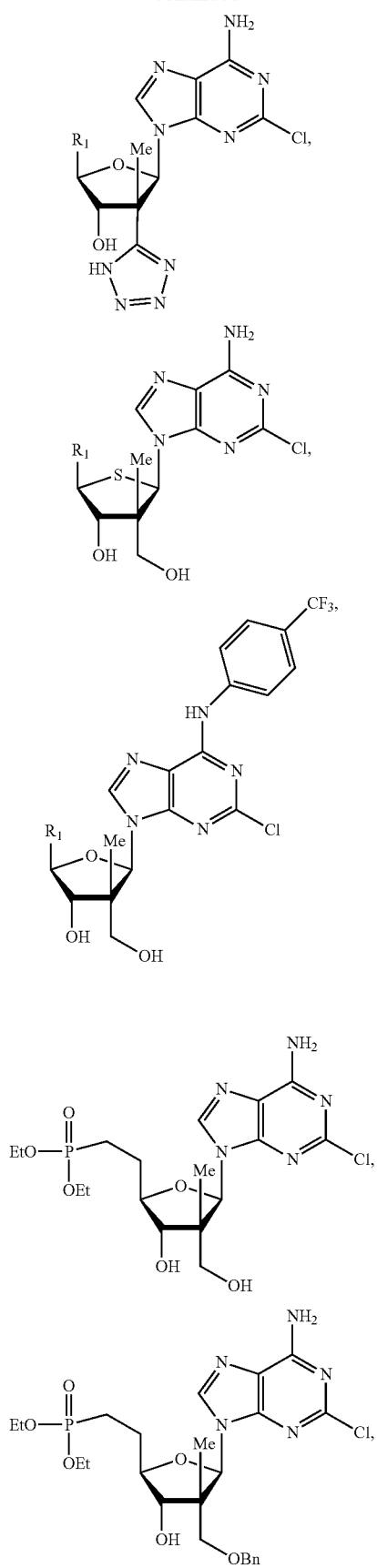
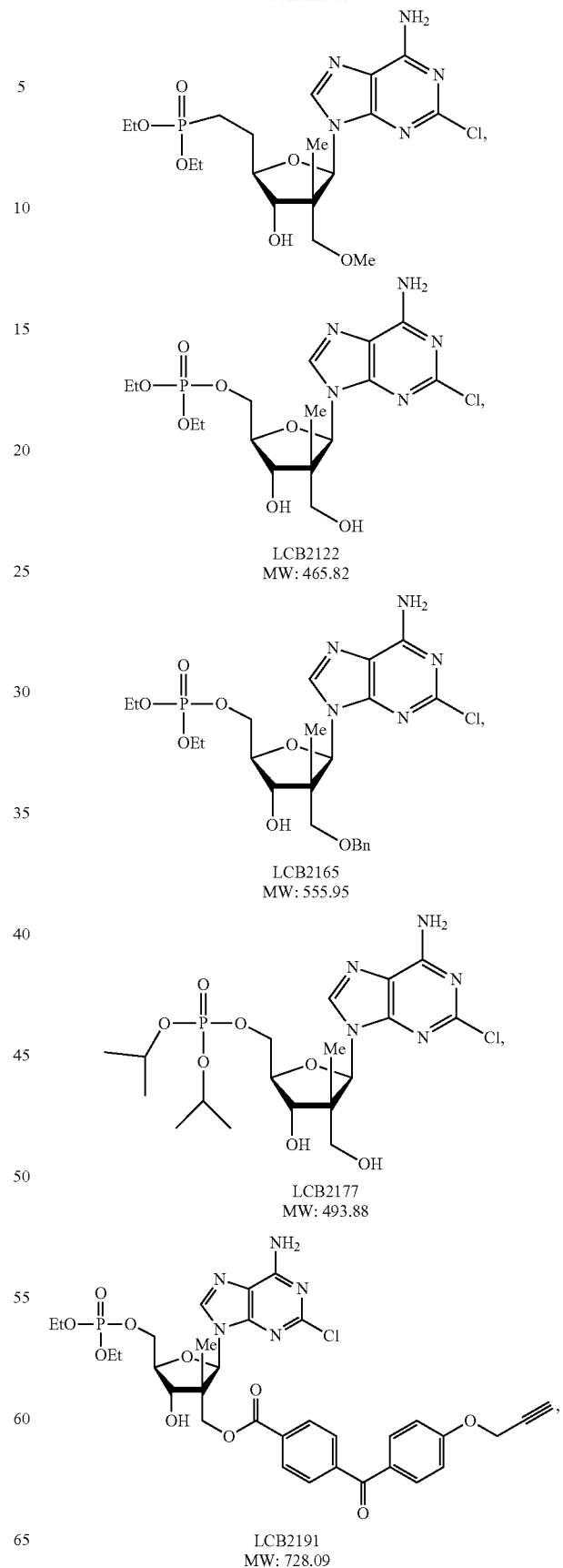

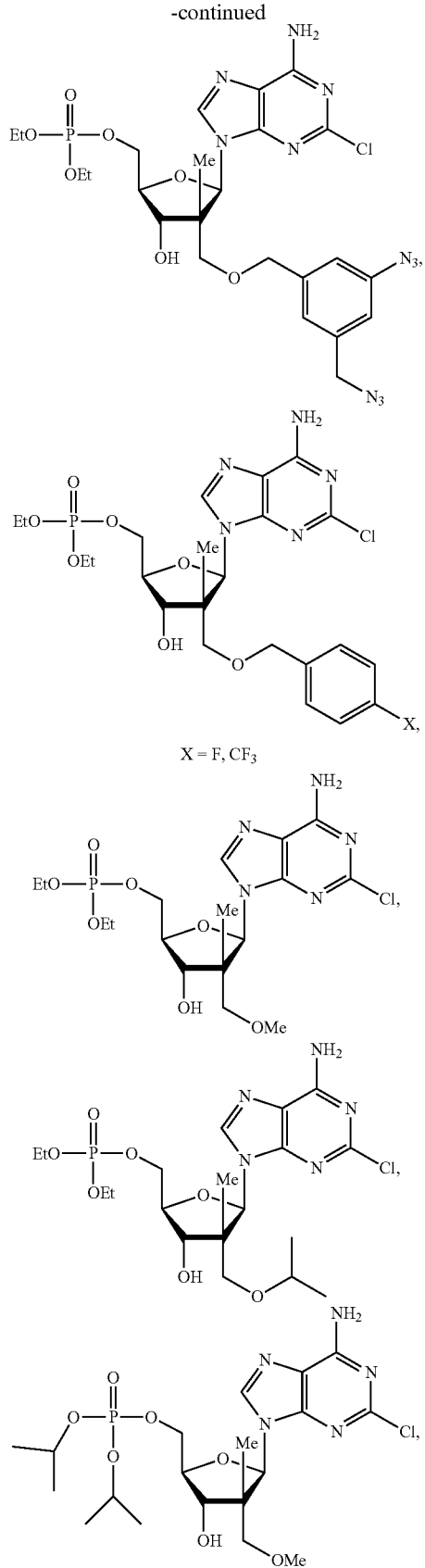

X = F, CF₃

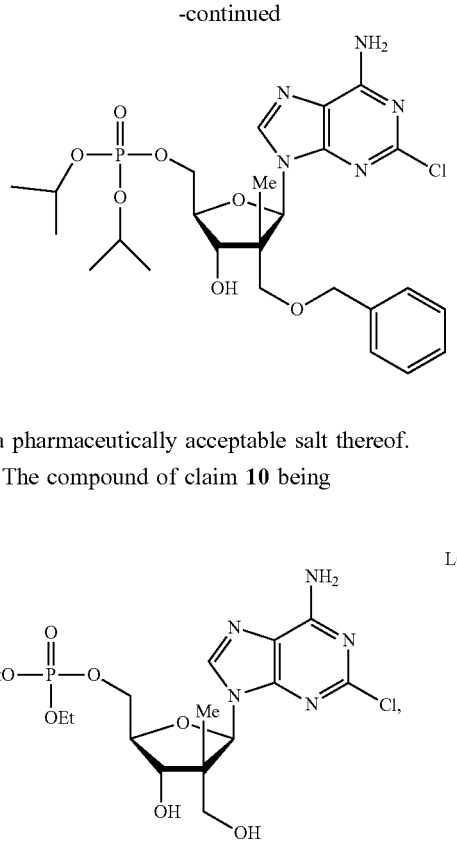

or a pharmaceutically acceptable salt thereof.

11. The compound of claim 10 being

LCB2122

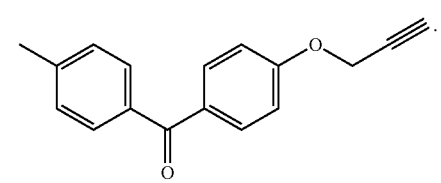 [SMILES: C#CCOc1ccc(C(=O)c2ccc(C)cc2)cc1]

or a pharmaceutically acceptable salt thereof.

12. The compound of claim 1, wherein A is methyl.

13. The compound of claim 1, wherein B is —(CH₂)ₙM.

14. The compound of claim 3, wherein $R_3$ is —H, $C_1$-$C_6$ alkyl, or aryl.

15. The compound of claim 3, wherein $R_4$ is aryl optionally substituted with alkynyloxy.

16. The compound of claim 3, wherein $R_4$ is

17. The compound of claim 1, wherein C is H.

18. The compound of claim 1, wherein $R_2$ is ethyl or isopropyl.

19. The compound of claim 1, wherein $R_5$ represents —H or arylalkyl.

\* \* \* \* \*